(12) United States Patent
Koya et al.

(10) Patent No.: US 9,102,601 B2
(45) Date of Patent: Aug. 11, 2015

(54) COMPOUNDS FOR THE TREATMENT OF PROLIFERATIVE DISORDERS

(71) Applicant: Synta Pharmaceuticals Corp., Lexington, MA (US)

(72) Inventors: Keizo Koya, Chestnut Hill, MA (US); Teresa Kowalczyk Przewloka, Tewksbury, MA (US); Shoujun Chen, Bedford, MA (US); Jun Jiang, Norwood, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 14/336,852

(22) Filed: Jul. 21, 2014

(65) Prior Publication Data

US 2015/0080386 A1     Mar. 19, 2015

Related U.S. Application Data

(62) Division of application No. 12/310,303, filed as application No. PCT/US2007/018380 on Aug. 20, 2007, now Pat. No. 8,785,451.

(60) Provisional application No. 60/839,066, filed on Aug. 21, 2006.

(51) Int. Cl.
| | | |
|---|---|---|
| C07C 327/56 | (2006.01) |
| C07C 337/08 | (2006.01) |
| C07D 213/53 | (2006.01) |
| C07D 307/52 | (2006.01) |
| C07D 333/22 | (2006.01) |
| C07D 211/84 | (2006.01) |
| C07D 239/04 | (2006.01) |
| C07D 263/10 | (2006.01) |
| C07D 271/10 | (2006.01) |
| C07D 317/28 | (2006.01) |
| C07D 339/08 | (2006.01) |
| C07D 413/14 | (2006.01) |

(52) U.S. Cl.
CPC ............. *C07C 327/56* (2013.01); *C07C 337/08* (2013.01); *C07D 211/84* (2013.01); *C07D 213/53* (2013.01); *C07D 239/04* (2013.01); *C07D 263/10* (2013.01); *C07D 271/10* (2013.01); *C07D 307/52* (2013.01); *C07D 317/28* (2013.01); *C07D 333/22* (2013.01); *C07D 339/08* (2013.01); *C07D 413/14* (2013.01); *C07C 2101/14* (2013.01); *C07C 2101/18* (2013.01)

(58) Field of Classification Search
None
See application file for complete search history.

(56) References Cited

PUBLICATIONS

Horig et al., J. Translational Med. 2:44 (2004).*

* cited by examiner

*Primary Examiner* — Michael Barker
(74) *Attorney, Agent, or Firm* — McCarter & English, LLP; Steven G. Davis

(57) ABSTRACT

Disclosed are compounds and pharmaceutical compositions that are useful for treating a subject with a proliferative disorder, such as cancer. The disclosed compounds and pharmaceutical compositions are also useful for treating disorders responsive to Hsp70 induction and/or natural killer induction.

15 Claims, 24 Drawing Sheets

COMPOUNDS FOR THE TREATMENT OF PROLIFERATIVE DISORDERS

RELATED APPLICATION

This application claims the benefit of U.S. Provisional Application No. 60/839,066, filed on Aug. 21, 2006. The entire teachings of the above application are incorporated herein by reference.

BACKGROUND OF THE INVENTION

Heat shock proteins (HSPs) are found in virtually all prokaryotic and eukaryotic cells where they support folding of nascent polypeptides, prevent protein aggregation, and assist transport of other proteins across membranes. The proteins in the Hsp70 family (referred to collectively as "Hsp70") play a dual role of protecting cells from lethal damage after environmental stress, on the one hand, and targeting cells for immune mediated cytolytic attack on the otherhand. Increased expression of Hsp70 in the cytoplasma is known to protect a broad range of cells under stress by by preventing the misfolding, aggregation and denaturation of cytoplasmic proteins and inhibiting various apoptotic pathways (Mosser, et al., Mol Cell Biol. 2000 October; 20(19): 7146-7159; Yenari, Adv Exp Med Biol, 2002, 513, 281-299; Kiang and Tsokos, Pharmacol Ther. 1998; 80(2):182-201). However, membrane-bound Hsp70 provides a target structure for cytolytic attack mediated by natural killer cells.

Cells can experience stress due to temperature; injury (trauma); genetic disease; metabolic defects; apoptosis; infection; toxins; radiation; oxidants; excess/lack of nutrients or metabolic products; and the like. For example, it is known in the art that cells damaged in the following variety of medical conditions can experience a protective effect in response to Hsp70.

Protein misfolding/aggregation conditions resulting in neurodegeneration include Alzheimers' disease (Zhang, et al., J. Neuroscience, 2004, 24(23), 5315-5321; Klettner, Drug News Perspect, 2004 17(5), 299-306); Huntington's disease (Klettner, ibid); Parkinson's disease (Auluck, et al., Science, 2002, 295(5556), 865-868); and the like. Other neurodegenerative conditions include spinal/bulbar muscular atrophy (Sobue, Nihonr Shinkei Seishin Yakurigaku Zasshi, 2001, 21(1), 21-25); and familial amyotrophic lateral sclerosis (Howland, et al., Proc Nat Acad. Sci USA, 2002, 99(3), 1604-1609; Sobue, ibid; Vleminck, et al., J Neuropathol Exp Neurol, 2002, 61(11), 968-974).

Ischemia and associated oxidative damage affects diverse tissues including: neurons and glia (Carmel, et al., Exp Neurol, 2004, 185(1) 81-96; Renshaw and Warburton, Front Biosci, 2004, 9, 110-116; Yenari, Adv Exp Med Biol, 2002, 513, 281-299; Kelly and Yenari, Curr Res Med Opin, 2002, 18 Suppl 2, s55-60; Lee, et al., Exp Neurol, 2001, 170(1), 129-139; Klettner, ibid; Klettner and Herdegen, Br J Pharmacol, 2003, 138(5), 1004-1012); cardiac muscle (Marber, M. S., et al. (1995) J. Clin. Invest. 95:1446-1456; Plumier, J. C., et al. (1995) J. Clin. Invest. 95:1854-1860; Radford, N. B., et al. (1996) Proc. Natl. Acad. Sci. USA 93(6): 2339-2342; Voss, et al., Am J Physiol Heart Circ Physiol 285: H687-H692, 2003); liver tissue (Doi, et al., Hepatogastroenterology. 2001 March-April; 48(38):533-40; Gao, et al. World J Gastroenterol 2004; 10(7):1019-1027); skeletal muscle (Lepore et al., Cell Stress &Chaperones, 2001, 6(2), 93-96); kidney tissue (Chen, et al., Kidney-Int. 1999; 56: 1270-1273; Beck, et al., Am J Physiol Renal Physiol 279: F203-F215, 2000.); pulmonary tissue (Hiratsuka, et al., J Heart Lung Transplant. 1998 December; 17(12): 1238-46); pancreatic tissue (Bellmann, et al., J Clin Invest. 1995 June; 95(6): 2840-2845), and the like.

Seizure conditions that damage neurons include, e.g., epileptic seizure (Yenari, ibid; Blondeau, et al. Neuroscience 2002, 109(2), 231-241); or chemically induced seizure (Tsuchiya, et al., Neurosurgery, 2003, 53(5), 1179-1187).

Thermal stresses include hyperthermia conditions such as fever, heat stroke, and the like (Barclay and Robertson, J Neurobiol, 2003 56(4), 360-271; Sato, et al., Brain Res, 1996, 740(1-2), 117-123); and hypothermia (Kandor and Goldberg, Proc Natl Acad Sci USA. 1997 May 13; 94(10): 4978-4981).

Aging includes conditions such as atherosclerosis Which affects smooth muscle cells (Minowada, G. and Welch, W. J. (1995) J. Clin. Invest. 95:3-12; Johnson, A. J., et. al. (1995) Arterio. Thromb. Vasc. Biol. 15(1):27-36).

Other conditions include radiation damage, e.g., from ultraviolet light to tissues such as murine fibroblasts (Simon, M. M., et al. (1995) J. Clin. Res. 95(3): 926-933), and light damage to retinal cells (Yu, et, al, Molecular Vision 2001; 7:48-56).

Trauma includes, for example, mechanical injury, e.g., pressure damage to retinal ganglions in glaucoma (Ishii, et al., Invest Opthalmol Vis Sci, 2003, 44(5), 1982-1992).

Toxic conditions include doses of chemicals or biochemicals, for example, methamphetamine (Malberg & Seiden, Poster "MDMA Administration Induces Expression of HSP70 in the Rat Brain" Society for Neuroscience Annual Meeting, New Orleans, La., Oct. 25-30, 1997); antiretroviral HIV therapeutics (Keswani, et al., Annals Neurology, 2002, 53(1), 57-64); heavy metals, amino acid analogs, chemical oxidants, ethanol, glutamate, and other toxins (Ashburner, M. and Bonner, J. J. (1979) Cell: 17:241-254; Lindquist, S. (1986) Ann. Rev. Biochem. 55:1151-1191; Craig, E. A. (1985) Crit. Rev. Biochem. 18(3):239-280; Morimoto, et al., In: The Biology of Heat Shock Proteins and Molecular Chaperone, (1994) pp. 417-455. Cold Spring Harbor Laboratory Press. Cold Spring Harbor, N.Y.); and the like.

Therefore, there is a need for new methods of increasing expression of Hsp70 in order to treat disorders responsive to Hsp70.

Extracellular Hsp70 and membrane bound Hsp70 have been shown to play key roles in activation of the innate immune system: Monocytes have been shown to secrete proinflammatory cytokines in response to soluble Hsp70 protein and membrane bound Hsp70 has been shown to provide a target structure for cytolytic attack by natural killer cell.

Natural killer (NK) cells, a type of white blood cell, are known to be an important component of the body's immune system. Because the defining function of NK cells is spontaneous cytotoxicity without prior immunization, NK cells can be the first line of defense in the immune system, and are believed to play a role in attacking cancer cells and infectious diseases. Many conditions, such as immunodeficiency diseases, aging, toxin exposure, endometriosis, and the like can leave subjects with lowered NK cell activity or dysfunctional NK cells.

For example, subjects can have decreased or deficient NK cell activity, in conditions such as chronic fatigue syndrome (chronic fatigue immune dysfunction syndrome) or Epstein-Barr virus, post viral fatigue syndrome, post-transplantation syndrome or host-graft disease, exposure to drugs such as anticancer agents or nitric oxide synthase inhibitors, natural aging, and various immunodeficiency conditions such as severe combined immunodeficiency, variable immunodeficiency syndrome, and the like. (Caligiuri M, Murray C, Buchwald D, Levine H, Cheney P, Peterson D, Komaroff A L, Ritz J. Phenotypic and functional deficiency of natural killer cells in patients with chronic fatigue syndrome. Journal of Immunology 1987; 139: 3306-13; Morrison L J A, Behan W H M, Behan P O. Changes in natural killer cell phenotype in patients with post-viral fatigue syndrome. Clinical and Experimental Immunology 1991; 83: 441-6; Klingemann, H G Relevance and Potential of Natural Killer Cells in Stem Cell Transplantation Biology of Blood and Marrow Transplantation 2000; 6:90-99; Ruggeri L, Capanni M, Mancusi A, Aversa F, Martelli M F, Velardi A. Natural killer cells as a therapeutic tool in mismatched transplantation. Best Pract Res Clin Haematol. 2004 September; 17(3):427-38; Cifone M G, Ulisse S, Santoni A. Natural killer cells and nitric oxide. Int Immunopharmacol. 2001 August; 1(8):1513-24; Plackett T P, Boehmer E D, Faunce D E, Kovacs E J. Aging and innate immune cells. J Leukoc Biol. 2004 August; 76(2):291-9. Epub 2004 Mar. 23; Alpldogan O, van den Brink M R. IL-7 and IL-15: therapeutic cytokines for immunodeficiency. Trends Immunol. 2005 January; 26(1):56-64; Heusel J W, Ballas Z K. Natural killer cells: emerging concepts in immunity to infection and implications for assessment of immunodeficiency. Curr Opin Pediatr. 2003 December; 15(6):586-93; Hacein-Bey-Abina S, Fischer A, Cavazzana-Calvo M. Gene therapy of X-linked severe combined immunodeficiency. Int J Hematol. 2002 November; 76(4):295-8; Baumert E, Schlesier M, Wolff-Vorbeck G, Peter H H. Alterations in lymphocyte subsets in variable immunodeficiency syndrome Immun Infekt. 1992 July; 20(3):73-5.)

NK cells are known to have activity against a wide range of infectious pathogens such as bacteria, viruses, fungi, protozoan parasites, combined infections, e.g., combined bacterial/viral infections, and the like. NK cells are believed to be particularly important in combating intracellular infections where the pathogens replicate in the subjects cells, e.g., a substantial fraction of viruses and many other pathogens that can form intracellular infections.

For example, a wide range of fungal infections are reported to be targeted by NK cells such as *Cryptococcus neoformans*, dermatophytes, e.g., *Trichophyton rubrum, Candida albicans, Coccidioides immitis, Paracoccidioides brasiliensis*, or the like (Hidore M R, Mislan T W, Murphy J W. Responses of murine natural killer cells to binding of the fungal target *Cryptococcus neoformans* Infect Immun. 1991 April; 59(4): 1489-99; Akiba H, Motoki Y, Satoh M, Iwatsuki K, Kaneko F; Recalcitrant trichophytic granuloma associated with NK-cell deficiency in a SLE patient treated with corticosteroid. Eur J Dermatol. 2001 January-February; 11(1):58-62; Mathews H L, Witek-Janusek L. Antifungal activity of interleukin-2-activated natural killer (NK1.1+) lymphocytes against *Candida albicans*. J Med Microbiol. 1998 November; 47(11):1007-14; Ampel N M, Bejarano G C, Galgiani J N. Killing of *Coccidioides immitis* by human peripheral blood mononuclear cells. Infect Immun. 1992 October; 60(10):4200-4; Jimenez B E, Murphy J W. In vitro effects of natural killer cells against *Paracoccidioides brasiliensis* yeast phase. Infect Immun. 1984 November; 46(2):552-8.)

Also targeted by NK cells are bacteria, especially intracellular bacteria, e.g., *Mycobacterium tuberculosis, Mycobacterium avium, Listeria monocytogenes*, many different viruses, such as human immunodeficiency virus, herpesviruses, hepatitis, and the like, and viral/bacterial co-infection (Esin S, Batoni G, Kallenius G, Gaines H, Campa M, Svenson S B, Andersson R, Wigzell H. Proliferation of distinct human T cell subsets in response to live, killed or soluble extracts of *Mycobacterium tuberculosis* and *Myco. avium*. Clin Exp Immunol. 1996 June; 104(3):419-25; Kaufmann S H. Immunity to intracellular bacteria. Annu Rev Immunol. 1993; 11:129-63; See D M, Khemka P, Sahl L, Bui T, Tilles J G. The role of natural killer cells in viral infections. Scand J Immunol. 1997 September; 46(3):217-24; Brenner B G, Dascal A, Margolese R G, Wainberg M A. Natural killer cell function in patients with acquired immunodeficiency syndrome and related diseases. J Leukoc Biol. 1989 July; 46(1):75-83; Kottilil S. Natural killer cells in HIV-1 infection: role of NK cell-mediated non-cytolytic mechanisms in pathogenesis of HIV-1 infection. Indian J Exp Biol. 2003 November; 41(11): 1219-25; Herman R B, Koziel M J. Natural killer cells and hepatitis C: is losing inhibition the key to clearance? Clin Gastroenterol Hepatol. 2004 December; 2(12):1061-3; Beadling C, Slifka M K. How do viral infections predispose patients to bacterial infections? Curr Opin Infect Dis. 2004 June; 17(3):185-91)

In addition, NK cells combat protozoal infections including toxoplasmosis, trypanosomiasis, leishmaniasis and malaria, especially intracellular infections (Korbel D S, Finney O C, Riley E M. Natural killer cells and innate immunity to protozoan pathogens. Int J Parasitol. 2004 December; 34(13-14): 1517-28; Ahmed J S, Mehlhorn H. Review: the cellular basis of the immunity to and immunopathogenesis of tropical theileriosis. Parasitol Res. 1999 July; 85(7):539-49; Osman M, Lausten S B, El-Sefi T, Boghdadi I, Rashed M Y, Jensen S L. Biliary parasites. Dig Surg. 1998; 15(4):287-96; Gazzinelli R T, Denkers E Y, Sher A. Host resistance to *Toxoplasma gondii*: model for studying the selective induction of cell-mediated immunity by intracellular parasites. Infect Agents Dis. 1993 June; 2(3):139-49; Askonas B A, Bancroft G J. Interaction of African trypanosomes with the immune system. Philos Trans R Soc Lond B Biol Sci. 1984 Nov. 13; 307(1131):41-9; Allison A C, Eugui E M. The role of cell-mediated immune responses in resistance to malaria, with special reference to oxidant stress. Annu Rev Immunol. 1983; 1:361-92.)

NK cells have been shown to play a role in attacking cancer cells that present membrane bound Hsp70. It is believed that membrane bound Hsp70 binds to CD94 receptors on the surface of NK cells and cause them to produce and secrete high amounts of the enzyme, granzyme B which is thought to enter the tumor cell via interaction with membrane bound Hsp70 and induce apoptosis (see Radons and Multhoff, Exerc. Immunol. Rev. (2005), 11:17-33). Therefore, there is an urgent need for effective treatments for increasing NK cell activity for the treatment of cancer and other disorders that respond to NK induction.

SUMMARY OF THE INVENTION

Certain compounds of the invention induce Hsp70 production in cells and thereby increase the level of Hsp70 in the cytoplasm and on the surface of cells. In addition, certain compounds of the invention are cytotoxic to cancer cell lines, including multi-drug resistant cancer cell lines, and enhance the anti-proliferative and apoptotic activity (e.g., anti-cancer activity) of Taxol and taxanes analogs.

In one embodiment, the compound of the invention are represented by formula (IA):

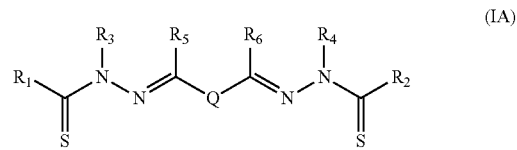

or a tautomer, pharmaceutically acceptable salt, solvate, clathrate, or a prodrug thereof, wherein:

Q is —(CR$_{14}$R$_{15}$)$_r$— or an optionally substituted 6-14 membered aryl group or an optionally substituted 5-14 membered heteroaryl group;

R$_1$ and R$_2$ are each, independently, —H, a halo, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R$_3$ and R$_4$ are each, independently, —H, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R$_5$ and R$_6$ are each, independently, —H, —NR$_{12}$R$_{13}$, —OR$_9$, —SR$_9$, a halo, CN, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R$_7$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R$_9$, for each occurrence, is independently, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or R$_{10}$ and R$_{11}$, taken together with the nitrogen to which they are attached, form an optionally substituted heterocyclyl or an optionally substituted heteroaryl;

R$_{12}$ and R$_{13}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or R$_{12}$ and R$_{13}$, taken together with the nitrogen to which they are attached, form an optionally substituted heterocyclyl or an optionally substituted heteroaryl;

R$_{14}$ and R$_{15}$, for each occurrence, are independently, —H or a substituent; or R$_{14}$ and R$_{15}$, taken together with the carbon to which they are attached, form C(O), C(S), an optionally substituted cycloalkyl, an optionally substituted cycloalkenyl, or an optionally substituted heterocyclyl;

r is an integer from 1 to 6.

In one embodiment, the compounds of the invention are represented by formula (I):

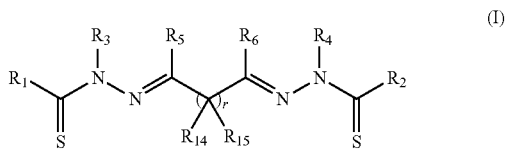

or a tautomer, pharmaceutically acceptable salt, solvate, clathrate, or a prodrug thereof, wherein values of the variables of formula (I) are as defined above for formula (IA).

In one embodiment of compound of formula (I) or (IA), R$_3$ and R$_4$ are not both —H.

In some embodiments, the compounds of formula (IA) wherein Q is —(CR$_{14}$R$_{15}$)$_r$—, or of formula (I) do not include the compound represented by the following formula:

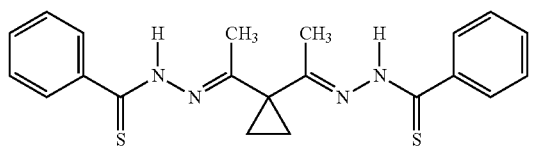 [SMILES: C/C(=N\NC(=S)c1ccccc1)C1(/C(C)=N/NC(=S)c2ccccc2)CC1]

In another embodiment, the compounds of the invention are represented by formula (II):

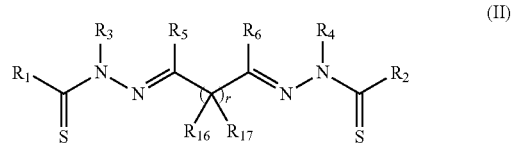

or a tautomer, pharmaceutically acceptable salt, solvate, clathrate, or a prodrug thereof, wherein:

R$_{16}$ and R$_{17}$, for each occurrence, are independently, —H or a substituent; and R$_1$, R$_2$, R$_3$, R$_4$; R$_5$, R$_6$, and r are defined as for formula (I).

In another embodiment, the compounds of the invention are represented by formula (III):

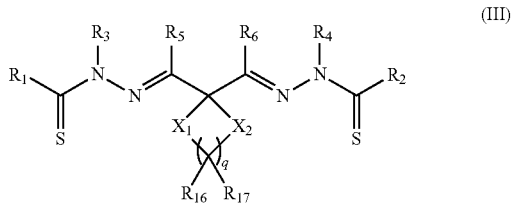

or a tautomer, pharmaceutically acceptable salt, solvate, clathrate, or a prodrug thereof, wherein:

X$_1$ and X$_2$ are each, independently, CRR, O, S, S(O)$_p$, or NR;

R, for each occurrence, is independently, —H or a substituent;

q is 0 or an integer from 1 to 6;

p is 1 or 2;

R$_1$, R$_2$, R$_3$, R$_4$, R$_5$, and R$_6$ are defined as for formula (I); and R$_{16}$, R$_{17}$, and p are defined as for formula (II).

In some embodiments, the compounds of formula (II) do not include the compound represented by the following formula:

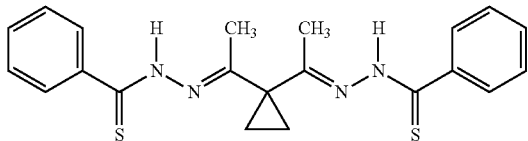 [SMILES: C/C(=N\NC(=S)c1ccccc1)C1(/C(C)=N/NC(=S)c2ccccc2)CC1]

or a salt thereof.

In another embodiment, the compounds of the invention are represented by formula (IV):

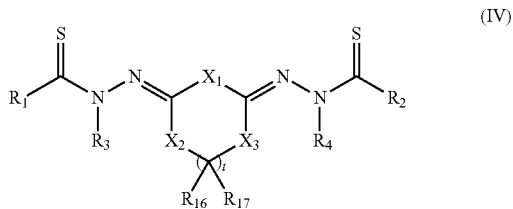

or a tautomer, pharmaceutically acceptable salt, solvate, clathrate, or a prodrug thereof, wherein:

$X_1$, $X_2$ and $X_3$ are each, independently, CRR, O, S, $S(O)_p$, or NR;

t is 0 or an integer from 1 to 3;

$R_1$, $R_2$, $R_3$, $R_4$, $R_5$, and $R_6$ are defined as for formula (I);

$R_{16}$, $R_{17}$, and p are defined as for formula (II); and

R and p are defined as for formula (III).

In another embodiment, the compounds of the invention are represented by formula (V):

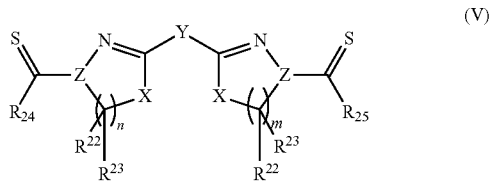

or a tautomer, pharmaceutically acceptable salt, solvate, clathrate, or a prodrug thereof, wherein:

X is $CR_{22}R_{23}$, O, S, $S(O)_p$, or NR;

Y is a bond, an optionally substituted C1-C6 alkylene, or C(O);

Z is CR or N;

$R_{22}$ and $R_{23}$, for each occurrence, are independently, —H or a substituent; or $R_{22}$ and $R_{23}$, taken together with the carbon atom to which they are attached are C(O) or C(S);

$R_{24}$ and $R_{25}$ are each, independently, —H, —$NR_{10}R_{11}$, —$OR_7$, —$SR_7$, a halo, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

m and n are each, independently, an integer from 1 to 5;

$R_3$, $R_4$, $R_5$, $R_6$, $R_7$, $R_{10}$, and $R_{11}$ are defined as for formula (I); and R and p are defined as for formula (III).

Another embodiment of the present invention is a pharmaceutical composition comprising a compound of the invention, or a tautomer, pharmaceutically acceptable salt, solvate, clathrate, or a prodrug thereof, and a pharmaceutically acceptable carrier or diluent. The pharmaceutical compositions can be used in therapy, for example, as anti-proliferative agents (e.g., anti-cancer agents). In addition, the pharmaceutical compositions can be used in therapy to treat disorders response to Hsp70 induction, or the pharmaceutical compositions can be used in therapy to treat disorders response to natural killer cell induction, such as bacterial infections, fungal infections, viral infections, or parasitic infections.

The present invention also provides for a method of treating a subject with a proliferative disorder, such as cancer. The method comprises administering to the subject an effective amount of a compound of the invention, or a tautomer, pharmaceutically acceptable salt, solvate, clathrate, or a prodrug thereof. The compound of the invention, or a tautomer, pharmaceutically acceptable salt, solvate, clathrate, or a prodrug thereof, may be administered as a mono-therapy (i.e., as the only anti-proliferative drug administered to the subject) or is co-administered with one or more other anti-cancer drugs. In one embodiment, the compound of the invention, or a tautomer, pharmaceutically acceptable salt, solvate, clathrate, or a prodrug thereof, is administered with Taxol® or a taxanes derivative.

The use of a compound of the invention, or a tautomer, pharmaceutically acceptable salt, solvate, clathrate, or a prodrug thereof, in the manufacture of a medicament for the purpose of treating a proliferative disorder, such as cancer, in an individual is also provided in the present invention.

The present invention also provides for a method of treating a subject having an Hsp70 responsive disorder, such as Alzheimers' disease, Huntington's disease, Parkinson's disease, and amyotrophic lateral sclerosis. The method comprises administering to the subject an effective amount of a compound of the invention, or a tautomer, pharmaceutically acceptable salt, solvate, clathrate, or a prodrug thereof.

The use of a compound of the invention, or a tautomer, pharmaceutically acceptable salt, solvate, clathrate, or a prodrug thereof, in the manufacture of a medicament for the purpose of disorders responsive to Hsp70 induction, such as Alzheimers' disease, Huntington's disease, Parkinson's disease, and amyotrophic lateral sclerosis, in an individual is also provided in the present invention.

The present invention also provides for a method of treating a subject having a natural killer cell responsive disorder, such as bacterial infections, fungal infections, viral infections, or parasitic infections. The method comprises administering to the subject an effective amount of a compound of the invention, or a tautomer, pharmaceutically acceptable salt, solvate, clathrate, or a prodrug thereof.

The use of a compound of the invention, or a tautomer, pharmaceutically acceptable salt, solvate, clathrate, or a prodrug thereof, in the manufacture of a medicament for the purpose of disorders responsive to natural killer cell induction, such as bacterial infection, fungal infection, viral infection, or parasitic infections, in an individual is also provided in the present invention.

The compounds of the invention or tautomer, pharmaceutically acceptable salt, solvate, clathrate, or a prodrug thereof, can be used to treat proliferative disorders such as cancer, including cancers that have become multi-drug resistant, alone or in combination with other anti-cancer agents. Thus, the compounds of the invention can be used to treat cancers where other drug regimens have either failed or become ineffective. Additionally, the compounds of the invention are particularly effective when used in combination with other anti-cancer drugs such as Taxol or a taxane analog.

DETAILED DESCRIPTION OF THE INVENTION

Figure 1:
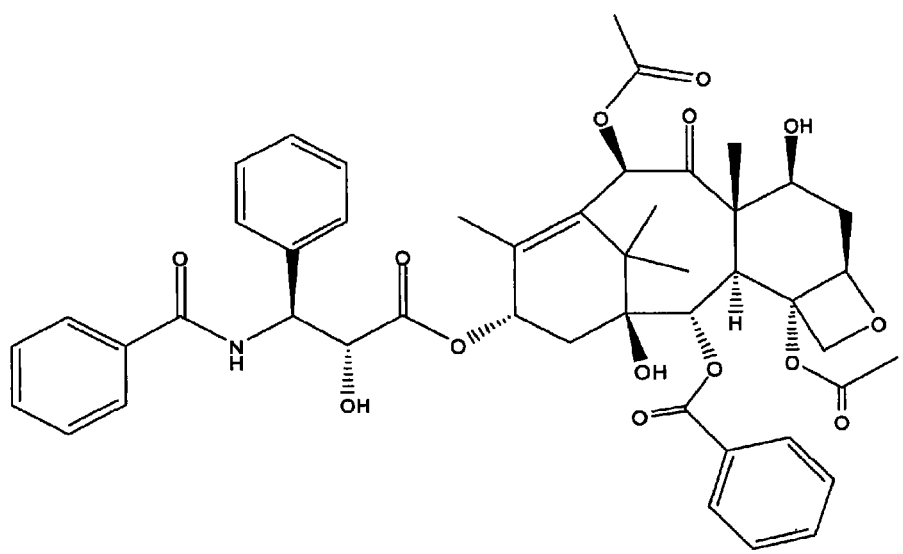
FIG. 1 is the structure of Taxol® (paclitaxel).

In one embodiment, the compound of the invention are represented by formula (IA):

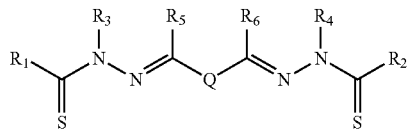

(IA)

or a tautomer, pharmaceutically acceptable salt, solvate, clathrate, or a prodrug thereof, wherein:

Q is —$(CR_{14}R_{15})_r$— or an optionally substituted 6-14 membered aryl group or an optionally substituted 5-14 membered heteroaryl group;

$R_1$ and $R_2$ are each, independently, —H, a halo, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_3$ and $R_4$ are each, independently, —H, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_5$ and $R_6$ are each, independently, —H, —$NR_{12}R_{13}$, —$OR_9$, —$SR_9$, a halo, CN, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_9$, for each occurrence, is independently, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_{12}$ and $R_{13}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally sub-stituted aralkyl, or an optionally substituted heteroaralkyl; or $R_{12}$ and $R_{13}$, taken together with the nitrogen to which they are attached, form an optionally substituted heterocyclyl or an optionally substituted heteroaryl;

$R_{14}$ and $R_{15}$, for each occurrence, are independently, —H or a substituent; or $R_{14}$ and $R_{15}$, taken together with the carbon to which they are attached, form C(O), C(S), an optionally substituted cycloalkyl, an optionally substituted cycloalkenyl, or an optionally substituted heterocyclyl;

r is an integer from 1 to 6.

In one embodiment, the compounds of the invention are represented by formula (I):

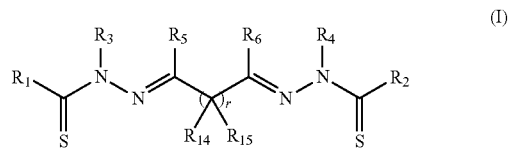

(I)

or a tautomer, pharmaceutically acceptable salt, solvate, clathrate, or a prodrug thereof, wherein values of the variables of formula (I) are as defined above for formula (IA).

In one embodiment of compound of formula (I) or (IA), $R_3$ and $R_4$ are not both —H.

In some embodiments, the compounds of formula (IA) wherein Q is —$(CR_{14}R_{15})_r$—, or of formula (I) do not include the compound represented by the following formula:

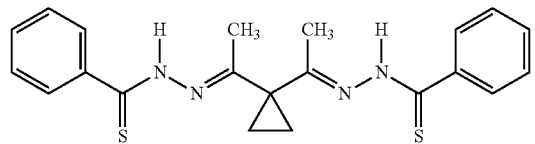 [SMILES: C/C(=N\NC(=S)c1ccccc1)C1(/C(C)=N/NC(=S)c2ccccc2)CC1]

In another embodiment, the compounds of the invention are represented by formula (II):

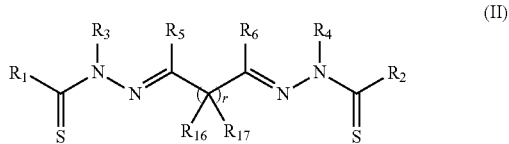

(II)

or a tautomer, pharmaceutically acceptable salt, solvate, clathrate, or a prodrug thereof, wherein:

$R_{16}$ and $R_{17}$, for each occurrence, are independently, —H or a substituent; and $R_1$, $R_2$, $R_3$, $R_4$, $R_5$, $R_6$, and r are defined as for formula (I).

In some embodiments of the compounds represented formula (I) or (II), r is 1 or 2; and $R_{16}$ and $R_{17}$, for each occurrence, are independently, —H, a lower alkyl, or a benzyl.

In another embodiment, the compounds of the invention are represented by formula (III):

(III)

or a tautomer, pharmaceutically acceptable salt, solvate, clathrate, or a prodrug thereof, wherein:

$X_1$ and $X_2$ are each, independently, CRR, O, S, $S(O)_p$, or NR;

R, for each occurrence, is independently, —H or a substituent;

q is 0 or an integer from 1 to 6;

p is 1 or 2;

$R_1$, $R_2$, $R_3$, $R_4$, $R_5$, and $R_6$ are defined as for formula (I); and $R_{16}$, $R_{17}$, and p are defined as for formula (II).

In some embodiments, the compounds of formula (III) do not include the compound represented by the following formula:

or a salt thereof.

In some embodiments of the compounds represented by formula (III), q is 2 or 3; and $R_{16}$ and $R_{17}$, for each occurrence, are independently, —H or a lower alkyl.

In some embodiments of the compounds represented by formula (III), $X_1$ and $X_2$ are both CRR. Preferably, R of CRR, for each occurrence, is independently, —H or a lower alkyl.

In some embodiments of the compounds represented by formula (III), $X_1$ and $X_2$ are both O.

In some embodiments of formula (IA), (I), (II) or (III), $R_5$ and $R_6$ are the same.

In some embodiments of formula (IA), (I), (II) or (III), $R_5$ and $R_6$ are different.

In some embodiments of formula (IA), (I), (II) or (III), $R_5$ and $R_6$ are each, independently, —H, —$NR_{12}R_{13}$, —$OR_9$, —$SR_9$, a lower haloalkyl, a lower alkyl, phenyl, or benzyl. In some embodiments, $R_9$, $R_{12}$ and $R_{13}$, for each occurrence, are independently, a lower alkyl.

In some embodiments of formula (IA); (I), (II) or (III), $R_5$ and $R_6$ are, independently, —H, a lower alkyl, a lower alkoxy, or a lower sulfanyl.

In some embodiments of formula (IA), (I), (II) or (III), $R_1$ and $R_2$ independently are an optionally substituted aryl or an optionally substituted heteroaryl; and $R_3$ and $R_4$ are each an optionally substituted alkyl, an optionally substituted alkenyl, an optionally substituted alkynyl, an optionally substituted cycloalkyl, an optionally substituted cycloalkenyl, and optionally substituted heterocyclyl. Alternatively, $R_1$ and $R_2$ are each a substituted or unsubstituted phenyl group; and $R_3$ and $R_4$ are each methyl or ethyl.

In some embodiments of formula (IA), (I), (II) or (III), $R_1$ and $R_2$ are both an optionally substituted alkyl, an optionally substituted alkenyl, an optionally substituted alkynyl, an optionally substituted cycloalkyl, an optionally substituted cycloalkenyl, an optionally substituted heterocyclyl. Alternatively, $R_1$ and $R_2$ are both a C3-C8 cycloalkyl group optionally substituted with at least one alkyl group, such as cyclopropyl or 1-methylcyclopropyl; $R_3$ and $R_4$ are both an alkyl group.

In some embodiments of formula (IA), (I), (II) or (III), $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both 4-cyanophenyl, and $R_3$ and $R_4$ are both methyl; $R_1$ and $R_2$ are both 4-methoxyphenyl, and $R_3$ and $R_4$ are both methyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both 4-cyanophenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 4-chlorophenyl, and $R_3$ and $R_4$ are both methyl; $R_1$ and $R_2$ are both 2-dimethoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2,5-difluorophenyl, and $R_3$ and $R_4$ are both methyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both cyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both methyl; $R_1$ and $R_2$ are both 1-methylcyclopropyl, and $R_3$ and $R_4$ are both ethyl; $R_1$ and $R_2$ are both 1-methylcyclopropyl, and $R_3$ is methyl, and $R_4$ is ethyl; $R_1$ and $R_2$ are both 2-methylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ and $R_2$ are both cyclohexyl, and $R_3$ and $R_4$ are both methyl; $R_1$ and $R_2$ are both cyclohexyl, and $R_3$ and $R_4$ are both phenyl; $R_1$ and $R_2$ are both methyl, and $R_3$ and $R_4$ are both methyl; $R_1$ and $R_2$ are both methyl, and $R_3$ and $R_4$ are both t-butyl; $R_1$ and $R_2$ are both methyl, and $R_3$ and $R_4$ are both phenyl; $R_1$ and $R_2$ are both t-butyl, and $R_3$ and $R_4$ are both methyl; $R_1$ and $R_2$ are ethyl, and $R_3$ and $R_4$ are both methyl; or $R_1$ and $R_2$ are both n-propyl, and $R_3$ and $R_4$ are both methyl.

In another embodiment, the compounds of the invention are represented by formula (IV):

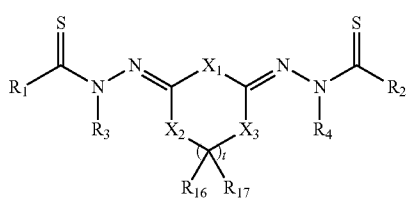

(IV)

or a tautomer, pharmaceutically acceptable salt, solvate, clathrate, or a prodrug thereof, wherein:

$X_1$, $X_2$ and $X_3$ are each, independently, CRR, O, S, $S(O)_p$, or NR;

t is 0 or an integer from 1 to 3;

$R_1$, $R_2$, $R_3$, $R_4$, $R_5$, and $R_6$ are defined as for formula (I);

$R_{16}$, $R_{17}$, and p are defined as for formula (II); and

R and p are defined as for formula (III).

In some embodiments of formula (IV), t is 0 or 2; and $R_{16}$ and $R_{17}$, for each occurrence, are independently, —H or a lower alkyl.

In some embodiments of formula (IV), $X_1$, $X_2$ and $X_3$ are all CRR; and R, for each occurrence, is independently, —H, a lower alkyl, or benzyl.

In some embodiments of formula (IV), $X_1$ is CRR; and $X_2$ and $X_3$ are each, independently, O or S. Preferably, R of CRR, for each occurrence, is independently, —H, a lower alkyl, or benzyl.

In some embodiments of formula (IV), $X_1$ is CRR; and $X_2$ and $X_3$ are both O. Preferably, R, for each occurrence, is independently, —H, a lower alkyl, or benzyl.

In some embodiments of formula (IV), $X_1$ is O, S, or NR; and $X_2$ and $X_3$ are each, independently, O or S. Preferably, R of NR is —H, a lower alkyl, or benzyl.

In some embodiments of formula (IV), $X_1$, $X_2$ and $X_3$ are all O.

In some embodiments of formula (IA), (I), (II), (III), or (IV), $R_3$ and $R_4$ are the same. Preferably, $R_3$ and $R_4$ are —H, a lower alkyl group, a phenyl, wherein the lower alkyl group and the phenyl are, independently, optionally substituted one or more halo, CN, —C(O)$R_{18}$, —C(S)$R_{18}$, —C(NR$_8$)$R_{18}$, phenyl, —OR$_{19}$, —NR$_{20}$R$_{21}$, —SR$_{19}$, —OC(O)$R_{15}$, —NR$_{19}$C(O)$R_{15}$, or —NR$_{19}$C(NR$_8$)$R_{18}$, wherein:

$R_8$ is —H, a lower alkyl, benzyl, —CN, —NO$_2$, or —C(O)$R_{18}$, or alternatively $R_8$ is —H, a lower alkyl, benzyl or —C(O)$R_{18}$;

$R_{18}$, for each occurrence, is independently, is —H, a lower alkyl, a lower haloalkyl, phenyl, benzyl, OR$_{19}$, NR$_{20}$R$_{21}$, or —SR$_{19}$;

$R_{19}$, for each occurrence, is independently, —H, a lower alkyl, a lower haloalkyl, a lower alkoxyalkyl, phenyl, or benzyl; and $R_{20}$ and $R_{21}$, for each occurrence, are independently, —H, a lower alkyl; a lower haloalkyl, a lower alkoxyalkyl, phenyl, or benzyl; or $R_{20}$ and $R_{21}$, taken together with the nitrogen atom to which they are attached, form a five or six membered heterocyclyl or a five or six membered heteroaryl.

In some embodiments of formula (IA), (I), (II), (III), or (IV), $R_3$ and $R_4$ are different. Preferably, $R_3$ and $R_4$ are each, independently, —H, a lower alkyl group, a phenyl, wherein the lower alkyl group and the phenyl are, independently, optionally substituted one or more halo, CN, —C(O)$R_8$, —C(S)$R_{18}$, —C(NR$_8$)$R_{18}$, phenyl, —OR$_{19}$, —NR$_{20}$R$_{21}$, —SR$_{19}$, —OC(O)$R_{18}$, —NR$_{19}$C(O)$R_8$, or —NR$_{19}$C(NR$_8$)$R_{18}$, wherein $R_8$, $R_{18}$, $R_{19}$, $R_{20}$ and $R_{21}$ are defined as above.

In some embodiments of formula (IA), (I), (II), (III), or (IV), $R_1$ and $R_2$ are the same. Preferably, $R_1$ and $R_2$ are selected from the group consisting of a lower alkyl, a cycloalkyl, phenyl, naphthylenyl, or a heteroaryl, each of which may be optionally substituted with one or more substituents selected from the group consisting of a halo, —NO$_2$, —CN, a lower alkyl, benzyl, —C(O)$R_{18}$, —C(S)$R_{18}$, —C(NR$_8$)$R_{15}$, phenyl, —OR$_{19}$, —NR$_{20}$R$_{21}$, —SR$_{19}$, —OC(O)$R_{18}$, —NR$_{19}$C(O)$R_{18}$, or —NR$_{19}$C(NR)$R_{18}$, wherein $R_8$, $R_{18}$, $R_{19}$, $R_{20}$ and $R_{21}$ are defined as above.

In some embodiments of formula (IA), (I), (II), (III), or (IV), $R_1$ and $R_2$ are different. Preferably, $R_1$ and $R_2$ are each, independently, selected from the group consisting of a lower alkyl, a cycloalkyl, phenyl, naphthylenyl, or a heteroaryl, each of which may be optionally substituted with one or more substituents selected from the group consisting of a halo, —NO$_2$, —CN, a lower alkyl, benzyl, —C(O)$R_8$, —C(S)$R_{18}$, —C(NR$_8$)$R_{18}$, phenyl, —OR$_{19}$, —NR$_{20}$R$_{21}$, —SR$_{19}$, —OC(O)$R_{18}$, —NR$_{19}$C(O)$R_{18}$, or —NR$_{19}$C(NR)$R_{18}$, wherein $R_8$, $R_{18}$, $R_{19}$, $R_{20}$ and $R_{21}$ are defined as above.

In another embodiment, the compounds of the invention are represented by formula (V):

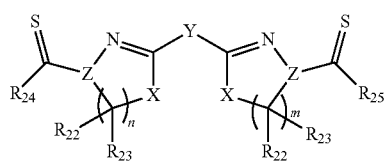

(V)

or a tautomer, pharmaceutically acceptable salt, solvate, clathrate, or a prodrug thereof, wherein:

X is CR$_{22}$R$_{23}$, O, S, S(O)$_p$, or NR;

Y is a bond, an optionally substituted C1-C6 alkylene, or C(O);

Z is CR or N;

$R_{22}$ and $R_{23}$, for each occurrence, are independently, —H or a substituent; or $R_{22}$ and $R_{23}$, taken together with the carbon atom to which they are attached are C(O) or C(S);

$R_{24}$ and $R_{25}$ are each, independently, —H, —NR$_{10}$R$_{11}$, —OR$_7$, —SR$_7$, a halo, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_7$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{10}$ and $R_{11}$, taken together with the nitrogen to which they are attached, form an optionally substituted heterocyclyl or an optionally substituted heteroaryl;

m and n are each, independently, an integer from 1 to 5;

$R_3$, $R_4$, $R_5$, and $R_6$, are defined as for formula (I); and

R and p are defined as for formula (III).

In some embodiments of formula (V), X for each occurrence is O.

In some embodiments of formula (V), X for each occurrence is S.

In some embodiments of formula (V), X for each occurrence is NR. Preferably, R of NR is —H or a lower alkyl.

In some embodiments of formula (V), X for each occurrence is $CR_{22}R_{23}$, wherein $R_{22}$ and $R_{23}$, taken together with the carbon atom to which they are attached are C(O).

In some embodiments of formula (V), X for each occurrence is $CR_{22}R_{23}$, wherein $R_{22}$ and $R_{23}$ are each, independently, —H or a lower alkyl.

In some embodiments of formula (V), wherein Z for each occurrence is N.

In some embodiments of formula (V), Z for each occurrence is CR and R of CR is —H or a lower alkyl.

In some embodiments of formula (V), n and m are the same and are 1 or 2.

In some embodiments of formula (V), n and m are different.

In some embodiments of formula (V), n and m are both 1 and each occurrence of $R_{22}$ and $R_{23}$ together with the carbon atom to which they are attached is C(O):

In some embodiments of formula (V), n and m are the same and are 1 or 2, and $R_{22}$ and $R_{23}$, for each occurrence, are independently, —H, a lower alkyl, a halo, —OH, a lower alkoxy, —SH, a lower alkylsulfanyl, —$NH_2$, a lower alkylamino, a lower dialkylamino —CN, or —$NO_2$.

In some embodiments of formula (V), Y is CRR and R, for each occurrence, is independently, —H, a lower alkyl or benzyl.

In some embodiments of formula (V), Y is a bond.

In some embodiments of formula (V), Y is C(O).

In some embodiments of formula (V), $R_{24}$ and $R_{25}$ are the same. Preferably, $R_{24}$ and $R_{25}$ are selected from the group consisting of a lower alkyl, a cycloalkyl, phenyl, naphthylenyl, or a heteroaryl, each of which may be optionally substituted with one or more substituents selected from the group consisting of a halo, —$NO_2$, —CN, a lower alkyl, benzyl, —C(O)$R_8$, —C(S)$R_{18}$, —C($NR_8$)$R_{18}$, phenyl, —$OR_{19}$, —$NR_{20}R_{21}$, —$SR_{19}$, —OC(O)$R_{18}$, —$NR_{19}$C(O)$R_{18}$, or —$NR_{19}$C($NR_8$)$R_{18}$, wherein $R_8$, $R_{18}$, $R_{19}$, $R_{20}$, and $R_{21}$ are defined as above.

In some embodiments of formula (V), $R_{24}$ and $R_{25}$ are different. Preferably, $R_{24}$ and $R_{25}$, are, independently, selected from the group consisting of a lower alkyl, a cycloalkyl, phenyl, naphthylenyl, or a heteroaryl, each of which may be optionally substituted with one or more substituents selected from the group consisting of a halo, —$NO_2$, —CN, a lower alkyl, benzyl, —C(O)$R_{18}$, —C(S)$R_{18}$, —C($NR_8$)$R_{18}$, phenyl, —$OR_{19}$, —$NR_{20}R_{21}$, —$SR_{19}$, —OC(O)$R_{18}$, —$NR_{19}$C(O)$R_{18}$, or —$NR_{19}$C($NR_8$)$R_{18}$, wherein $R_8$, $R_{18}$, $R_{19}$, $R_{20}$, and $R_{21}$ are defined as above.

In some embodiments of formula (V), $R_{24}$ and $R_{25}$ are selected from the group consisting of —$OR_{26}$, —$SR_{26}$, or —$NR_{27}R_{28}$, wherein:

$R_{26}$ is —H, a lower alkyl, a cycloalkyl, phenyl, naphthylenyl, or a heteroaryl, wherein the alkyl, cycloalkyl, phenyl, naphthylenyl, or a heteroaryl may be optionally substituted with one or more substituents selected from the group consisting of a halo, —$NO_2$, —CN, a lower alkyl, benzyl, —C(O)$R_{18}$, —C(S)$R_{18}$, —C($NR_8$)$R_{18}$, phenyl, —$OR_{19}$, —$NR_{20}R_{21}$, —$SR_{19}$, —OC(O)$R_{18}$, —$NR_{19}$C(O)$R_{18}$, or —$NR_{19}$C($NR_8$)$R_8$; and $R_{27}$ and $R_{28}$ are each, independently, —H, a lower alkyl, a cycloalkyl, phenyl, naphthylenyl, or a heteroaryl, wherein the alkyl, cycloalkyl, phenyl, naphthylenyl, or a heteroaryl may be optionally substituted with one or more substituents selected from the group consisting of a halo, —$NO_2$, —CN, a lower alkyl, benzyl, —C(O)$R_{18}$, —C(S)$R_{18}$, —C($NR_8$)$R_{18}$, phenyl, —$OR_{19}$, —$NR_{20}R_{21}$, —$SR_{19}$, —OC(O)$R_{18}$, —$NR_{19}$C(O)$R_{18}$, or —$NR_{19}$C(NR)$R_{18}$; or $R_{27}$ and $R_{28}$, taken together with the nitrogen atom to which they are attached, form a heterocyclyl or a heteroaryl, each of which may be optionally substituted with one or more substituents selected from the group consisting of a halo, —$NO_2$, —CN, a lower alkyl, benzyl, —C(O)$R_{18}$, —C(S)$R_{18}$, —C($NR_8$)$R_{18}$, phenyl, —$OR_{19}$, —$NR_{20}R_{21}$, —$SR_{19}$, —OC(O)$R_{18}$, —$NR_{19}$C(O)$R_{18}$, or —$NR_{19}$C($NR_8$)$R_{18}$, wherein $R_8$, $R_{18}$, $R_{19}$, $R_{20}$, and $R_{21}$ are defined as above.

In some embodiments of formula (V), $R_7$, for each occurrence, is independently, —H, a lower-alkyl, a lower haloalkyl, phenyl, benzyl, or pyridinyl.

In some embodiments of formula (V), $R_{10}$ and $R_{11}$, for each occurrence, are independently, —H, a lower alkyl, a lower haloalkyl, phenyl, benzyl, or pyridinyl; or $R_{10}$ and $R_{11}$, taken together with the nitrogen atom to which they are attached, are morpholinyl, piperazinyl, piperadinyl, pyrrolyl, triazolyl, tetrazolyl, or indolyl.

In some embodiments of formula (IA), (I), (II), (III), or (IV), $R_9$ is a lower alkyl, a lower haloalkyl, phenyl, benzyl, or pyridinyl.

In some embodiments of formula (IA), (I), (II), (III), or (IV), $R_{12}$ and $R_{13}$, for each occurrence, are independently, a lower alkyl, a lower haloalkyl, phenyl, benzyl, or pyridinyl; or $R_{12}$ and $R_{13}$, taken together with the nitrogen atom to which they are attached, are morpholinyl, piperazinyl, piperadinyl, pyrrolyl, triazolyl, tetrazolyl, or indolyl.

In some embodiments, each of $R_{14}$ and $R_{15}$ of formula (Ia) and (I), each of $R_{16}$ and $R_{17}$ of formula (II)-(IV), each of $R_{22}$ and $R_{23}$ of formula (V), each of CRR for $X_1$ and $X_2$ of formulas (III) and (IV), and each of CR for Z of Formula (V), independently, is —H or an optionally substituted C1-C10 alkyl, such as an optionally substituted C1-C6 alkyl. Alternatively, in some embodiments, each of $R_{14}$ and $R_{15}$ of formula (Ia) and (I), each of $R_{16}$ and $R_{17}$ of formula (II)-(IV), each of $R_{22}$ and $R_{23}$ of formula (V), each of CRR for $X_1$ and $X_2$ of formulas (III) and (IV), and each of CR for Z of Formula (V), independently, is —H or a C1-C10 alkyl, such as a C1-C6 alkyl.

In some embodiments of formula (IA), Q is an optionally substituted 6-14 membered aryl group or an optionally substituted 5-14 membered heteroaryl group. Specific examples of aryl and heteroaryl groups are described later. In one specific embodiment, Q is an optionally substituted 6-8 membered aryl group or an optionally substituted 5-6 membered heteroaryl group. In another specific embodiment, Q is selected from the group consisting of:

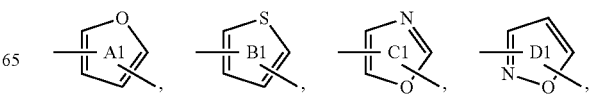

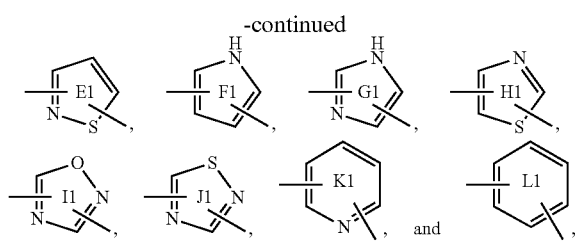
wherein each of rings A1-L1 independently is optionally substituted.
Representative examples of compounds of the invention are shown in Table 1:

TABLE 1-continued

| Compound No. | Structural formula |
|---|---|
| 16 | |
| 17 | |
| 18 | |
| 19 | |
| 20 | |
| 21 | |
| 22 | |

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "$(C_1$-$C_6)$alkyl" means a saturated straight chain or branched non-cyclic hydrocarbon having from 1 to 6 carbon atoms. Representative $(C_1$-$C_6)$alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched $(C_2$-$C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydropentalenyl, and the like. Cycloalkyl groups may be optionally substituted with one or more substituents. In some embodiments, the cycloalkyl includes from 3 to 10 carbon atoms. In some embodiments, the cycloalkyl includes from 3 to 8 carbon atoms. In some embodiments, the cycloalkyl includes from 3 to 8 carbon atoms.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents. In some embodiments, the cycloalkenyl includes' from 3 to 10 carbon atoms. In some embodiments, the cycloalkenyl includes from 3 to 8 carbon atoms. In some embodiments, the cycloalkenyl includes from 3 to 6 carbon atoms.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, a "haloalkoxy" is a haloalkyl group which is attached to another moiety via an oxygen linker.

As used herein, an "alkoxyalkyl" is an alkyl group which is substituted with an alkoxy group.

As used herein, an "alkylsulfanyl" is an alkyl group which is attached to another moiety via a sulfur linker.

As used herein, an "alkylamino" is an amino group in which one of the hydrogens is replaced with an alkyl group.

As used herein, an "dialkylamino" is an amino group in which two of the hydrogens are replaced with an alkyl groups. The alkyl groups may be the same or different.

As used herein, the term an "aromatic ring" or "aryl." means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a 6-14 membered ring. In one embodiment, the aryl group is a monocyclic ring, wherein the ring comprises 6 carbon atoms, referred to herein as "($C_6$)aryl."

As used herein, the term "aralkyl" means an aryl group that is attached to another group by a ($C_1$-$C_6$)alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "($C_1$-$C_6$)alkylene" refers to an alkylene group that has from one to six carbon atoms. Straight chain ($C_1$-$C_6$)alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH$($CH_3$)—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or an unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition. In some embodiments, the heterocyclyl includes from 3 to 10 ring atoms and 1-3 heteroatoms selected from N, O or S. In some embodiments, the heterocyclyl includes from 3 to 8 ring atoms and 1-3 heteroatoms selected from N, O or S. In some embodiments, the heterocyclyl includes from 3 to 6 ring atoms and 1-3 heteroatoms selected from N, O or S.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. In another embodiment, the heteroaromatic ring is selected from 5-8 membered monocyclic heteroaryl rings that includes 1-3 heteroatoms selected from N, O or S. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "($C_5$)heteroaryl" means an aromatic ring of 5 members, wherein at least one atom in the ring is a heteroatom such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "($C_6$)heteroaryl" means an aromatic ring of 6 members, wherein at least one atom in the ring is a heteroatom such as, for example, oxygen, nitrogen or sulfur. Representative ($C_6$)heteroaryls include pyridyl, pyridazinyl, pyrazinyl, triazinyl, tetrazinyl and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups are those which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroaralkyl, including each of $R_{14}$ and $R_{15}$ of formula (Ia) and (I), each of $R_{16}$ and $R_{17}$ of formula (II)-(IV), each of $R_{22}$ and $R_{23}$ of formula (V), each R of CRR for $X_1$ and $X_2$ of formulas (III)

and (IV), and each R of CR for Z of Formula (V), include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, a haloalkyl, $C(O)NR_{33}R_{29}$, $-C(S)NR_{33}R_{29}$, $-C(NR_{32})NR_{33}R_{29}$, $-NR_{30}C(O)R_{31}$, $-NR_{30}C(S)R_{31}$, $-NR_{30}C(NR_{32})R_{31}$, halo, $-OR_{30}$, cyano, nitro, haloalkoxy, $-C(O)R_{30}$, $-C(S)R_{30}$, $-C(NR_{32})R_{30}$, $-NR_{33}R_{29}$, $-C(O)OR_{30}$, $-C(S)OR_{30}$, $-C(NR_{32})OR_{30}$, $-OC(O)R_{30}$, $-OC(S)R_{30}$, $-OC(NR_{32})R_{30}$, $-NR_{30}C(O)NR_{33}R_{29}$, $-NR_{30}C(S)NR_{33}R_{29}$, $-NR_{30}C(NR_{32})NR_{33}R_{29}$, $-OC(O)NR_{33}R_{29}$, $-OC(S)NR_{33}R_{29}$, $-OC(NR_{32})NR_{33}R_{29}$, $-NR_{30}C(O)OR_{31}$, $-NR_{30}C(S)OR_{31}$, $-NR_{30}C(NR_{32})OR_{31}$, $-S(O)_hR_{30}$, $-OS(O)_pR_{30}$, $-NR_{30}S(O)_pR_{30}$, $-S(O)_pNR_{33}R_{29}$, $-OS(O)_pNR_{33}R_{29}$, or $-NR_{30}S(O)_pNR_{33}R_{29}$.

In some embodiments, exemplary substituents for an alkyl, alkylene, alkenyl, alkynyl, cycloalkyl, cycloalkenyl, heterocyclyl, aryl, aralkyl, heteroaryl, and heteroarylalkyl, including each of $R_{14}$ and $R_{15}$ of formula (Ia) and (I), each of $R_{16}$ and $R_{17}$ of formula (II)-(IV), each of $R_{22}$ and $R_{23}$ of formula (V), each R of CRR for $X_1$ and $X_2$ of formulas (III) and (IV), and each R of CR for Z of Formula (V), include an alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), an alkenyl, an alkynyl, a cycloalkyl, a cycloalkenyl, a heterocyclyl, an aryl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a heteroaryl, an aralkyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a heteroaralkyl, a haloalkyl, $-C(O)NR_{33}R_{29}$, $-C(S)NR_{33}R_{29}$, $-C(NR_{32})NR_{33}R_{29}$, $-NR_{30}C(O)R_{31}$, $-NR_{30}C(S)R_{31}$, $-NR_{30}C(NR_{32})R_{31}$, halo, $-OR_{30}$, cyano, nitro, haloalkoxy, $-C(O)R_{30}$, $-C(S)R_{30}$, $-C(NR_{32})R_{30}$, $-NR_{33}R_{29}$, $-C(O)OR_{30}$, $-C(S)OR_{30}$, $-C(NR_{32})OR_{30}$, $-OC(O)R_{30}$, $-OC(S)R_{30}$, $-OC(NR_{32})R_{30}$, $-NR_{30}C(O)NR_{33}R_{29}$, $-NR_{30}C(S)NR_{33}R_{29}$, $-NR_{30}C(NR_{32})NR_{33}R_{29}$, $-OC(O)NR_{33}R_{29}$, $-OC(S)NR_{33}R_{29}$, $-OC(NR_{32})NR_{33}R_{29}$, $-NR_{30}C(O)OR_{31}$, $-NR_{30}C(S)OR_{31}$, $-NR_{30}C(NR_{32})OR_{31}$, $-S(O)_hR_{30}$, $-OS(O)_pR_{30}$, $-NR_{30}S(O)_pR_{30}$, $-S(O)_pNR_{33}R_{29}$, $-OS(O)_pNR_{33}R_{29}$, or $-NR_{30}S(O)_pNR_{33}R_{29}$. Alternatively, the exemplary substituents include a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, a 3-8 membered heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-6 membered heteroaryl, a lower aralkyl (such as benzyl, and optionally substituted with one or more substituents selected from the group consisting of lower alkyl, halo, cyano, nitro, amino, mono (lower alkyl)amino, di(lower alkyl)amino, lower alkoxy, lower haloalkoxy and —OH), a lower heteroaralkyl, a lower haloalkyl, $-C(O)NR_{33}R_{29}$; $-C(S)NR_{33}R_{29}$, $-C(NR_{32})NR_{33}R_{29}$, $-NR_{30}C(O)R_{31}$, $-NR_{30}C(S)R_{31}$, $-NR_{30}C(NR_{32})R_{31}$, halo, $-OR_{30}$, cyano, nitro, haloalkoxy, $-C(O)R_{30}$, $-C(S)R_{30}$, $-C(NR_{32})R_{30}$, $-NR_{33}R_{29}$, $-C(O)OR_{30}$, $-C(S)OR_{30}$, $-C(NR_{32})OR_{30}$, $-OC(O)R_{30}$, $-OC(S)R_{30}$, $-OC(NR_{32})R_{30}$, $-NR_{30}C(O)NR_{33}R_{29}$, $-NR_{30}C(S)NR_{33}R_{29}$, $-NR_{30}C(NR_{32})NR_{33}R_{29}$, $-OC(O)NR_{33}R_{29}$, $-OC(S)NR_{33}R_{29}$, $-OC(NR_{32})NR_{33}R_{29}$, $-NR_{30}C(O)OR_{31}$, $-NR_{30}C(S)OR_{31}$, $-NR_{30}C(NR_{32})OR_{31}$, $-S(O)_hR_{30}$, $-OS(O)_pR_{30}$, $-NR_{30}S(O)_pR_{30}$, $-S(O)_pNR_{33}R_{29}$, $-OS(O)_pNR_{33}R_{29}$, and $-NR_{30}S(O)_pNR_{33}R_{29}$.

In some embodiments, exemplary substituents for an alkyl, alkylene, alkenyl, alkynyl, cycloalkyl and cycloalkenyl, including each of $R_{14}$ and $R_{15}$ of formula (Ia) and (I), each of $R_{16}$ and $R_{17}$ of formula (II)-(IV), each of $R_{22}$ and $R_{23}$ of formula (V), each R of CRR for $X_1$ and $X_2$ of formulas (III) and (IV), and each R of CR for Z of Formula (V), include a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, a 3-8 membered heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-6 membered heteroaryl, a lower aralkyl (such as benzyl, which is optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a lower heteroaralkyl, a lower haloalkyl, $-C(O)NR_{33}R_{29}$, $-C(S)NR_{33}R_{29}$, $-NR_{30}C(O)R_{31}$, $-NR_{30}C(S)R_{31}$, halo, $-OR_{30}$, $-SR_{30}$ cyano, nitro, haloalkoxy, $-C(O)R_{30}$, $-C(S)R_{30}$, $-NR_{33}R_{29}$, $-C(O)OR_{30}$, $-C(S)OR_{30}$, $-OC(O)R_{30}$, $-OC(S)R_{30}$, $-OC(NR_{32})R_{30}$ and $-NR_{30}C(O)NR_{33}R_{29}$. Alternatively, the exemplary substituents include a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), benzyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a lower haloalkyl, $-C(O)NR_{33}R_{29}$, $-NR_{30}C(O)R_{31}$, halo, $-OR_{30}$, $-SR_{30}$, cyano, nitro, haloalkoxy, $-C(O)R_{30}$, $-NR_{33}R_{29}$, $-C(O)OR_{30}$ and $-OC(O)R_{30}$. Alternatively, the exemplary substituents include lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH)phenyl (optionally substituted with one or more substituents selected from the group consisting of lower alkyl, halo, cyano, nitro, amino, mono (lower alkyl)amino, di(lower alkyl)amino, lower alkoxy, lower haloalkoxy and —OH), benzyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), lower alkoxy, lower haloalkyl, (lower alkoxy)carbonyl, lower alkylcarbonyl, lower alkylcarboxy, cyano, nitro, lower haloalkoxy, amino, mono(lower alkyl) amino, di(lower alkyl)amino and —OH. Alternatively, the exemplary substituents include lower alkyl; phenyl, benzyl, lower alkoxy, lower haloalkyl, (lower alkoxy)carbonyl, lower alkylcarbonyl, lower alkylcarboxy, cyano, nitro, lower haloalkoxy, amino, mono(lower alkyl)amino, di(lower alkyl) amino and —OH.

In some specific embodiments, exemplary substituents for R represented by each NR of formulas (III)-(V), independently, include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, an alkoxy and a haloalkoxy. Alternatively, the exemplary substituents include an optionally substituted lower alkyl, an optionally substituted lower alkenyl, an optionally substituted lower alkynyl, an optionally substituted C3-C8 cycloalkyl, an optionally substituted C3-C8 cycloalkenyl, an optionally substituted heteroaryl C3-C8 heterocyclyl, an optionally substituted C6-C14 aryl, an optionally substituted C5-C6 heteroaryl, an optionally substituted aralkyl and a heteroaralkyl. Alternatively, the exemplary substituents include an optionally substituted lower alkyl, an optionally substituted lower alkenyl, an optionally substituted lower alkynyl, an optionally substituted C6-C14 aryl and an optionally substituted aralkyl. Each of the optionally substituted alkyl, alkenyl, alkynyl, cycloalkyl and cycloalkenyl is independently optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH. Each of the optionally substituted heterocyclyl, aryl, heteroaryl, and aralkyl, and heteroaralkyl is optionally substituted with one or more substituents selected from the group consisting of lower alkyl, halo, cyano, nitro, amino, mono(lower alkyl)amino, di(lower alkyl)amino, lower alkoxy, lower haloalkoxy and —OH.

In some more specific embodiments, exemplary substituents for R represented by each NR of formulas (III)-(V), independently, include a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH) and a lower aralkyl (such as benzyl, which is optionally substituted with one or more substituents selected from the group consisting of lower alkyl, halo, cyano, nitro, amino, mono(lower alkyl)amino, di(lower alkyl)amino, lower alkoxy, lower haloalkoxy and —OH). Alternatively, the exemplary substituents include a lower alkyl optionally substituted with one or more substituents selected from the group consisting of phenyl, benzyl, halo, cyano, nitro, amino, monoalkylamino, dialkylamino, alkoxy, haloalkoxy and —OH).

In some specific embodiments, exemplary substituents for each of the optionally substituted aryl and the optionally substituted heteroaryl groups represented by Q of formula (I), including rings A1-L1, include an alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), an alkenyl, an alkynyl, a C3-C8 cycloalkyl, a C3-C8 cycloalkenyl, a C3-C8 heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), an aralkyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a heteroaralkyl, a haloalkyl, halo, CN, —C(O)$R_{30}$, —C(S)$R_{30}$, —C(N$R_{33}$)$R_{29}$, —O$R_{30}$, —N$R_{33}R_{29}$, —S$R_{30}$, —OC(O)$R_{30}$, —N$R_{30}$C(O)$R_{31}$ and N$R_{30}$C(N$R_{33}$)$R_{29}$. Alternatively, the exemplary substituents include a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), a lower alkenyl, a lower alkynyl, a lower aralkyl (such as benzyl, which is optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a lower haloalkyl, halo, CN, —C(O)$R_{30}$, —O$R_{30}$, —N$R_{33}R_{29}$, —S$R_{30}$, —OC(O)$R_{30}$ and —N$R_{30}$C(O)$R_{31}$. Alternatively, the exemplary substituents include a lower alkyl (optionally substituted with one or more substituents selected from the group consisting of phenyl, benzyl; halo, cyano, nitro, amino, mono(lower alkyl) amino, di(lower alkyl)amino, lower alkoxy, lower haloalkoxy and —OH), a lower alkenyl, a lower alkynyl, phenyl, benzyl, a lower haloalkyl, halo, CN, —C(O)$R_{30}$, —O$R_{30}$, —N$R_{33}R_{29}$, —S$R_{30}$, —OC(O)$R_{30}$ and —N$R_{30}$C(O)$R_{31}$. Alternatively, the exemplary substituents include lower alkyl, lower alkoxy, lower haloalkyl, (lower alkoxy)carbonyl, lower alkylcarbonyl, lower alkylcarboxy, cyano, nitro, lower haloalkoxy, amino, mono(lower alkyl)amino, di(lower alkyl) amino and —OH.

$R_{33}$ and $R_{29}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{33}$ and $R_{29}$ taken together with the nitrogen to which they are attached form an optionally substituted heterocyclyl or optionally substituted heteroaryl.

$R_{30}$ and $R_{31}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; and $R_{32}$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, —C(O)$R_{30}$, —C(O)N$R_{33}R_{29}$, —S(O)$_p$$R_{30}$, or —S(O)$_p$N$R_{33}R_{29}$.

p is 1 or 2 h is 0, 1 or 2.

In some embodiments, $R_{33}$ and $R_{29}$, for each occurrence are, independently, H, an alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), an alkenyl, an alkynyl, a C3-C8 cycloalkyl, a C3-C8 cycloalkenyl, a 3-8 membered heterocyclyl, a C6-C14 aryl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-14 membered heteroaryl, an aralkyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a heteroaralkyl; or $R_{33}$ and $R_{29}$ taken together with the nitrogen to which they are attached form a 3-8 membered heterocyclyl or 5-6 membered heteroaryl; $R_{30}$ and $R_{31}$ for each occurrence are, independently, H, an alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), an alkenyl, an alkynyl, a C3-C8 cycloalkyl, a C3-C8 cycloalkenyl, a 3-8 membered heterocyclyl, a C6-C14 aryl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-14 membered heteroaryl, an aralkyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a heteroaralkyl; and $R_{32}$, for each occurrence is, independently, H, an alkyl (optionally substituted with one or more substituents selected from the group consisting of phenyl, benzyl, halo, cyano, nitro, amino, mono(lower alkyl) amino, di(lower alkyl)amino, lower alkoxy, lower haloalkoxy and —OH), an alkenyl, an alkynyl, a C3-C8 cycloalkyl, a C3-C8 cycloalkenyl, a 3-8 membered heterocyclyl, a C6-C14 aryl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-14 membered heteroaryl, an aralkyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a heteroaralkyl, —C(O)$R_{30}$, —C(O)N$R_{33}R_{29}$, —S(O)$_p R_{30}$, or —S(O)$_p$N$R_{33}R_{29}$.

In some embodiments, $R_{33}$ and $R_{29}$, for each occurrence are, independently, H, a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, a 3-6 membered heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-6 membered heteroaryl, a lower aralkyl (such as benzyl, and optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a lower heteroaralkyl, or $R_{33}$ and $R_{29}$ taken together with the nitrogen to which they are attached form a 3-6 membered heterocyclyl or a 5-6 membered heteroaryl; $R_{30}$ and $R_{31}$ for each occurrence are, independently, H, a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, a 3-6 membered heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-6 membered heteroaryl, a lower aralkyl (such as benzyl, and (optionally substituted with one or more substituents selected from the group consisting of lower alkyl, halo, cyano, nitro, amino, mono(lower alkyl) amino, di(lower alkyl)amino, lower alkoxy, lower haloalkoxy and —OH), or a lower heteroaralkyl; and $R_{32}$, for each occurrence is, independently, H, a lower alkyl (optionally substituted with one or more substituents selected from the group consisting of lower alkyl, halo, cyano, nitro, amino, mono (lower alkyl)amino, di(lower alkyl)amino, lower alkoxy, lower haloalkoxy and —OH), a lower alkenyl, a lower alkynyl, a C3-C8 cycloalkyl, a C3-C8 cycloalkenyl, a 3-6 membered heterocyclyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a 5-6 membered heteroaryl, a lower aralkyl (such as benzyl, and optionally substituted with one or more substituents selected from the group consisting of lower alkyl, halo; cyano, nitro, amino, mono(lower alkyl)amino, di(lower alkyl)amino, lower alkoxy, lower haloalkoxy and —OH), or a lower heteroaralkyl, —C(O)$R_{30}$, —C(O)N$R_{33}R_{29}$, —S(O)$_p R_{30}$, or —S(O)$_p$N$R_{33}R_{29}$.

In some embodiments, $R_{33}$ and $R_{29}$, for each occurrence are, independently, H, a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), a lower alkenyl, a lower alkynyl, a C3-C6 cycloalkyl, a C3-C6 cycloalkenyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a lower aralkyl (such as benzyl, and optionally substituted with one or more substituents selected from the group consisting of lower alkyl, halo, cyano, nitro, amino, mono(lower alkyl)amino, di(lower alkyl)amino, lower alkoxy, lower haloalkoxy and —OH); or $R_{33}$ and $R_{29}$ taken together with the nitrogen to which they are attached form a 5-6 membered heterocyclyl or a 5-6 membered heteroaryl; $R_{30}$ and $R_{31}$ for each occurrence are, independently, H, a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), a lower alkenyl, a lower alkynyl, a C3-C6 cycloalkyl, a C3-C6 cycloalkenyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or a lower aralkyl (such as benzyl, and optionally substituted with one or more substituents selected from the group consisting of lower alkyl, halo, cyano, nitro; amino, mono(lower alkyl)amino, di(lower alkyl)amino, lower alkoxy, lower haloalkoxy and —OH); and $R_{32}$, for each occurrence is, independently, H, a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, a C3-C6 cycloalkyl, a C3-C6 cycloalkenyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), a lower aralkyl (such as benzyl, and optionally substituted with one or more substituents selected from the group consisting of lower alkyl, halo, cyano, nitro, amino, mono (lower alkyl)amino, di(lower alkyl)amino, lower alkoxy, lower haloalkoxy and —OH), —C(O)$R_{30}$, —C(O)$NR_{33}R_{29}$, —S(O)$_p R_{30}$, or —S(O)$NR_{33}R_{29}$.

In some embodiments, $R_{33}$ and $R_{29}$, for each occurrence are, independently, H, a lower alkyl (optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH), a lower alkenyl, a lower alkynyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH) or benzyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH); or $R_{33}$ and $R_{29}$ taken together with the nitrogen to which they are attached form a 5-6 membered heterocyclyl or a 5-6 membered heteroaryl; $R_{30}$ and $R_{31}$ for each occurrence are, independently, H, a lower alkyl (optionally substituted with one or more substituents selected from the group consisting of phenyl, benzyl, halo, cyano, nitro, amino, mono(lower alkyl) amino, di(lower alkyl)amino, lower alkoxy, lower haloalkoxy and —OH), a lower alkenyl, a lower alkynyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or benzyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH); and $R_{32}$, for each occurrence is, independently, H, a lower alkyl (optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH), a lower alkenyl, a lower alkynyl, phenyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), or benzyl (optionally substituted with one or more substituents selected from the group consisting of lower alkyl, halo, cyano, nitro, amino, mono(lower alkyl)amino, di(lower alkyl)amino, lower alkoxy, lower haloalkoxy and —OH), —C(O)$R_{30}$, —C(O)$NR_{33}R_{29}$, —S(O)$_p R_{30}$, or —S(O)$_p NR_{33}R_{29}$.

In some embodiments, $R_{33}$ and $R_{29}$, for each occurrence are, independently, H, a lower alkyl, a lower haloalkyl, a lower alkenyl, a lower alkynyl, phenyl or benzyl; or $R_{33}$ and $R_{29}$ taken together with the nitrogen to which they are attached form a 5-6 membered heterocyclyl or a 5-6 membered heteroaryl; $R_{30}$ and $R_{31}$ for each occurrence are, independently, H, a lower alkyl, a lower haloalkyl, a lower alkenyl, a lower alkynyl, phenyl, or benzyl; and $R_{32}$, for each occurrence is, independently, H, a lower alkyl, a lower haloalkyl, a lower alkenyl, a lower alkynyl, phenyl, or benzyl, —C(O)$R_{30}$, —C(O)$NR_{33}R_{29}$, —S(O)$_p R_{30}$, or —S(O)$_p NR_{33}R_{29}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "lower" refers to a group having up to four carbon atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively. A "lower aralkyl" refers to an aryl group that is attached to another group by a ($C_1$-$C_4$)alkylene. A "lower heteroaralkyl" refers to a heteroaryl group that is attached to another group by a ($C_1$-$C_4$)alkylene.

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one ore more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxycarbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

As used herein, the term "compound(s) of this invention" and similar terms refers to a compound of formula (I) through (V) and Table 1, or a pharmaceutically acceptable salt, solvate, clathrate, hydrate, polymorph or prodrug thereof, and also include protected derivatives thereof.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, he term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I) through (V) and Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I) through (V), and Table 1, that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "Hsp70" includes each member of the family of heat shock proteins having a mass of about 70-kiloDaltons, including forms such as constituitive, cognate, cell-specific, glucose-regulated, inducible, etc. Examples of specific Hsp70 proteins include hsp70, hsp70hom; hsc70; Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. Membrane-bound Hsp70 In humans, the Hsp70 family encompasses at least 11 genes encoding a group of highly related proteins. See, for example, Tavaria, et al., Cell Stress Chaperones, 1996; 1(1):23-28; Todryk, et al., immunology. 2003, 110(1): 1-9; and Georgopoulos and Welch, Annu Rev Cell Biol. 1993; 9:601-634; the entire teachings of these documents are incorporated herein by reference.

As used herein, an "Hsp70-responsive disorder" is a medical condition wherein stressed cells can be treated by increased Hsp70 expression. Such disorders can be caused by a wide variety of cellular stressors, including, but not limited to 'Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; autoimmune disease; infection (bacterial, viral, fungal, or parasitic); and the like.

In some embodiments, the Hsp70-responsive disorder is a neurodegenerative disorder. As used herein, a neurodegenerative disorder involves degradation of neurons such as cereberal, spinal, and peripheral neurons (e.g., at neuromuscular junctions), more typically degradation of cerebral and spinal neurons, or in preferred embodiments, degradation of cerebral neurons. Neurodegenerative disorders can include Alzheimers' disease; Huntington's disease; Parkinson's disease; spinal/bulbar muscular atrophy and other neuromuscular atrophies; and familial amyotrophic lateral sclerosis or other diseases associated with superoxide dismutase (SOD) mutations. Neurodegenerative disorders can also include degradation of neurons caused by ischemia, seizure, thermal stress, radiation, toxin exposure, infection, injury, and the like.

In some embodiments, the Hsp70-responsive disorder is a disorder of protein aggregation/misfolding, such as Alzheimers' disease; Huntington's disease; Parkinson's disease; spongiform encephalopathies; and the like.

In another embodiment the Hsp70 responsive disorder is a treatment or condition which causes or may cause nerve damage. The compounds for use in the methods of the present invention can be used to reduce or prevent (inhibit the onset of) nerve damage (i.e., provide neuroprotection) in a subject i) suffering from a condition which causes or may cause nerve damage or ii) receiving treatment which causes or may cause nerve damage. In one aspect, the treatment which causes or may cause nerve damage is radiation therapy. In another aspect, the treatment is chemotherapy. In one aspect, the chemotherapy comprises administering an antimitotic agent (e.g. vincristine, vinorelbine, paclitaxel, or a paclitaxel analog). In one aspect, the chemotherapy comprises administering paclitaxel. In another aspect, the chemotherapy comprises administering a platinum derivative (e.g. cisplatinum, carboplatin, or oxaliplatin). In certain embodiments, the compounds for use in the methods of the present invention can be administered simultaneously as a combination therapy with the treatment which causes or may cause nerve damage. In other embodiments the compounds for use in the methods of the present invention can be administered before or after the treatment which causes may cause nerve damage. In certain embodiments the compounds for use in the methods of the present invention can be administered between 30 minutes and 12 hours, between 1 hour and 6 before or after the treatment which causes or may cause nerve damage.

Nerve damage may be caused by a number of treatments including, but not limited to, radiation therapy; chemotherapy, e.g. cisplatinum, carboplatin, oxaliplatin, vincristine, vinblastine, vinorelbine, vindesine, ifosfamide, methotrexate, cladribine, altretamine, fludarabine, procarbazine, thiotepa, teniposide, arsenic trioxide, alemtuzumab, capecitabine, dacarbazine, denileukin diftitox, interferon alpha, liposomal daunorubicin, tretinoin, etoposide/VP-16, cytarabine, hexamethylmelamine, suramin, paclitaxel, docetaxel, gemcitibine, thalidomide, and bortezomib; heart or blood pressure medications, e.g. amiodarone, hydralazine, digoxin, and perhxiline; medications to fight infection, e.g. metronidazole, nitrofurantoin, thalidomide, and INH; medications to treat skin conditions, e g dapsone; anticonvulsants, e.g. phenytoin; anti-alcohol medications, e.g. disulfiram; HIV medications, e g. Zidovudine, didanonsine, stavudine, zalcitabine, ritonavir, d4T, ddC, ddl, and amprenavir; cholesterol medications, e.g. lovastatin, pravastatin, indapamid, simvastatin, fluvastatin, atorvastatin, cerivastatin, and gemfibrozil; antirheumatics, e.g. chloroquine, cholchicine, organic gold, and penicillamine; nitrous oxide; lithium; and ergots.

In some embodiments, the Hsp70-responsive disorder is ischemia: Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like. In one preferred embodiment, the Hsp70-responsive disorder is cerebral or spinal ischemia. In another preferred embodiment, the Hsp70-responsive disorder is cardiac ischemia.

In various embodiments, the Hsp70-responsive disorder is seizure, e.g., epileptic seizure, injury-induced seizure, chemically-induced seizure, and the like.

In some embodiments, the Hsp70-responsive disorder is due to thermal stress. Thermal stress includes hyperthermia (e.g., from fever, heat stroke, burns, and the like) and hypothermia. In a preferred embodiment the disorder is hyperthermia. In another preferred embodiment, the Hsp70-responsive disorder is burn trauma.

In preferred embodiments, the Hsp70-responsive disorder is atherosclerosis.

In various embodiments, the Hsp70-responsive disorder is radiation damage, e.g., due to visible light, ultraviolet light, microwaves, cosmic rays, alpha radiation, beta radiation, gamma radiation, X-rays, and the like. For example, the damage could be radiation damage to non-cancerous tissue in a subject treated for cancer by radiation therapy. In a preferred embodiment, the Hsp70-responsive disorder is radiation damage from visible light or ultraviolet light.

In various embodiments, the Hsp70-responsive disorder is mechanical injury, e.g., trauma from surgery, accidents, certain disease conditions (e.g., pressure damage in glaucoma) and the like. In a preferred embodiment, the Hsp70-responsive disorder is cerebral or spinal trauma. In another preferred embodiment, the Hsp70-responsive disorder is glaucoma (leading to pressure damage to retinal ganglions).

In various embodiments, the Hsp70-responsive disorder is exposure to a toxin. In preferred embodiments, the Hsp70-responsive disorder is exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Certain compounds of the invention also increase Natural Killer (NK) cell activity. As used herein, a "NK cell-responsive disorder" is a medical condition which is improved by an increased in NK cell activity. For example, a subject with a NK cell-responsive disorder may need immune system augmentation because of infection or the possibility thereof. In some embodiments, such a subject can have an infection (or has been exposed to an infectious environment where pathogens are present, e.g., in a hospital) the symptoms of which may be alleviated by the methods disclosed herein. For example, a subject in need of treatment can have an infection (bacterial, viral, fungal, or parasitical (protozoal) for which the disclosed methods of activating NK cells can be a treatment.

In some embodiments, a subject having an NK cell-responsive disorder has an immunodeficiency. Such a subject is in need of or can benefit from prophylactic therapy, for example, a subject that has incomplete, damaged or otherwise compromised defenses against infection, or is subject to an infective environment, or the like. For example, a subject can be in an infectious environment where pathogens are present, e.g., in a hospital; can have an open wound or burn injury; can have an inherited or acquired immune deficiency (e.g., severe combined immunodeficiency or "bubble boy" syndrome, variable immunodeficiency syndrome acquired immune deficiency syndrome (AIDS), or the like); can have a depressed immune system due to physical condition, age, toxin exposure, drug effect (immunosuppressants, e.g., in a transplant recipient) or side effect (e.g., due to an anticancer agent); or the like.

In some embodiments, NK cell activity can be increased in subjects that have decreased or deficient NK cell activity, in conditions such as chronic fatigue syndrome (chronic fatigue immune dysfunction syndrome) or Epstein-Barr virus infection, post viral fatigue syndrome, post-transplantation syndrome (especially allogeneic transplants) or host-graft disease, exposure to drugs such as anticancer agents or nitric oxide synthase inhibitors, natural aging, and various immunodeficient conditions such as severe combined immunodeficiency, variable immunodeficiency syndrome, and the like.

In some embodiments, a subject having an NK cell-responsive disorder is in need of treatment for bacteremia. Bacteremia is the condition of bacterial infection in the bloodstream. Septic shock includes serious localized or bacteremic infection accompanied by systemic inflammation, in other words sepsis with hypoperfusion and hypotension refractory to fluid therapy. Sepsis, or systemic inflammatory response syndrome, includes various severe conditions such as infections, pancreatitis, burns, trauma) that can cause acute inflammation. Septic shock is typically related to infections by gram-negative organisms, staphylococci, or meningococci. Septic shock can be characterized by acute circulatory failure, typically with hypotension, and multiorgan failure.

Transient bacteremia can be caused by surgical or trauma wounds. Gram-negative bacteremia can be intermittent and opportunistic; although it may have no effect on a healthy person, it may be seriously important in immunocompromised patients with debilitating underlying diseases, after chemotherapy, and in settings of malnutrition. The infection can typically be in the lungs, in the genitourinary (GU) or gastrointestinal (GI) tract, or in soft tissues, e.g., skin in patients with decubitus ulcer, oral ulcers in patients at risk, and patients with valvular heart disease, prosthetic heart valves, or other implanted prostheses.

Typically, gram-negative bacteremia can manifest in chronically ill and immunocompromised patients. Also in such patients, bloodstream infections can be caused by aerobic bacilli, anaerobes, and fungi. Bacteroides can lead to abdominal and pelvic infective complications, especially in females. Transient or sustained bacteremia can typically result in metastatic infection of the meninges or serous cavities, such as the pericardium or larger joints. *Enterococcus, staphylococcus*, or fungus can lead to endocarditis, but is less common with gram-negative bacteremia. Staphylococcal bacteremia can be typical of IV drug users, and can be a typical cause of gram-positive bacterial endocarditis.

The incidence of systemic fungal infections has undergone a significant increase, particularly in humans, due in part to increases in the number of subjects with compromised immune systems, for example, the elderly, AIDS patients, patients undergoing chemotherapy, burn patients, patients with diabetic ketoacidosis, and transplant patients on immunosuppressive drugs. A study found that about 40% of deaths from infections acquired during hospitalization were due to mycoses; see Sternberg et al, *Science*, Vol. 266, (1994), pp. 1632-1634, the entire teachings of which are incorporated herein by reference.

In various embodiments, the subject having an NK cell-responsive disorder can be in need of treatment for a fungal infection, such as a pathogenic dermatophyte, a pathogenic filamentous fungus, and/or a pathogenic non-filamentous fungus, e.g., a yeast, or the like. Pathogenic dermatophytes can include, e.g., species of the genera *Trichophyton, Tinea, Microsporum; Epidermophyton*, or the like. Pathogenic filamentous fungus can include, e.g., species of genera such as *Aspergillus, Histoplasma, Cryptococcus, Microsporum*, or the like. Pathogenic non-filamentous fungus, e.g., yeasts, can include, for example, species of the genera *Candida, Malassezia, Trichosporon, Rhodotorula, Torulopsis, Blastomyces, Paracoccidioides, Coccidioides*, or the like. In various embodiments, the subject can be treated for a fungal infection from a species of the genera *Aspergillus* or *Trichophyton*. Species of *Trichophyton* can include, for example, *Trichophyton mentagrophytes, Trichophyton rubrum, Trichophyton schoenleinii, Trichophyton tonsurans, Trichophyton verrucosum*, and *Trichophyton violaceum*. Species of *Aspergillus* can include, for example, *Aspergillus fumigatus, Aspergillus flavus, Aspergillus niger, Aspergillus amstelodami, Aspergillus candidus, Aspergillus carneus, Aspergillus nidulans, A. oryzae, Aspergillus restrictus, Aspergillus sydowi, Aspergillus terreus, Aspergillus ustus, Aspergillus versicolor, Aspergillus caesiellus, Aspergillus clavatus, Aspergillus avenaceus*, and *Aspergillus deflectus*. In some embodiments, the subject can be treated for a fungal infection from a pathogenic dermatophyte, e.g., *Trichophyton* (e.g., *Trichophyton rubrum*), *Tinea, Microsporum*, or *Epidermophyton*; or *Cryptococcus* (e.g., *Cryptococcus neoformans*) *Candida* (e.g., *Candida albicans*), *Paracoccidioides* (e.g., *Paracoccidioides brasiliensis*), or *Coccidioides* (e.g., *Coccidioides immitis*). In particular embodiments, the subject can be treated for a fungal infection from *Trichophyton rubrum, Cryptococcus neoformans, Candida albicans, Paracoccidioides brasiliensis*, or *Coccidioides immitis*.

Thus, in various embodiments, a subject can have an infection caused by a fungus selected from the genera *Trichophyton, Tinea, Microsporum, Epidermophyton, Aspergillus, Histoplasma, Cryptococcus, Microsporum, Candida, Malassezia, Trichosporon, Rhodotorula, Torulopsis, Blastomyces, Paracoccidioides*, and *Coccidioides*. In some embodiments, the subject can have an infection caused by a fungus selected from the genera *Trichophyton, Tinea, Microsporum, Epidermophyton; Cryptococcus, Candida, Paracoccidioides*, and *Coccidioides*. In certain embodiments, the subject can have an infection caused by a fungus selected from *Trichophyton rubrum, Cryptococcus neoformans, Candida albicans, Paracoccidioides brasiliensis*, and *Coccidioides immitis*.

In various embodiments, the subject having an NK cell-responsive disorder can be in need of treatment for a bacterial infection caused, for example, by a bacteria of a genus selected from *Allochromatium, Acinetobacter, Bacillus, Campylobacter, Chlamydia, Chlamydophila, Clostridium, Citrobacter, Escherichia, Enterobacter, Enterococcus, Francisella, Haemophilus, Helicobacter, Klebsiella, Listeria, Moraxella, Mycobacterium, Micrococcus, Neisseria, Proteus, Pseudomonas, Salmonella, Serratia, Shigella, Stenotrophomonas, Staphyloccocus, Streptococcus, Synechococcus, Vibrio*, and *Yersina*; or anerobic bacterial genera such as *Peptostreptococci, Porphyromonas, Actinomyces, Clostridium, Bacteroides, Prevotella, Anaerobiospirillum, Fusobacterium*, and *Bilophila*. In some embodiments, the subject having an NK cell-responsive disorder can be in need of treatment for a bacterial infection from *Allochromatium vinosum, Acinetobacter baumanii, Bacillus anthracis, Campylobacter jejuni, Chlamydia trachomatis, Chlamydia pneumoniae, Clostridium* spp., *Citrobacter* spp., *Escherichia coli, Enterobacter* spp., *Enterococcus faecalis, Enterococcus faecium, Francisella tularensis, Haemophilus influenzae, Helicobacter pylori, Klebsiella* spp., *Listeria monocytogenes, Moraxella catarrhalis, Mycobacterium tuberculosis, Neisseria meningitidis, Neisseria gonorrhoeae, Proteus mirabilis, Proteus vulgaris, Pseudomonas aeruginosa, Salmonella* spp., *Serratia* spp., *Shigella* spp., *Stenotrophomonas maltophilia, Staphyloccocus aureus, Staphyloccocus epidermidis, Streptococcus pneumoniae, Streptococcus pyogenes, Streptococcus agalactiae, Yersina pestis*, and *Yersina enterocolitica*, or the like; or *Peptostreptococci asaccharolyticus, Peptostreptococci magnus, Peptostreptococci micros, Peptostreptococci prevotii, Porphyromonas asaccharolytica, Porphyromonas canoris, Porphyromonas gingivalis, Porphyromonas macaccae, Actinomyces israelii, Actinomyces odontolyticus, Clostridium innocuum, Clostridium clostridioforme, Clostridium difficile, Bacteroides tectum, Bacteroides ureolyticus, Bacteroides gracilis* (*Campylobacter gracilis*), *Prevotella intermedia, Prevotella heparinolytica, Prevotella oris-buccae, Prevotella bivia, Prevotella melaninogenica, Fusobacterium naviforme, Fusobacterium necrophorum, Fusobacterium varium, Fusobacterium ulcerans, Fusobacterium russii, Bilophila wadsworthia, Haemophilus ducreyi; Calymmatobacterium granulomatis*, or the like.

It is believed that compounds of the invention can be particularly useful for treating a subject with an intracellular infection. It is generally believed in the art that NK cells are particularly effective against intracellular infections. Intracellular infections are those wherein a portion of the infecting pathogen resides within cells of the subject.

For example, intracellular infections can be caused by one or more bacteria selected from: *Ehrlichia* (e.g., obligate, intracellular bacteria that can appear as small cytoplasmic inclusions in lymphocytes and neutrophils such as *Ehrlichia sennetsu, Ehrlichia canis, Ehrlichia chaffeensis, Ehrlichia phagocytophilia*, or the like); *Listeria* (e.g., *Listeria monocytogenes*); *Legionella* (e.g., *Legionella pneumophila*); *Rickettsiae* (e.g., *Rickettsiae prowazekii, Rickettsiae typhi* (*Rickettsiae mooseri*), *Rickettsiae rickettsii, Rickettsiae tsutsugamushi, Rickettsiae sibirica; Rickettsiae australis; Rickettsiae conorii; Rickettsiae akari; Rickettsiae burnetii*); *Chlamydia* (e.g., *Chlamydia psittaci; Chlamydia pneumoniae; Chlamydia trachomatis*, or the like); *Mycobacterium* (*Mycobacterium tuberculosis; Mycobacterium marinum; Mycobacterium Avium* Complex; *Mycobacterium bovis; Mycobacterium scrofulaceum; Mycobacterium ulcerans; Mycobacterium leprae* (Leprosy, Hansen's *Bacillus*)); *Brucella* (e.g., *Brucella melitensis; Brucella abortus; Brucella suis; Brucella canis*); genus *Coxiella* (e.g., *Coxiella burnetii*); or the like. Thus, in some embodiments, the subject can have an intracellular bacterial infection caused by a bacterium selected from the genera *Ehrlichia; Listeria; Legionella; Rickettsiae; Chlamydia; Mycobacterium; Brucella*; and *Coxiella*.

In various embodiments, the subject having an NK cell-responsive disorder can be in need of treatment for a bacterial infection from one or more upper respiratory tract bacteria. Examples of upper respiratory tract bacteria include those belonging genera such as *Legionella, Pseudomonas*, and the like. In some embodiments, the bacteria can be *Pseudomonas aeruginosa*. In particular embodiments, the bacteria can be *Legionella pneumophila* (e.g., including serogroups 1, 2, 3, 4, 5, 6, 7, 8, and the like), *Legionella dumoffli, Legionella longbeacheae, Legionella micdadei, Legionella oakridgensis, Legionella feeleri, Legionella anisa, Legionella sainthelensi, Legionella bozemanii, Legionella gormanii, Legionella wadsworthii, Legionella jordanis*, or *Legionella gormanii*.

In some embodiments, the subject having an NK cell-responsive disorder can be in need of treatment for a bacterial infection from one that causes acute bacterial exacerbation of chronic bronchitis (ABECB) in the subject. Typically, ABECB can be caused by *Streptococcus pneumoniae, Haemophilus influenzae, Haemophilus parainfluenzae*, or *Moraxella catarrhalis*.

In some embodiments, the subject having an NK cell-responsive disorder can be in need of treatment for a bacterial infection from one that causes acute community acquired pneumonia (CAP) in the subject. Typically, CAP can be caused by *Streptococcus pneumoniae, Haemophilus influenzae, Moraxella catarrhalis, Mycoplasma pneumoniae, Chlamydia pneumoniae*, or *Klebsiella pneumoniae*. In a particular embodiment, the CAP can be caused by drug resistant bacteria, e.g., a multi-drug resistant strain of *Streptococcus pneumoniae*.

In various embodiments, the subject having an NK cell-responsive disorder can be in need of treatment for a bacterial infection from *Streptococcus pneumoniae, Haemophilus influenzae, Haemophilus parainfluenzae, Moraxella catarrhalis, Mycoplasma pneumoniae, Chlamydia pneumoniae, Klebsiella pneumoniae, Staphylococcus aureus, Streptococcus pyogenes, Acinetobacter lwoffi, Klebsiella oxytoca, Legionella pneumophila*, or *Proteus vulgaris*.

In various embodiments, the subject having an NK cell-responsive disorder can be in need of treatment for a bacterial infection from maxillary sinus pathogenic bacteria. As used herein, maxillary sinus pathogenic bacteria is a bacterial strain isolated from acute or chronic maxillary sinusitis, or, for example, a maxillary sinus isolate of *Staphylococcus aureus, Streptococcus pneumoniae, Haemophilus* spp., *Moraxella catarrhalis*, an anaerobic strain of non-fermentative Gram negative bacilli, *Neisseria meningitides* or β-haemolytic *Streptococcus*. In various embodiments, maxillary sinus pathogenic bacteria can include a bacterial strain isolated from acute or chronic maxillary sinusitis; a maxillary sinus isolate of *Staphylococcus aureus, Streptococcus pneumoniae, Haemophilus* spp., *Moraxella catarrhalis*, an anaerobic strain of non-fermentative Gram negative bacilli, *Neisseria meningitidis*, β-haemolytic *Streptococcus, Haemophilus influenzae*, an Enterobacteriaceae, a non-fermentative Gram negative bacilli, *Streptococcus pneumoniae, Streptococcus pyogenes*, a methicillin-resistant *Staphylococcus* spp., *Legionella pneumophila, Mycoplasma* spp and *Chlamydia* spp., *Haemophilus influenzae, Haemophilus parainfluenzae, Peptostreptococcus, Bacteroides* spp., and *Bacteroides urealyticus*.

In various embodiments, the subject having an NK cell-responsive disorder can be in need of treatment for a bacterial infection that causes a urinary tract infection (UTI) in the subject. Examples of UTIs include urethritis, cystitis, prostatitis, pyelonephritis (acute, chronic, and xanthogranulomatous), and hematogenous UTI (e.g., from bacteremia with virulent bacilli such as *Salmonella, Staphylococcus aureus*, and the like). Typically, UTIs can be caused by gram-negative aerobic bacteria, e.g., *Escherichia* (e.g., *Escherichia coli*), *Klebsiella, Proteus, Enterobacter, Pseudomonas*, and *Serratia*; gram-negative anaerobic bacteria; gram-positive bacteria, e.g., Enterococci (e.g., *Enterococcus faecalis*) and *Staphylococcus* sp (e.g., *Staphylococcus saprophyticus, Staphylococcus aureus*, and the like); *Mycobacterium tuberculosis*; and sexually transmitted bacterial infections (e.g., *Chlamydia trachomatis, Neisseria gonorrhoeae*, and the like).

In certain embodiments, the subject having an NK cell-responsive disorder can be in need of treatment for infections from microorganisms that cause sexually transmitted diseases, for example, *Treponema pallidum; Trichomonas vaginalis; Candidia* (*Candida albicans*); *Neisseria gonorrhoeae; Chlamydia trachomatis; Mycoplasma genitalium, Ureaplasma urealyticum; Haemophilus ducreyi; Calymmatobacterium granulomatis* (formerly *Donovania granulomatis*); herpes simplex viruses (HSV-1 or HSV-2); human papillomavirus [HPV]; human immunodeficiency virus (HIV); various bacterial (*Shigella, Campylobacter*, or *Salmonella*), viral (hepatitis A), or parasitic (*Giardia* or amoeba, e.g., *Entamoeba dispar* (previously *Entamoeba histolytica*); or the like.

Thus, in various embodiments, the subject having an NK cell-responsive disorder can be in need of treatment for an infection resulting in upper respiratory tract bacterial infection, acute bacterial exacerbation of chronic bronchitis; acute community acquired pneumonia, maxillary sinus pathogenic bacteria; a urinary tract infection; or a sexually transmitted infection.

It is believed that the methods can be particularly effective for treating a subject with a viral infection. Thus, in various embodiments, a subject having an NK cell-responsive disorder can be in need of treatment for infection from viruses such as Picornaviruses (e.g., Polio Virus, rhinoviruses and certain echoviruses and coxsackieviruses); Parvoviridae (Human Parvovirus B 19); Hepatitis, e.g, Hepadnavirus (Hepatitis B); Papovavirus (JC Virus); Adenovirus (Human Adenovirus); Herpesvirus (e.g., Cytomegalovirus, Epstein Barr Virus (Mononucleosis), Mononucleosis-Like Syndrome, Roseola Infantum, Varicella Zoster Virus (Chicken Pox), Herpes Zoster (Shingles), Herpes Simplex Virus (Oral Herpes, Genital Herpes)), Poxvirus (Smallpox); Calicivirus (Norwalk Virus), Arbovitus (e.g., Togavirus (Rubella virus, Dengue virus), Flavivirus (Yellow Fever virus), Bunyavirus (California Encephalitis Virus), Reovirus (Rotavirus)); Coronavirus (Coronavirus); Retrovirus (Human Immunodeficiency Virus 1, Human Immunodeficiency Virus 2); Rhabdovirus (Rabies Virus), Filovirus (Marburg Virus, Ebola virus, other hemorrhagic viral diseases); Paramyxovirus (Measles Virus, Mumps Virus); Qrthomyxovirus (Influenza Virus); Arenavirus (Lassa Fever); human T-cell Lymphotrophic virus type I and II (HTLV-I, HTLV II); human papillomavirus [HPV]; or the like. Thus, in various embodiments, the subject can have an infection caused by a virus selected from Picornavirus; Parvoviridae; Hepatitis virus; Papovavirus; Adenovirus; Herpesvirus, Poxvirus; Calicivirus; Arbovirus; Coronavirus; a Retrovirus; Rhabdovirus; Paramyxovirus; Orthomyxovirus; Arenavirus; human T-cell Lymphotrophic virus; human papillomavirus; and human immunodeficiency virus.

In some embodiments, a subject having an NK cell-responsive disorder can be in need of treatment for an infection from a virus or an infection thereof such as human immunodeficiency virus-1, human immunodeficiency virus-2, Cytomegalovirus, Epstein Barr Virus, Mononucleosis-Like Syndrome, Roseola Infantum, Varicella Zoster Virus, Herpes Zoster, Herpes Simplex Virus, or hepatitis.

It is believed that the methods can be particularly effective for treating a subject with a parasitic infection. Thus, in various embodiments, a subject having an NK cell-responsive disorder can be in need of treatment for an infection from *Plasmodia* (e.g., *Plasmodia falciparum, Plasmodia vivax, Plasmodia ovale*, and *Plasmodia malariae*, typically transmitted by anopheline mosquitoes); *Leishmania* (transmitted by sandflies and caused by obligate intracellular protozoa, e.g., *Leishmania donovani, Leishmania infantum, Leishmania chagasi, Leishmania mexicana, Leishmania amazonensis, Leishmania venezuelensis, Leishmania tropica; Leishmania major; Leishmania aethiopica*; and the subgenus *Viannia, Leishmania Viannia braziliensis, Leishmania Viannia guyanensis, Leishmania Viannia panamensis*, and *Leishmania Viannia peruviana*); *Trypanosoma* (e.g., sleeping sickness caused by *Trypanosoma brucei gambiense*, and *Trypanosoma brucei rhodesiense*); amoebas of the genera *Naegleria* or *Acanthamoeba*; pathogens such as genus *Entamoeba* (*Entamoeba histolytica* and *Entamoeba dispar*); *Giardia lamblia; Cryptosporidium; Isospora; Cyclospora; Microsporidia; Ascaris lumbricoides*; infection with blood flukes of the genus *Schistosoma* (e.g.; *S. haematobium; S. mansoni; S. japonicum; S. mekongi; S. intercalatum*); Toxoplasmosis (e.g., *Toxoplasma gondii*); *Treponema pallidum; Trichomonas vaginalis*; or the like.

In some embodiments, the subject having an NK cell-responsive disorder can have an infection caused by a protozoa selected from *Toxoplasma gondii, Trypanosoma brucei gambiense, Trypanosoma brucei rhodesiense, Leishmania donovani, Leishmania infantum, Leishmania chagasi, Leishmania mexicana, Leishmania amazonensis, Leishmania venezuelensis, Leishmania tropica; Leishmania major; Leishmania aethiopica*; and the subgenus *Viannia, Leishmania Viannia braziliensis, Leishmania Viannia guyanensis, Leishmania Viannia panamensis, Leishmania Viannia peruviana, Plasmodia falciparum, Plasmodia vivax, Plasmodia ovale*, and *Plasmodia malariae*.

In the last century, antibiotics were developed that led to significant reductions in mortality. Unfortunately, widespread use has led to the rise of antibiotic resistant bacteria, e.g., methicillin resistant *Staphyloccocus aureus* (MRSA), vancomycin resistant enterococci (VRE), and penicillin-resistant *Streptococcus pneumoniae* (PRSP). Some bacteria are resistant to a range of antibiotics, e.g., strains of *Mycobacterium tuberculosis* resist isoniazid, rifampin, ethambutol, streptomycin, ethionamide, kanamycin, and rifabutin. In addition to resistance, global travel has spread relatively unknown bacteria from isolated areas to new populations. Furthermore, there is the threat of bacteria as biological weapons. These bacteria may not be easily treated with existing antibiotics.

It is believed that the compounds of the invention can be particularly effective for treating a subject for drug-resistant pathogens, for example, drug resistant bacteria, or pathogens for which no drugs are available, e.g., many viruses. Without wishing to be bound by theory, it is believed that because the compounds of the invention can act by increasing NK cell activity, and thus the NK cells can kill infective microorganisms or infected cells separately from any direct action of the compounds on the pathogen or infected cells. Thus, it is believed that the compounds of the invention can have at least one mode of action that is separate from typical anti-infective drugs such as antibiotics which can typically act directly on the bacteria themselves.

Drug resistant pathogens can be resistant to at least one and typically multiple agents, for example, drug resistant bacteria can be resistant to one antibiotic, or typically at least two antibiotics such as penicillin, Methicillin, second generation cephalosporins (e.g., cefuroxime, and the like), macrolides, tetracyclines, trimethoprim/methoxazole, vancomycin, or the like. For example, in some embodiments, a subject can be treated for bacteria selected from a strain of multiple drug resistant *Streptococcus pneumoniae* (MDRSP, previously known as penicillin resistant *Streptococcus pneumoniae*, PRSP), vancomycin resistant *Enterococcus*, methicillin resistant *Staphylococcus Aureus*, penicillin resistant *Pneumococcus*, antibiotic resistant *Salmonella*, resistant and multi-resistant *Neisseria Gonorrhea* (e.g., resistant to one, two or more of tetracycline, penicillin, fluoroquinolones, cephalosporins, ceftriaxone (Rocephin), Cefixime (Suprax), Azithromycin, or the like), and resistant and multi-resistant Tuberculosis (e.g., resistant to one, two or more of Isoniazid, Rifampin, Ethambutol, Pyrazinamide, Aminoglycoside, Capreomycin, Ciprofloxacin, Ofloxacin, gemifloxacin, Cycloserine, Ethionamide, para-aminosalicylic acid or the like).

In some embodiments, NK cell activity can be increased in subjects that have an immunodeficiency. In various embodiments, this can be due to decreased or deficient NK cell activity. In some embodiments, the immunodeficiency can be any known immunodeficiency, even those that do not directly impact NK cells. Without wishing to be bound by theory, it is believed that boosting NK cell activity can augment immune function in many immunodeficiency conditions to "make-up" at least in part, for aspects of immunodeficiency separate from those aspects directly concerned with NK cell activity.

In various embodiments, immunodeficiency disorders can include disorders with increased susceptibility to infection, for example, one or more disorders selected from: circulatory and systemic disorders (sickle cell disease, diabetes mellitus, nephrosis, varicose veins, congenital cardiac defects); obstructive disorders (ureteral or urethral stenosis, bronchial asthma, bronchiectasis, allergic rhinitis, blocked Eustachian tubes); integumentary defects (eczema, burns, skull fractures, midline sinus tracts, ciliary abnormalities); primary immunodeficiencies (X-linked agammaglobulinemia, DiGeorge anomaly, chronic granulomatous disease, C3 deficiency); secondary immunodeficiencies (malnutrition, prematurity, lymphoma, splenectomy, uremia, immunosuppressive therapy, protein-losing enteropathy, chronic viral diseases); unusual microbiologic factors (antibiotic overgrowth, chronic infections with resistant organism, continuous reinfection (contaminated water supply, infectious contact, contaminated inhalation therapy equipment)); foreign bodies, trauma (ventricular shunts, central venous catheter, artificial heart valves, urinary catheter, aspirated foreign bodies) allogeneic transplant, graft-versus-host disease, uterine dysfunction (e.g., endometriosis), or the like.

In various embodiments, immunodeficiency disorders can include for example, transient hypogammaglobulinemia of infancy, selective IgA deficiency, X-linked agammaglobulinemian (Bruton's Agammaglobulinemia; Congenital Agammaglobulinemia), common variable immunodeficiency (Acquired Agammaglobulinemia), hyper-IgM immunodeficiency, IgG subclass deficiency, chronic mucocutaneous Candidiasis, combined immunodeficiency, Wiskott-Aldrich syndrome, ataxia-telangiectasia, X-linked lyriphoproliferative syndrome, hyper-IgE syndrome (Job-Buckley Syndrome), chronic granulotomatous disease, leukocyte adhesion deficiency (MAC-1/LFA-1/CR3 deficiency), or the like.

In various embodiments, immunodeficiency disorders can include primary immunodeficiency disorders for example: B-cell (antibody) deficiencies (X-linked agammaglobulinemia; Ig deficiency with hyper-IgM (XL); IgA deficiency); IgG subclass deficiencies, Antibody deficiency with normal or elevated Igs, Immunodeficiency with theymoma, Common variable immunodeficiency, Transient hypogammaglobulinemia of infancy); T-cell (cellular) deficiencies (Predominant T-cell deficiency: DiGeorge anomaly, Chronic mucocutaneous candidiasis, Combined immunodeficiency with Igs (Nezelof syndrome), Nucleoside phosphorylase deficiency (AR), Natural killer cell deficiency, Idiopathic CD4 lymphocytopenia, Combined T- and B-cell deficiencies: Severe combined immunodeficiency (AR or XL), Adenosine deaminase deficiency (AR), Reticular dysgenesis, Bare lymphocyte syndrome, Ataxia-telangiectasia (AR), Wiskott-Aldrich syndrome (XL), Short-limbed dwarfism, XL lymphoproliferative syndrome); Phagocytic disorders (Defects of cell movement: Hyperimmunoglobulinemia E syndrome, Leukocyte adhesion defect type 1 (AR), Defects of microbicidal activity: Chronic granulomatous disease (XL or AR), Neutrophil G6PD deficiency, Myeloperoxidase deficiency (AR), Chediak-Higashi syndrome (AR)); Complement disorders (Defects of complement components: C1q deficiency, Defects of control proteins: C1 inhibitor deficiency (D1), Factor I (C3b inactivator) deficiency (ACD), Factor H deficiency (ACD), Factor D deficiency (ACD), Properdin deficiency (XL)); or the like In various embodiments, immunodeficiency disorders can include secondary immunodeficiency disorders, for example, one or more conditions selected from: Premature and newborn infants (Physiologic immunodeficiency due to immaturity of immune system); Hereditary and metabolic diseases (Chromosome abnormalities (e.g., Down syndrome), Uremia, Diabetes (i.e., complications from diabetes such as gangrene associated with peripheral circulatory and nerve dysfunction), Malnutrition, Vitamin and mineral deficiencies, Protein-losing enteropathies, Nephrotic syndrome, Myotonic dystrophy, Sickle cell disease); Immunosuppressive agents (Radiation, Immunosuppressive drugs, Corticosteroids, Anti-lymphocyte or anti-thymocyte globulin, Anti-T-cell monoclonal antibodies); Infectious diseases (Congenital rubella, Viral exanthems (e.g., measles, varicella), HIV infection, Cytomegalovirus infection, Infectious mononucleosis, Acute bacterial disease, Severe mycobacterial or fungal disease); Infiltrative and hematologic diseases (Histiocytosis, Sarcoidosis, Hodgkin's disease and lymphoma, Leukemia, Myeloma, Agranulocytosis and aplastic anemia); Surgery and trauma (Burns, Splenectomy, Anesthesia, wounds); and Miscellaneous (SLE, Chronic active hepatitis, Alcoholic cirrhosis, Aging, Anticonvulsive drugs, Graft-vs.-host disease); or the like.

In certain embodiments, the subject having an NK cell-responsive disorder can be in need of treatment for burns or wounds. Typically, such a wound or burn is a severe injury that places a significant burden on the subject's immune defenses. For example, in some embodiments, the subject is treated for a second or third degree burn covering at least about 5%, 10%, 15%, 20%, 25%, 30%, 40%, 50%, 75%, or more of the surface area of the subject's body. Also, in some embodiments, the subject is treated for a wound or wounds, e.g., an open wound of at least about 1 cm$^2$, 2 cm$^2$, 5 cm$^2$, 1.0 cm$^2$, 20 cm$^2$, 50 cm$^2$ or larger, or 1%, 2%, 3%, 4%, 5%, 10%, 15%; or more of the surface area of the subject's body; or one or more incisions penetrating the skin totaling at least 1 cm, 2 cm, 3 cm, 4 cm, 5 cm, 7 cm, 10 cm, 20 cm, 25 cm, 50 cm in length; an amputation; and the like.

In various embodiments, the subject having an NK cell-responsive disorder can have an infection caused by antibiotic resistant bacteria. In some embodiments, the subject can have an infection caused by a bacterium selected from multiple drug resistant *Streptococcus pneumoniae*, vancomycin resistant *Enterococcus*, methicillin resistant *Staphylococcus Aureus*, penicillin resistant *Pneumococcus*, antibiotic resistant *Salmonella*, resistant/multi-resistant *Neisseria Gonorrhea*, and resistant/multi-resistant Tuberculosis. In some embodiments, the subject can have a bacterial infection resistant to at least one antibiotic selected from penicillin, Methicillin, second generation cephalosporins, macrolides, tetracyclines, trimethoprim/methoxazole, vancomycin, tetracycline, fluoroquinolones, ceftriaxone, Cefixime, Azithromycin, Isoniazid, Rifampin, Ethambutol, Pyrazinamide, Aminoglycoside, Capreomycin, Ciprofloxacin, Ofloxacin, gemifloxacin, Cycloserine, Ethionamide, and para-aminosalicylic acid.

Thus, various embodiments, the subject having an NK cell responsive disorder can have an immunodeficiency disorder. In some embodiments, the subject can have a primary immunodeficiency disorder. In some embodiments, the subject can have a secondary immunodeficiency disorder.

In some embodiments, immunodeficiency disorders can include uremia, diabetes (infective complications thereof, malnutrition, vitamin and mineral deficiencies, protein-losing enteropathies, nephrotic syndrome, myotonic dystrophy, sickle cell disease; or the like.

In some embodiments, immunodeficiency disorders can be cause or be partially caused by immunosuppressive agents, e.g., radiation, immunosuppressive drugs, corticosteroids, anti-lymphocyte or anti-thymocyte globulin, anti-T-cell monoclonal antibodies; or the like.

In some embodiments, immunodeficiency disorders can caused or partially caused-by surgery and trauma, e.g., burns, splenectomy, anesthesia, wounds, implanted medical devices; or the like.

In some embodiments, immunodeficiency disorders can include chronic fatigue syndrome (chronic fatigue immune dysfunction syndrome); Epstein-Barr virus infection, post viral fatigue syndrome, post-transplantation syndrome (host-graft disease), exposure to nitric oxide synthase inhibitors, aging, severe combined immunodeficiency, variable immunodeficiency syndrome, and the like.

Increasing NK cell activity would also be beneficial for treating subjects with disorders including, but not limited to a neurodegenerative disorder. As used herein, a neurodegenerative disorder involves degradation of neurons such as cerebral, spinal, and peripheral neurons (e.g., at neuromuscular junctions), more typically degradation of cerebral and spinal neurons. Neurodegenerative disorders can include Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; epileptic seizure, injury-induced seizure, chemically-induced seizure, or other diseases associated with superoxide dismutase (SOD) mutations; and the like. Neurodegenerative disorders can also include degradation of neurons caused by ischemia, seizure, thermal stress, radiation, toxin exposure, infection, injury, and the like. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like.

Other disorders in which increasing NK cell activity would be beneficial include disorders due to thermal stress, (thermal stress includes hyperthermia (e.g., from fever, heat stroke, burns, and the like) and hypothermia); radiation damage, e.g., due to visible light, ultraviolet light, microwaves, cosmic rays, alpha radiation, beta radiation, gamma radiation, X-rays, and the like, (for example, the damage could be radiation damage to non-cancerous tissue in a subject treated for cancer by radiation therapy); mechanical injury, e.g., trauma from surgery, accidents, certain disease conditions (e.g., pressure damage in glaucoma) and the like; and exposure to a toxin e.g., exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Another embodiment of the present invention is a method of treating a subject with a cancer. Optionally, the method of the invention can be used for a multi-drug resistant cancer as described below. The method comprises the step of administering an effective amount of a compound of Formula I through (V) or Table 1, or a tautomer, pharmaceutically acceptable salt, solvate, clathrate, or a prodrug thereof. Preferably, one or more additional anti-cancer drugs are co-administered with a compound of the invention. Examples of anti-cancer drugs are described below. Preferably, the co-administered anti-cancer drug is an agent that stabilizes microtubules, such as Taxol® or a taxanes derivative.

As noted above, one embodiment of the present invention is directed to treating subjects with a cancer. "Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

In another embodiment, a compound of the invention can be administered as adjuvant therapy to prevent the reoccurrence of cancer. For example, stage II and stage III melanoma are typically treated with surgery to remove the melanoma followed by chemotherapeutic treatment to prevent the reoccurrence of cancer. In one embodiment, one or more additional anti-cancer drugs are co-administered with a compound of the invention as adjuvant therapy. Examples of anti-cancer drugs are described below. In one embodiment, the co-administered anti-cancer drug is an agent that stabilizes microtubules, such as Taxol® or a taxanes derivative. In another embodiment, the co-administered anti-cancer drug is an immunotherapeutic anticancer agent.

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendioglioma, meningioma, spinal cord tumors, melanoma, neuroblastoma, pheochromocytorria, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1(acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer*

*Medicine* 5th Ed., Bast et al. Eds., B.C. Decker Inc. (2000). The entire teachings of the preceding references are incorporated herein by reference.

Additional cancers that can be treated or prevented by the methods of the present invention include, but are not limited to oral cavity & pharynx cancers, including tongue, mouth, pharynx, and other oral cavity cancers; digestive system cancers, including esophagus, small intestine, rectum, anus, anal canal, anorectum, liver & intrahepatic bile duct, gallbladder & other biliary, pancreas and other digestive organs; respiratory system cancers, including larynx and bronchus; bone & joint cancers; soft tissue (including heart) cancers; genital system cancers, including uterine cervix, uterine corpus, ovary, vulva, vagina & other genital, female, testis, penis & other genital, male; urinary system cancers, including kidney & renal pelvis, and ureter & other urinary organs; eye & orbit cancers; leukemia, including acute myeloid leukemia and chronic myeloid leukemia.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1(acute) cell line); and lymphoma (e.g., as exemplified by the U937 cell line).

In another embodiment, the disclosed method is believed to be particularly effective in treating a subject with an immunosensitive cancer. Immunosensitive cancers are cancers that respond to treatment with immunotherapy. Immunotherapy is described below in more detail. Cancers that respond to immunotherapy include renal cell carcinoma, melanoma (including superficial spreading melanoma, nodular melanoma, acral lentiginous melanoma, lentigo maligna melanoma which is also called Hutchinson's Freckle), multiple myeloma, myeloma, lymphoma, non-small-cell lung cancer, squamous cell carcinoma, basal cell carcinoma, fibrosarcoma and malignant brain tumors.

In another embodiment, the disclosed method is believed to be particularly effective in treating a subject with melanoma.

In another embodiment, the disclosed method is believed to be particularly effective in treating a subject with renal cell carcinoma.

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

Other anti-proliferative or anticancer therapies may be combined with the compounds of this invention to treat proliferative diseases and cancer. Other therapies or anticancer agents that may be used in combination with the inventive anticancer agents of the present invention include surgery, radiotherapy (including, but not limited to, gamma-radiation, neutron beam radiotherapy, electron beam radiotherapy, proton therapy, brachytherapy, and systemic radioactive isotopes), endocrine therapy, biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs.

The prophylactic or therapeutic agents of the combination therapies of the invention can be administered sequentially or concurrently.

As used herein, the terms "hyperthermia", "hyperthermia therapy," "thermal therapy," and "thermotherapy" are used interchangeably to mean a treatment where body tissue is exposed to high temperatures (up to 113 OF). The term as used herein includes all forms of hyperthermia, including local, regional, and whole-body. Various forms of energy can be used to deliver heat to the desired area, such as microwave, radiofrequency, lasers, and ultrasound. The treatment temperatures vary depending on the location of the tumor and the approach used.

In local hyperthermia, heat is applied to a small area (e.g. a tumor). The approaches to local hyperthermia vary with tumor location. External approaches are used to treat tumors in or just below the skin. In this method, applicators are place near or around the tumor and deliver energy directly to the tumor. Intraluminal or endocavitary approaches use probes to deliver energy to tumors within or near body cavities. Interstitial approaches are used to treat tumors deep within the body (e.g. brain tumors), by inserting probes or needles into the tumor under anesthesia.

In regional hyperthermia, heat is applied to large areas of tissue (e.g. body cavity, organ, or limb). Deep tissue approaches are used to treat cancers within the body (e.g. cervical or bladder cancer) by using external applicators. Regional perfusion approaches are used to treat cancers in the limbs or organs (e.g melanoma, liver, or lung cancer). In this approach some of the blood is removed and heated and then pumped back into the limb or organ. Anticancer drugs may be given during this process. Continuous hyperthermic peritoneal perfusion (CHPP) is used to treat cancers in the peritoneal cavity (e.g. peritoneal mesothelioma or stomach cancer). In this approach, heated anticancer drugs are pumped through the peritoneal cavity.

Whole-body hyperthermia is used to treat metastatic cancer. In this approach, the whole body is heated to 107-108° F. by using various techniques such as thermal chambers or hot water blankets.

An "effective amount" is the quantity of compound in which a beneficial clinical outcome is achieved when the compound is administered to a subject. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a an Hsp70-responsive disorder or an NK cell-responsive disorder, a "beneficial clinical outcome" includes reduction in the severity or number of symptoms associated with the disorder, elimination of an infection, or increase in the longevity of the subject compared with the absence of the treatment. The precise amount of compound administered to a subject will depend on the type and severity of the disease or condition and on the characteristics of the subject, such as general health, age, sex, body weight and tolerance to drugs. It may also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. When co-administered with another anti-cancer agent for the treatment of cancer; an "effective amount" of the second anti-cancer agent will depend on the type of drug used. Suitable dosages are known for approved anti-cancer agents and can be adjusted by the skilled artisan according to the condition of the subject, the type of cancer being treated and the compound of the invention being used.

Another embodiment of the present invention is a pharmaceutical composition comprising a compound of the invention, or a tautomer, pharmaceutically acceptable salt, solvate, clathrate, or a prodrug thereof, and a pharmaceutically acceptable carrier or diluent.

Suitable pharmaceutically acceptable carriers may contain inert ingredients which do not inhibit the biological activity of the disclosed disalts. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

The compounds of the invention are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds of the invention can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

Optionally, a compound of the invention, or a tautomer, pharmaceutically acceptable salt, solvate, clathrate, or a prodrug thereof, can be co-administered to treat a patient with a proliferative disorder such as cancer, or to prevent the reoccurrence of a proliferative disorder such as cancer, with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other drugs that can be used in combination with the compounds of the invention to treat a patient with a proliferative disorder such as cancer, or to prevent the reoccurrence of a proliferative disorder such as cancer, include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacririe; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; tnapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; spairfosic acid; spicamycin D; spiromustine; splenopentin; spongistatin 1; squalamine; stem cell inhibitor; stem-cell division inhibitors; stipiamide; stromelysiri inhibitors; sulfinosine; superactive vasoactive intestinal peptide antagonist; suradista; suramin; swainsonine; synthetic glycosaminoglycans; talliniustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in combination with the compounds of the invention to treat a proliferative disorder such as cancer, or to prevent the reoccurrence of a proliferative disorder such as cancer, include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

Chemotherapeutic agents that can be used in combination with the compounds of the invention to treat a patient with a proliferative disorder such as cancer, or to prevent the reoccurrence of a proliferative disorder such as cancer, include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine-analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention of a proliferative disorder such as cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxrymesterone), antiandrogen (e.g., flutamide), gonadotropin releasing hormone analog (e.g., leuprolide). Other agents that can be used in the methods and with the compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In one embodiment, the compounds of the invention can be used in combination with an immunotherapeutic agent for the treatment of a proliferative disorder such as cancer, or to prevent the reoccurrence of a proliferative disorder such as cancer. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include: cancer vaccines, tumor cell vaccines (autologous or allogeneic), dendritic cell vaccines, antigen vaccines, anti-idiotype vaccines, DNA vaccines, Lymphokine-Activated Killer (LAK) Cell Therapy, or Tumor-Infiltrating Lymphocyte (TIL) Vaccine with Interleukin-2 (IL-2). Active immunotherapies are currently being used to treat or being tested to treat various types of cancers, including melanoma, kidney (renal) cancer, bladder cancer, prostate cancer, ovarian cancer, breast cancer, colorectal cancer, lung cancer, leukemia, prostate cancer, non-Hodgkin's lymphoma, pancreatic cancer, lymphoma, multiple myeloma, head and neck cancer, liver cancer, malignant brain tumors, and advanced melanoma.

Examples of passive immunotherapies include: monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to a chemotherapy drug (chemolabeled), a radioactive particle (radiolabeled), or a toxin (immunotoxin). A number of naked monoclonal antibody drugs have been approved for treating cancer, including:

Rituximab (Rituxan), an antibody against the CD20 antigen used to treat B cell non-Hodgkin lymphoma; Trastuzumab (Herceptin), an antibody against the HER2 protein used to treat advanced breast cancer; Alemtuzumab (Campath), an antibody against the CD52 antigen used to treat B cell chronic lymphocytic leukemia (B-CLL); Cetuximab (Erbitux), an antibody against the EGFR protein used in combination with irinotecan to treat advanced colorectal cancer and to treat head and neck cancers; and Bevacizumab (Avastin) which is an antiangiogenesis therapy that works against the VEGF protein and is used in combination with chemotherapy to treat metastatic colorectal cancer. A number of conjugated monoclonal antibodies have been approved for treating cancer, including: Radiolabeled antibody Ibritumomab tiuxetan (Zevalin) which delivers radioactivity directly to cancerous B lymphocytes and is used to treat B cell non-Hodgkin lymphoma; radiolabeled antibody Tositumomab (Bexxar) which is used to treat certain types of non-Hodgkin lymphoma; and immunotoxin Gemtuzumab ozogamicin (Mylotarg) which contains calicheamicin and is used to treat acute myelogenous leukemia (AML). BL22 is a conjugated monoclonal antibody currently in testing for treating hairy cell leukemia and there are several immunotoxin clinical trials in progress for treating leukemias, lymphomas, and brain tumors. There are also approved radiolabeled antibodies used to detect cancer, including OncoScint for detecting colorectal and ovarian cancers and ProstaScint for detecting prostate cancers. Targeted therapies containing toxins are toxins linked to growth factors and do not contain antibodies. An example of an approved targeted therapy containing toxins is denileukin diftitox (Ontak) which is used to treat a type of skin lymphoma (cutaneous T cell lymphoma).

Examples of adjuvant immunotherapies include: cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15; IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP). Clinical studies have shown that combining IL-2 with other cytokines, such as IFN-alpha, can lead to a synergistic response.

Several types of immunotherapies are being used to treat melanoma patients. IFN-alpha and IL-2 are approved for treatment of people with metastatic melanoma. BCG is being tested in combination with melanoma vaccines and other immunotherapies. Tumor-infiltrating lymphocytes have been shown to shrink melanoma tumors in a phase 1 clinical trial. Human monoclonal antibodies to ganglioside antigens have been shown to regress cutaneous recurrent melanoma tumors. Some autologous and allogeneic tumor cell vaccines, antigen vaccines (including polyvalent antigen vaccines), viral vaccines, and dendritic cell vaccines have also been shown to shrink tumors. Clinical trials continue for these and other melanoma immunotherapies. Melanoma patients with a high IgM response often survive better than those who elicit no or low IgM antibodies (Morton et al., 1992). Combined IL-12/TNF-alpha immunotherapy has been shown to significantly retard tumor growth in three tumor models in mice (B16F10 melanoma, Lewis lung (LL/2) carcinoma and L1 sarcoma) as compared with controls and mice treated with either cytokine alone. IFN-alpha is approved for the treatment of malignant melanoma, chronic myelogenous leukemia (CML), hairy cell leukemia, and Kaposi's sarcoma.

Several types of immunotherapies are being used to treat patients that have renal cancer. IFN-alpha and IL-2 are approved for treatment of people with metastatic renal (kidney) cancer. A combination therapy using IL-2, interferon, and chemotherapy is being tested for treatment of renal cancer. Treatment with a tumor cell vaccine plus the adjuvant BCG has been shown to shrink tumors in some advanced renal cancer patients. DNA vaccines and tumor-infiltrating lymphocytes are also being tested as treatments for renal cancer. Chimeric bispecific G250/anti-CD3 monoclonal antibodies have been shown to mediate cell lysis of renal cell carcinoma cell lines by cloned human CD8+ T cells or by IL-2 stimulated peripheral blood lymphocytes.

As used herein, a "microtubulin stabilizer" means an anticancer agent which acts by arresting cells in the G2-M phases due to stabilization of microtubules. Agents which are microtubulin stabilizers can be used in combination with the compounds of the invention to treat patients having a proliferative disorder such as cancer, or to prevent the reoccurrence of a proliferative disorder such as cancer. Examples of microtubulin stabilizers include taxol and taxol analogues. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anti-cancer agent which acts by inhibiting tubulin polymerization or microtubule assembly. Agents which are microtubulin inhibitors can be used in combination with the compounds of the invention to treat patients having a proliferative disorder such as cancer, or to prevent the reoccurrence of a proliferative disorder such as cancer. Examples of microtubulin inhibitors include without limitation the following marketed drugs and drugs in development: Erbuilozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68.144 (Asta Medica); Diazonamide A; A-293620 (Abbott); NPI-2350 (Nereus); TUB-245 (Aventis); A-259720 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Figure 2:
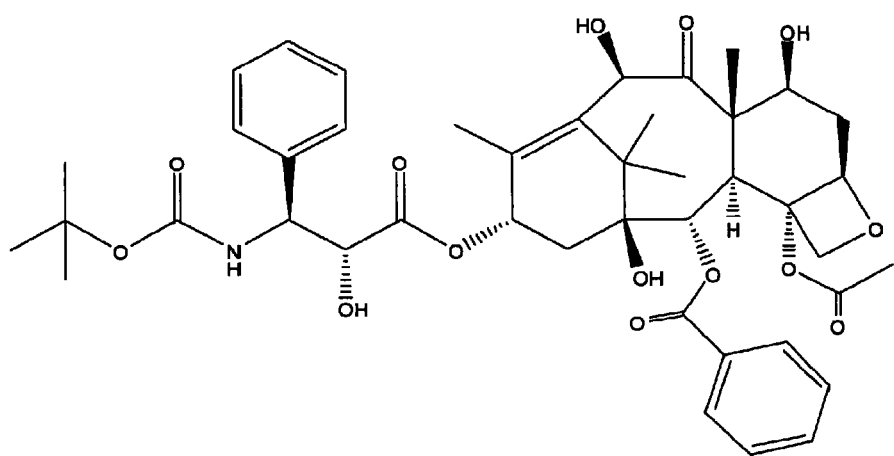
FIG. 2 is the structure of Taxotere® (docetaxel).
Figure 3:
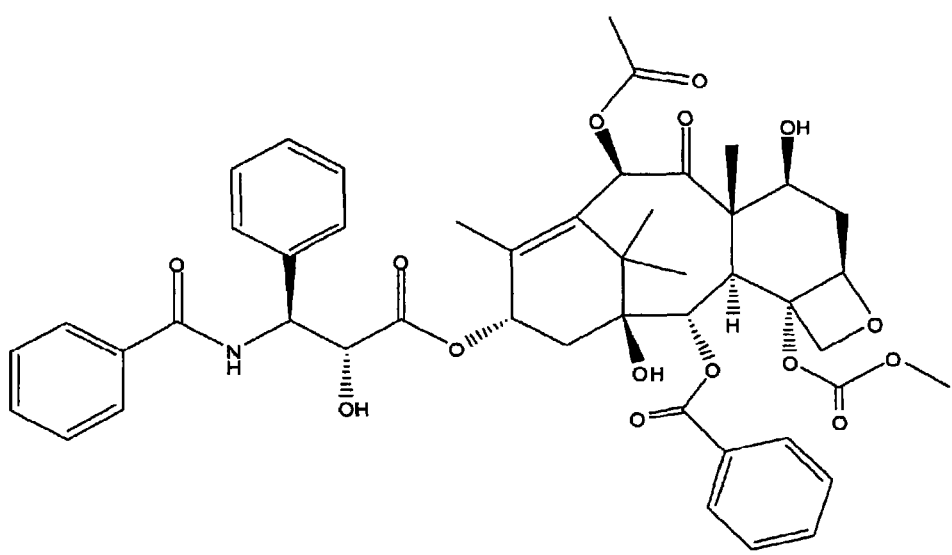
FIGS. 3-23 each depict the structure of particular Taxol® analogs.
Figure 4:
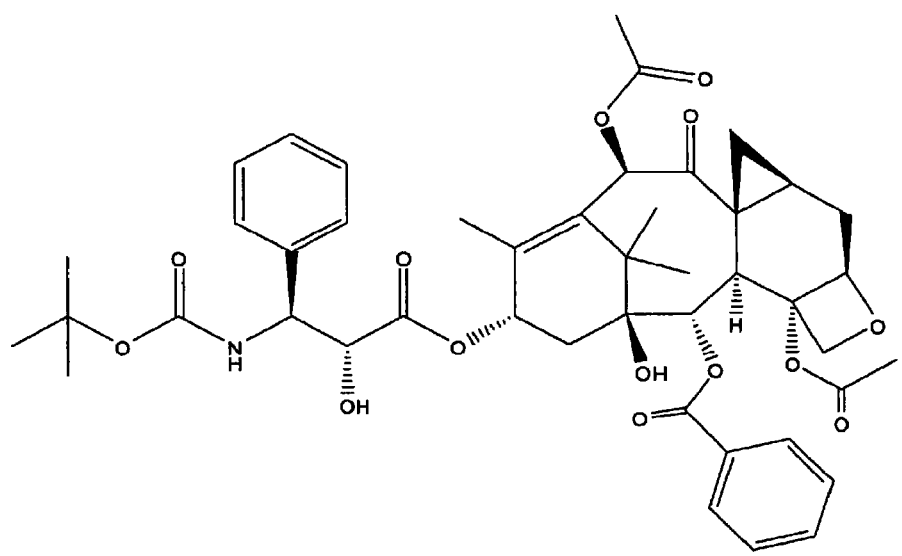
Figure 5:
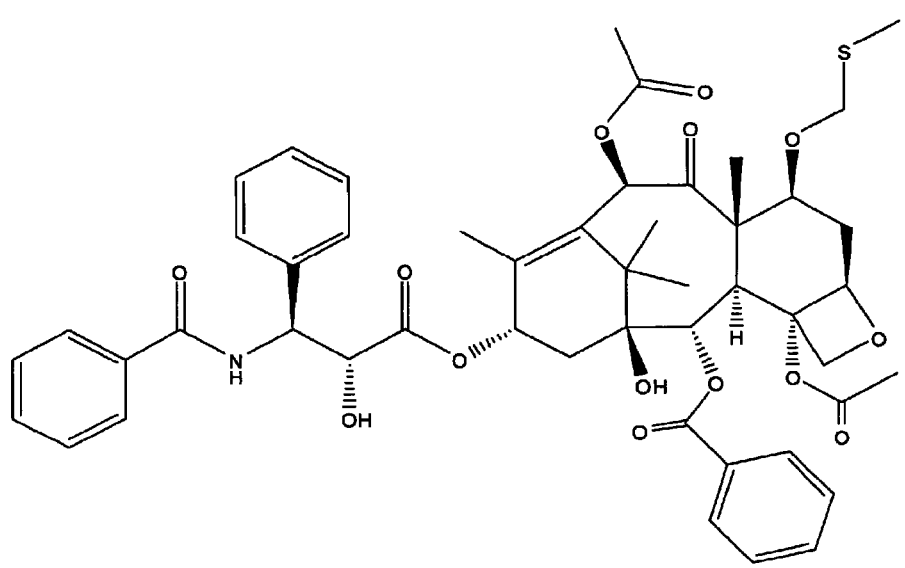
Figure 6:
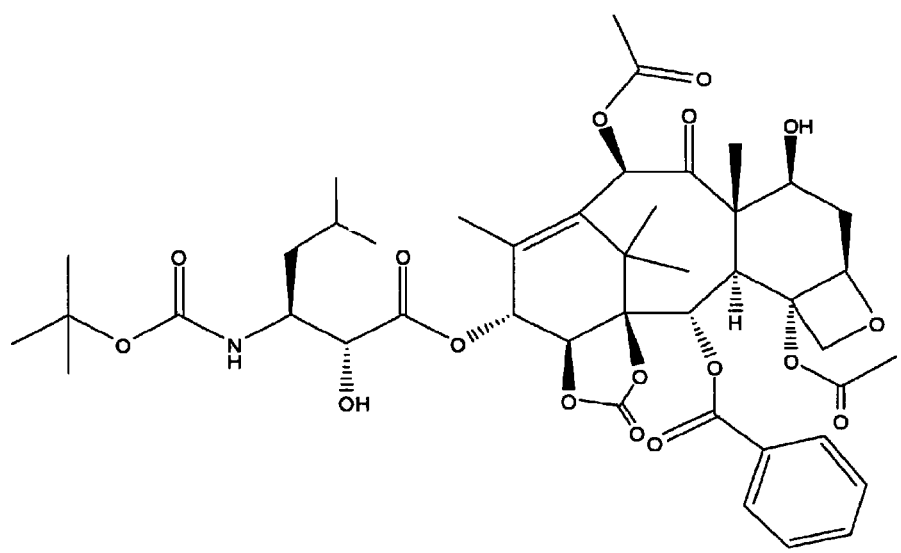
Figure 7:
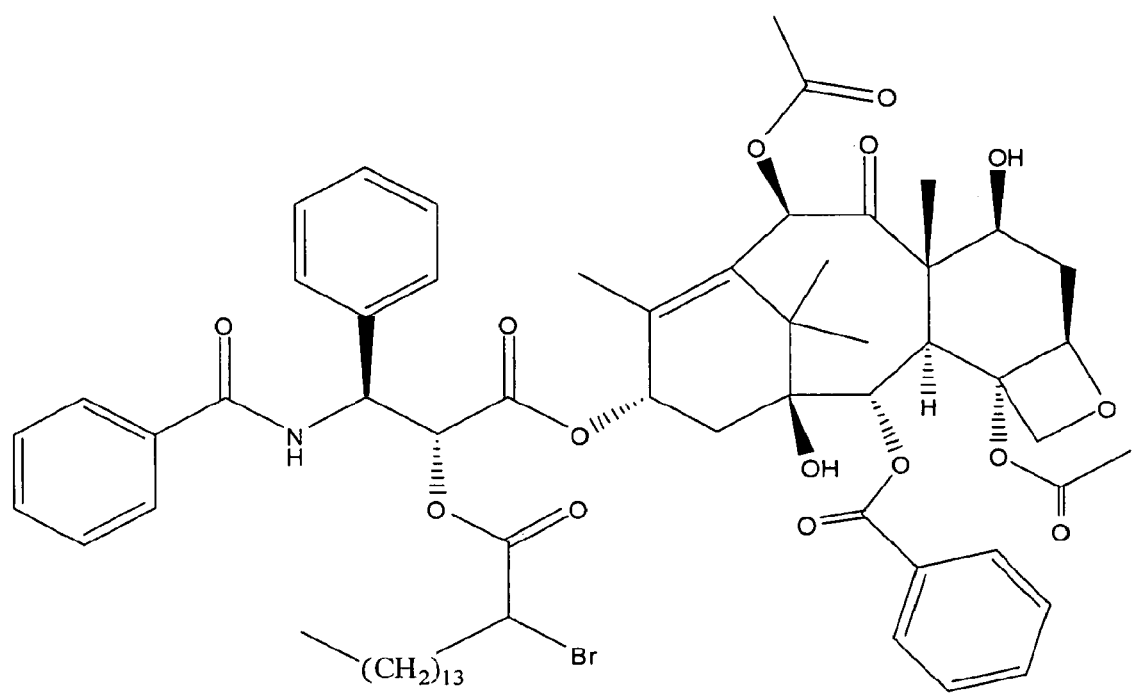
Figure 8:
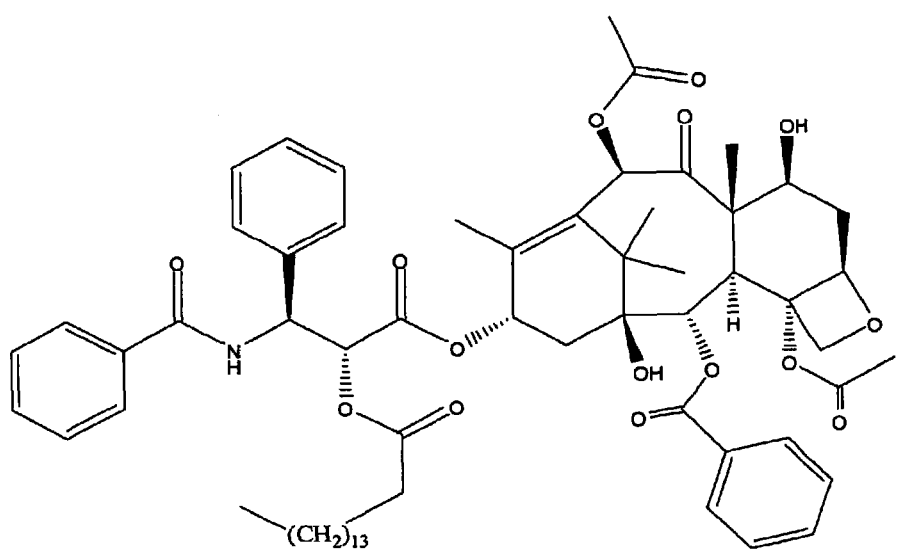
Figure 9:
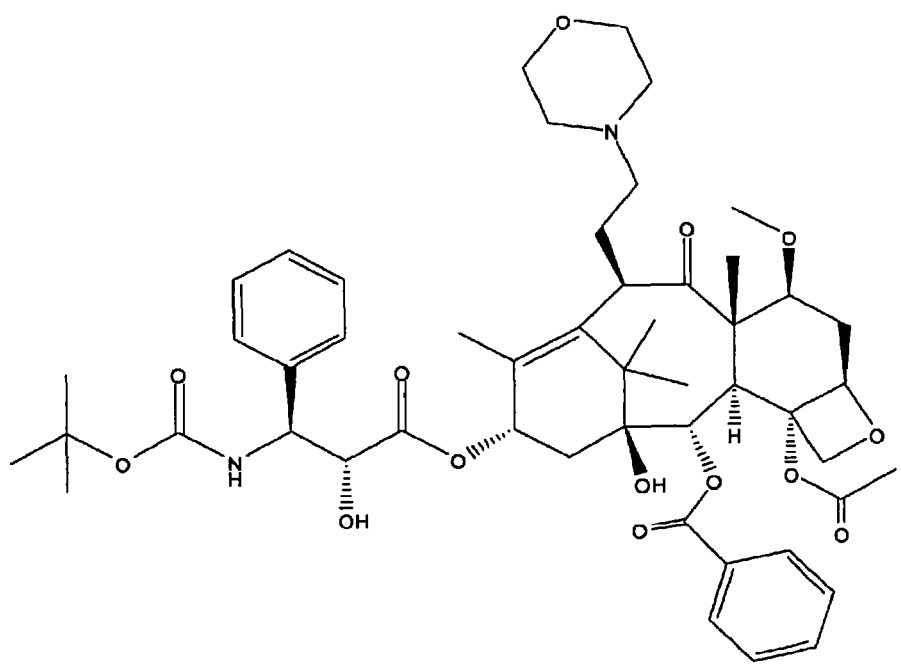
Figure 10:
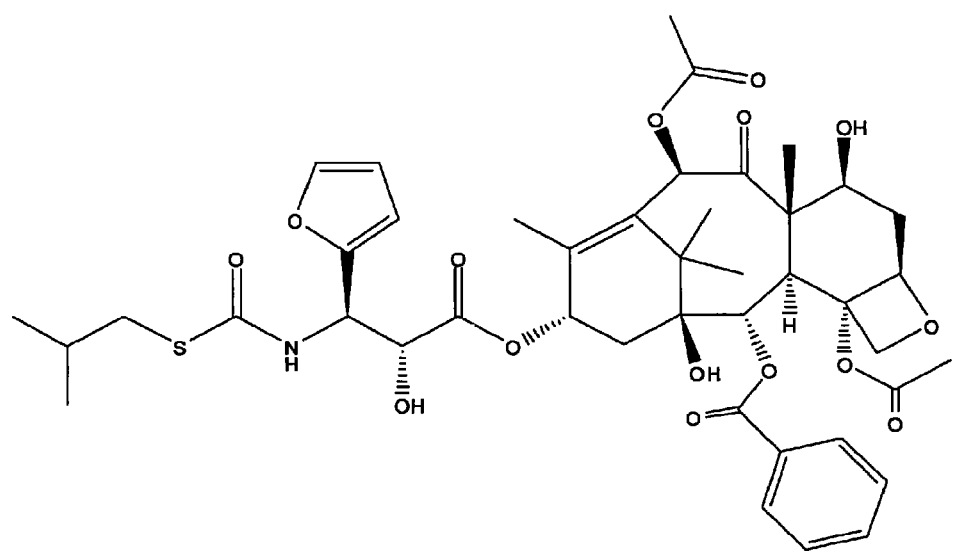
Figure 11:
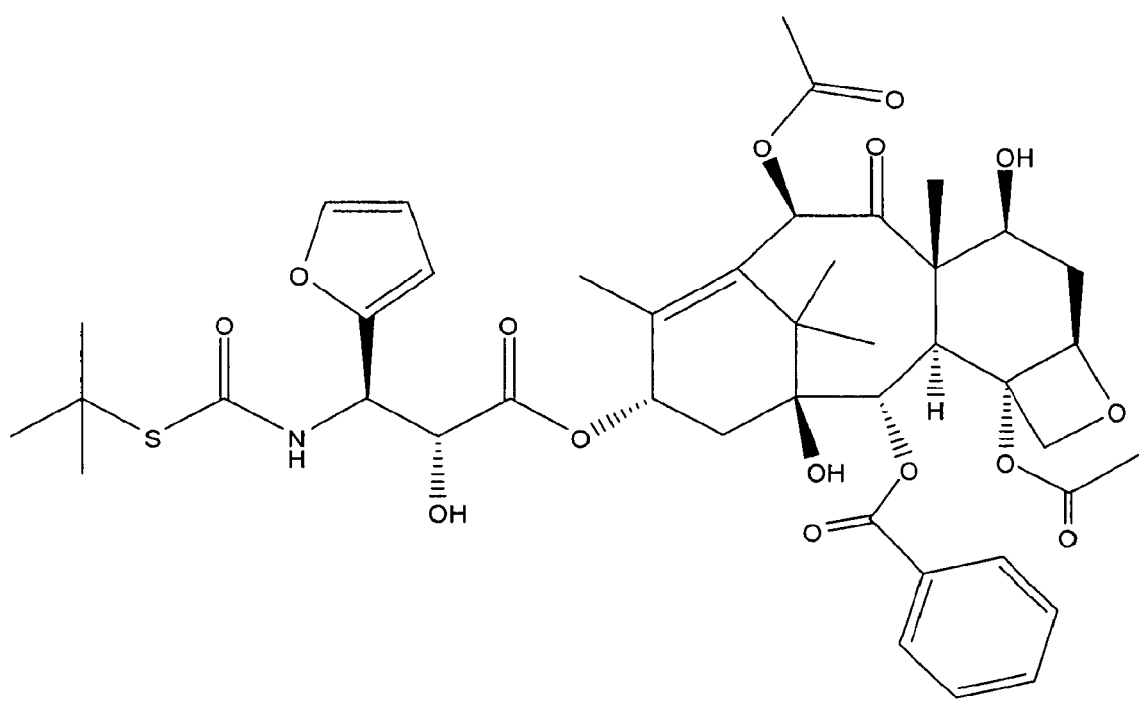
Figure 12:
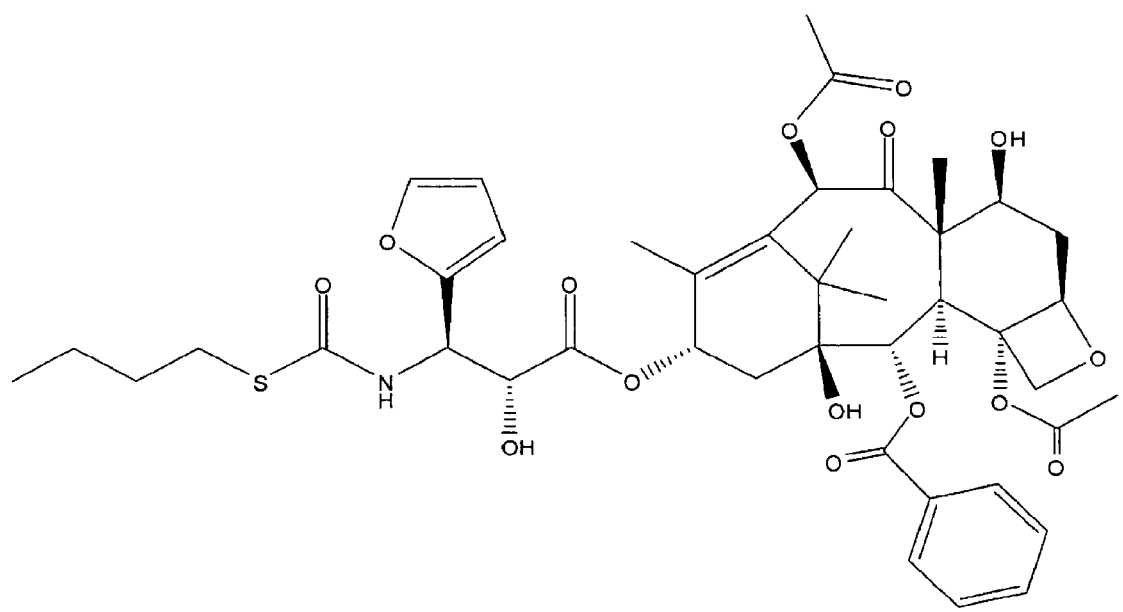
Figure 13:
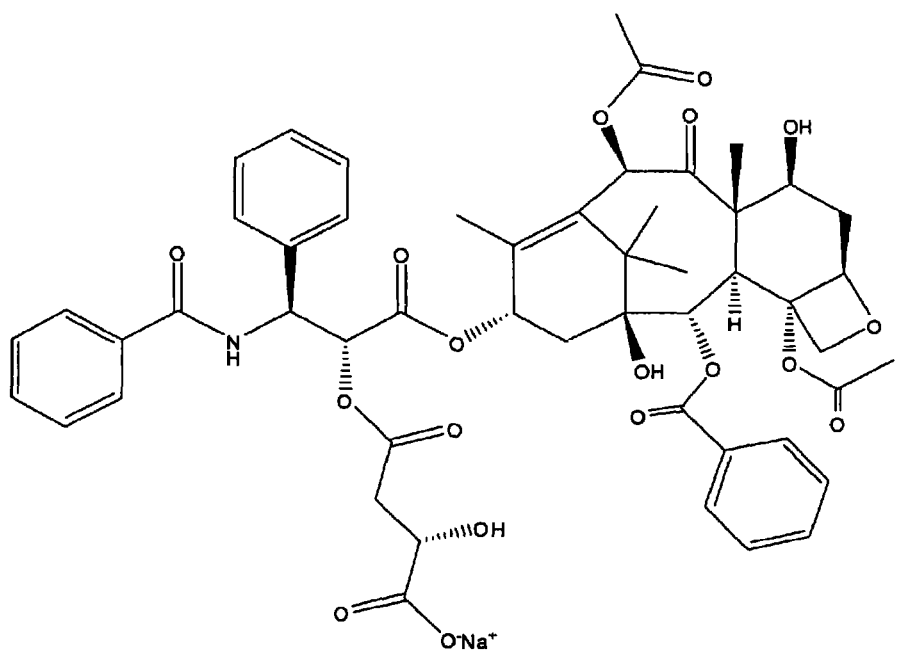
Figure 14:
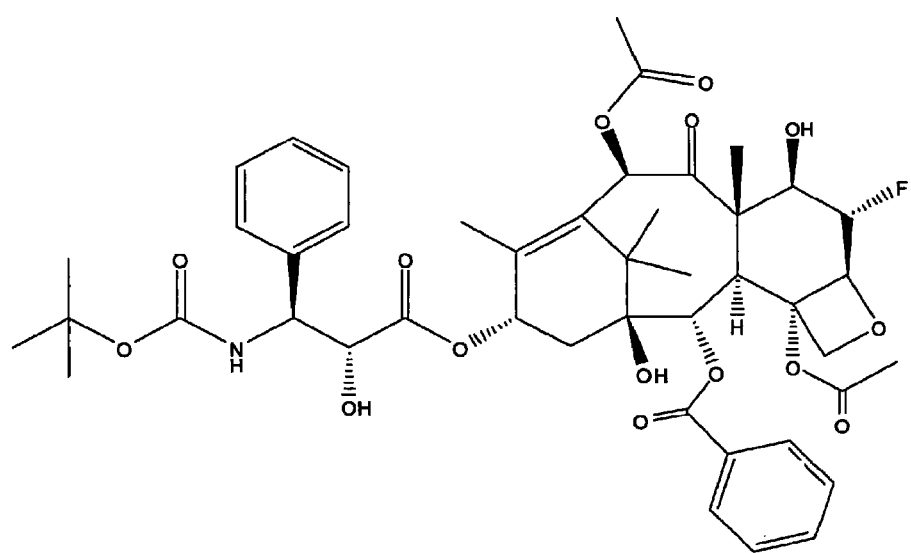
Figure 15:
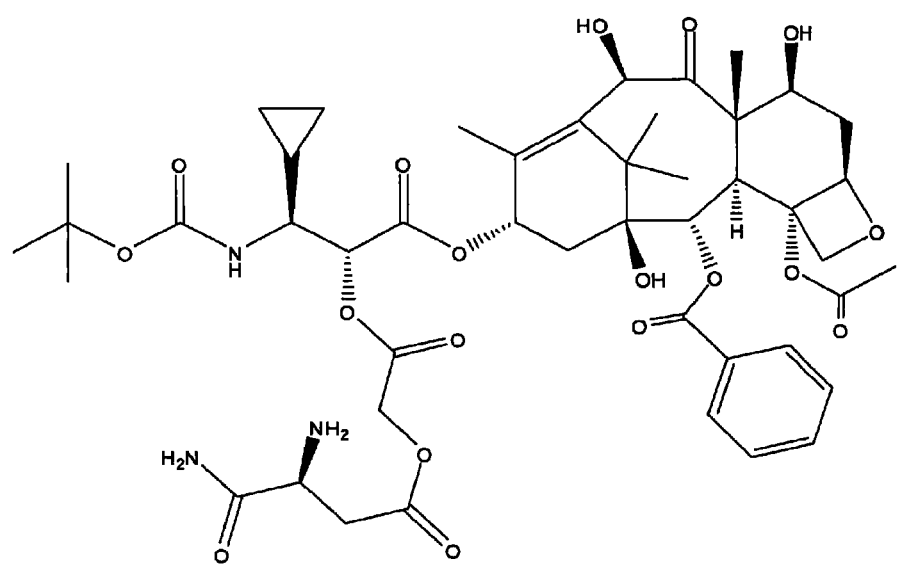
Figure 16:
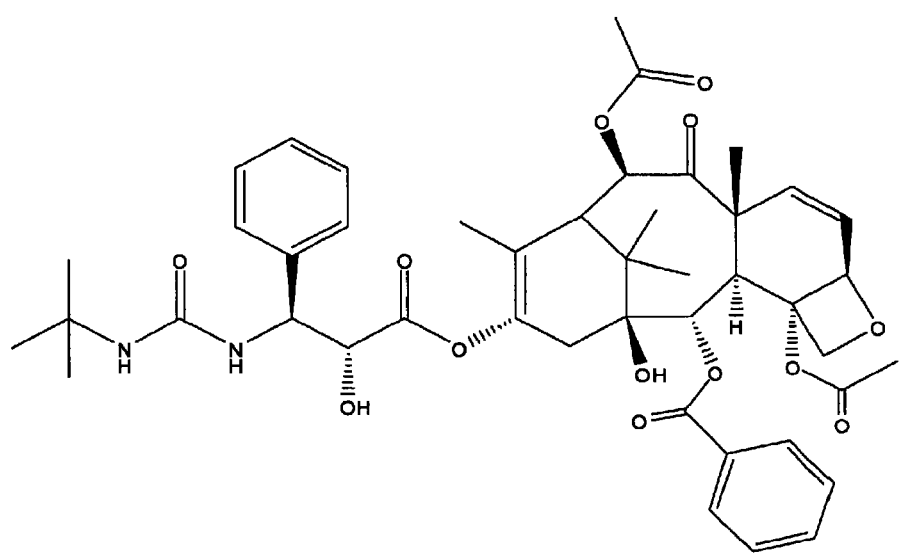
Figure 17:
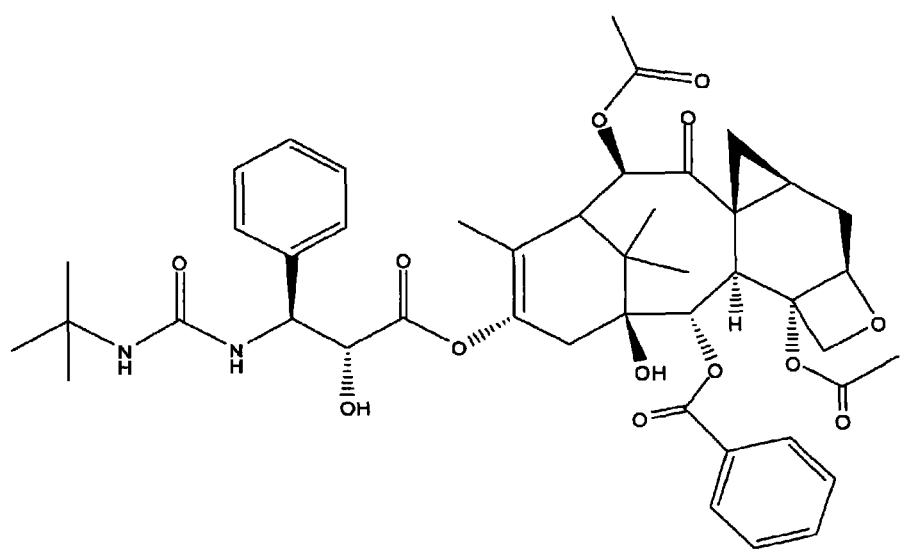
Figure 18:
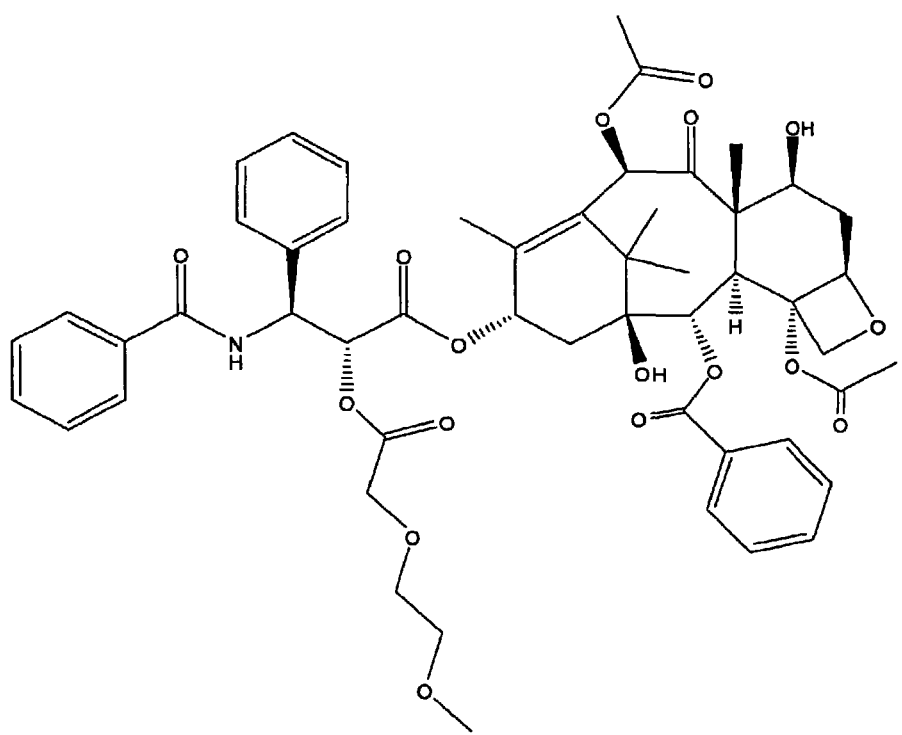
Figure 19:
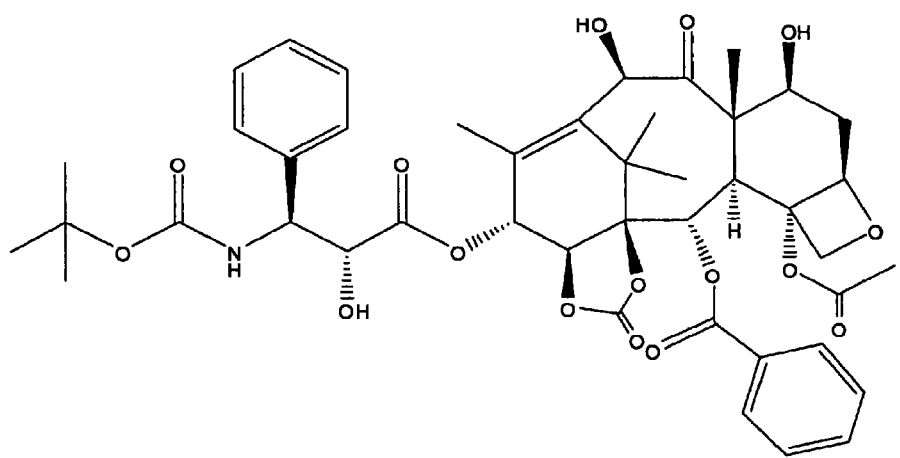
Figure 20:
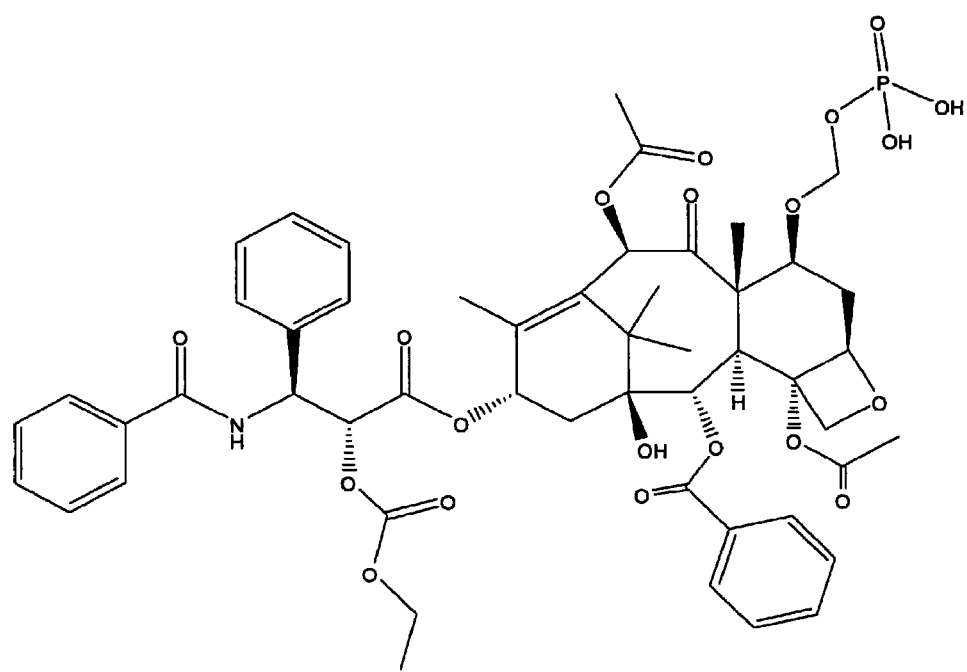
Figure 21:
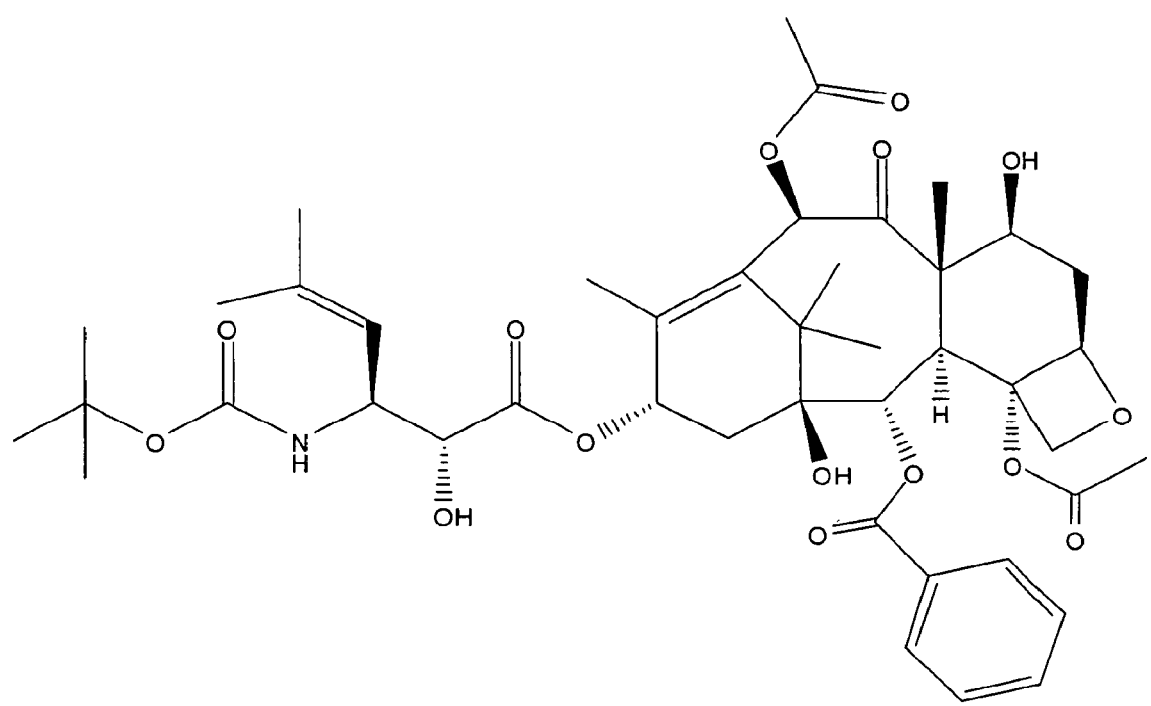
Figure 22:
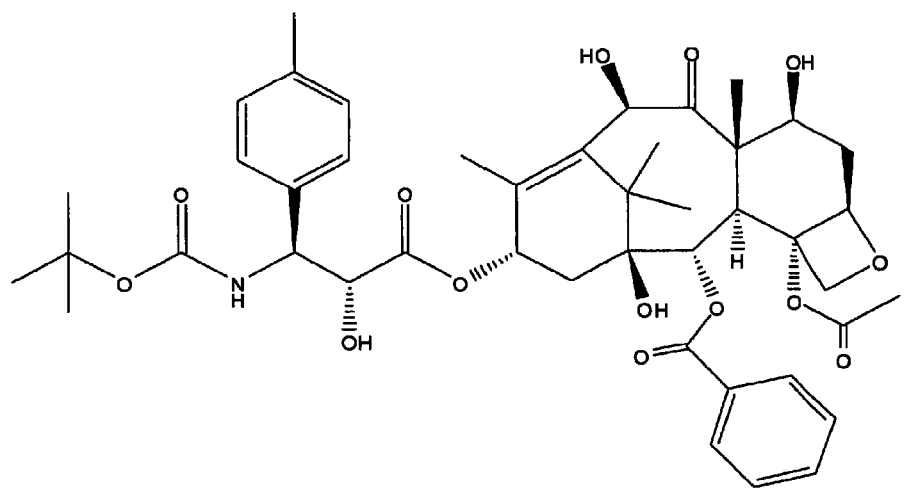
Figure 23:
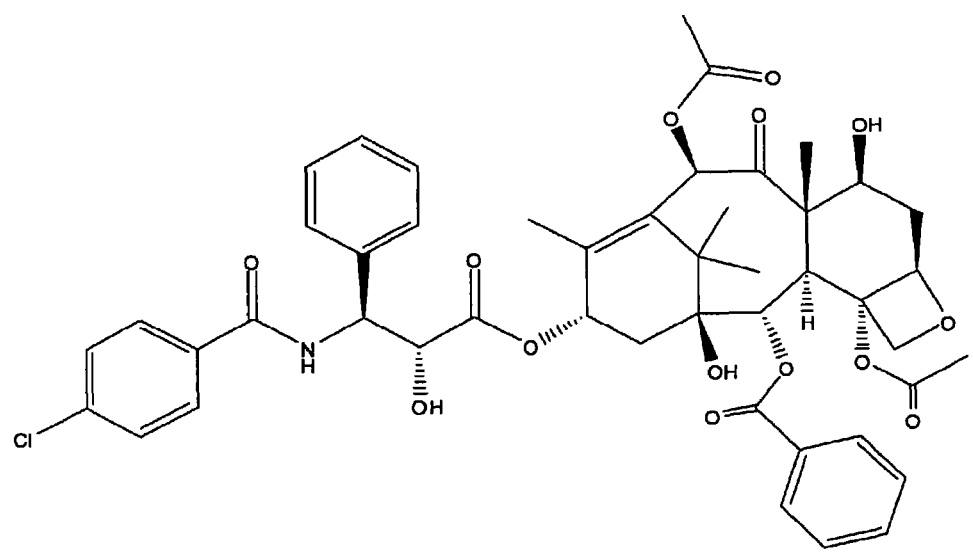

Taxol®, also referred to as "paclitaxel", is a well-known anti-cancer drug which acts by enhancing and stabilizing microtubule formation. The structure of Taxol® is shown in FIG. 1. Many analogs of Taxol® are known, including Taxotere®, the structure of which is shown in FIG. 2. Taxotere® is also referred to as "docetaxol". The structures of other Taxol® analogs are shown in FIGS. 3-23. These compounds have the basic taxane skeleton as a common structure feature and have also been shown to have the ability to arrest cells in the G2-M phases due to stabilization of microtubules. Thus, it is apparent from FIGS. 3-23 that a wide variety of substituents can decorate the taxane skeleton without adversely affecting biological activity. It is also apparent that zero, one or both of the cyclohexane rings of a taxol analog can have a double bond at the indicated positions. For clarity purposes, the basic taxane skeleton is shown below in Structural Formula (VI):

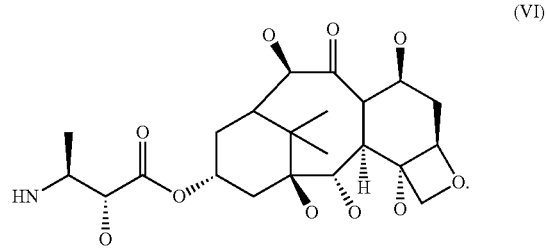

(VI)

Double bonds have been omitted from the cyclohexane rings in the taxane skeleton represented by Structural Formula (VI). The basic taxane skeleton can include zero or one double bond in one or both cyclohexane rings, as indicated in FIGS. 3-23 and Structural Formulas (VII) and (VIII) below. A number of atoms have also been omitted from Structural Formula (VI) to indicate sites in which structural variation commonly occurs among taxol analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "Taxol® analog" is defined herein to mean a compound which has the basic taxane skeleton and which promotes microtubule formation. Taxol® analogs may be formulated as a nanoparticle colloidal composition to improve the infusion time and to eliminate the need to deliver the drug with Cremophor which causes hypersensitivity reactions in some patients. An example of a Taxol® analog formulated as a nanoparticle colloidal composition is Abraxane which is a nanoparticle colloidal composition of protein-stabilized paclitaxel that is reconstituted in saline.

Typically, the Taxol® analogs used herein are represented by Structural Formula (VII) or (VIII):

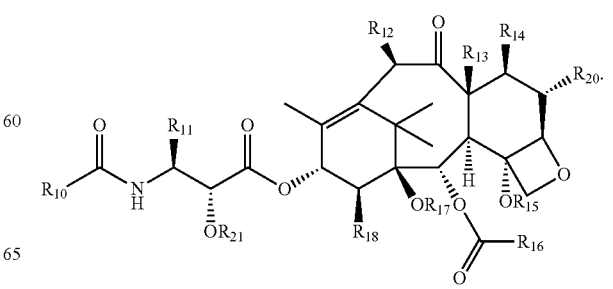

(VII)

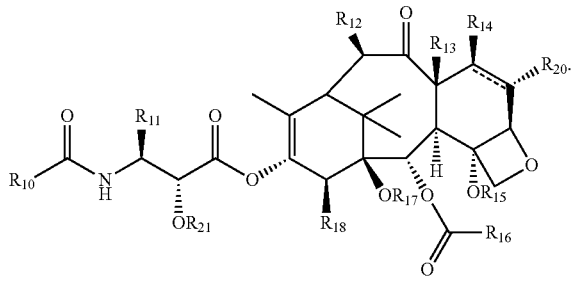

(VIII)

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl)-S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O (substituted lower alkyl), —OC(O)—NH (lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VII) and (VIII) are defined as follows: $R_{10}$ is phenyl, tert-butoxy, —S—CH$_2$—CH$_2$—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH═C(CH$_3$)$_2$ or para-chlorophenyl; $R_{11}$ is phenyl, (CH$_3$)$_2$CHCH$_2$—, -2-furanyl, cyclopropyl or para-toluyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{18}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 24:
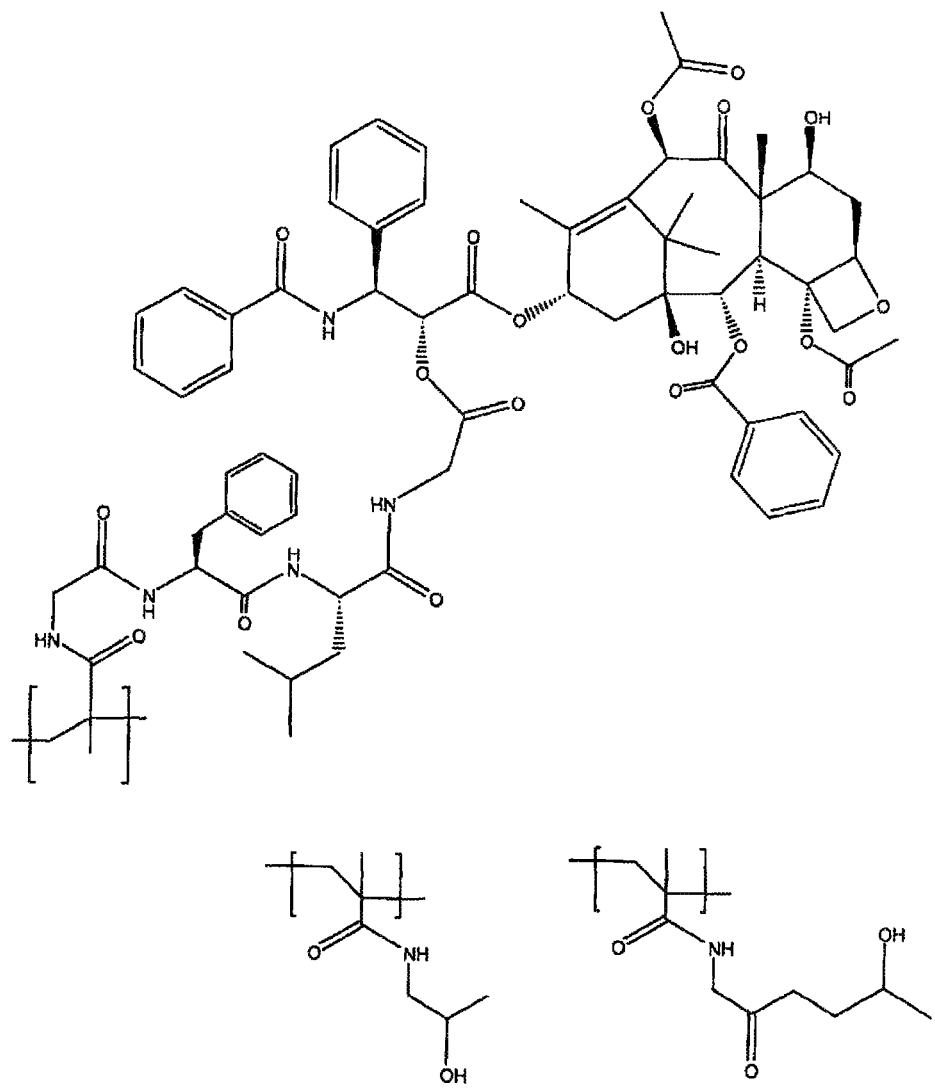
FIG. 24 is the structure of a polymer comprising a Taxol® analog group pendent from the polymer backbone. The polymer is a terpolymer of the three monomer units shown.

A Taxol® analog can also be bonded to or be pendent from a pharmaceutically acceptable polymer, such as a polyacrylamide. One example of a polymer of this type is shown in FIG. 24. The term "Taxol® analog", as it is used herein, includes such polymers.

In some embodiments, Taxol® analogs have a taxane skeleton represented by Structural Formula IX, wherein Z is O, S, or NR. Taxol® analogs that have the taxane skeleton shown in Structural Formula IX can have various substituents attached to the taxane skeleton and can have a double bond in zero, one or both of the cyclohexane rings as shown, for example in FIGS. 3-23.

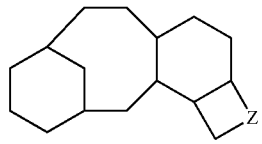

(IX)

Various Taxol® analogs and Taxol® formulations are described in Hennenfent et al. (2006) *Annals of Oncology* 17:735-749; Gradishar (2006) *Expert Opin. Pharmacother.* 7(8):1041-53; Attard et al. (2006) *Pathol Biol* 54(2):72-84; Straubinger et al. (2005) *Methods Enzymol.* 391:97-117; Ten Tije et al. (2003) *Clin Pharmacokinet.* 42(7):665-85; and Nuijen et al. (2001) *Invest New Drugs.* 19(2): 143-53, the entire teachings of which are incorporated herein by reference.

In some embodiments, the invention provides a method for treating or inhibiting angiogenesis in a subject in need thereof, comprising administering to the subject an effective amount of a compound represented by formula (I) through (V), or Table 1. As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin disclolorations (e.g., hemangioma, nevus flammeus, or nevus simplex); wound healing; hypertrophic scars, i.e., keloids; wound granulation; vascular adhesions; cat scratch disease (Rochele ninalia quintosa); ulcers (*Helicobacter pylori*); keratoconjunctivitis; gingivitis; periodontal disease; epulis; hepatitis; tonsillitis; obesity; rhinitis; laryngitis; tracheitis; bronchitis, bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease. Anti-angiogenesis can be demonstrated by any method known to those skilled in the art, such as the method described herein in Examples 9 and 10.

Several intermediates used in the preparation of the compounds of the invention can be prepared by the methods disclosed in U.S. Pat. Nos. 6,800,660, 6,762,204, and 6,825,235. The entire teachings of each of these patents are incorporated herein by reference.

In one embodiment, the compounds of the invention are prepared by reacting a thiohydrazide (intermediate (c)) with a diketone to form a compound represented by formula (I), (II), (III), (IV) or (V).

Thiohydrazides (intermediate (c)) can be prepared from intermediate (a) or intermediate (b). Intermediate (a) can be prepared by the method shown in scheme I. In this method a Grindard reagent is reacted with carbon disulfide to form (i). About 1 equivalent of sodium salt of chloro-acetic acid (ii) is reacted with to (i), and the reaction is quenched with an acid to form intermediate (a).

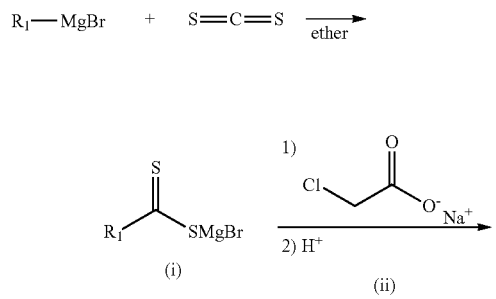

Alternatively, intermediate (a) can be prepared by the method shown in Scheme II. In this method, an aldehyde (iii) is reacted with piperidine in the presence of $S_3$ to form compound (iv). Compound (iv) is reacted with bromo-acetic acid to form compound (v). Compound (v) is dissolved in ethanol and treated with H2S to form intermediate (a).

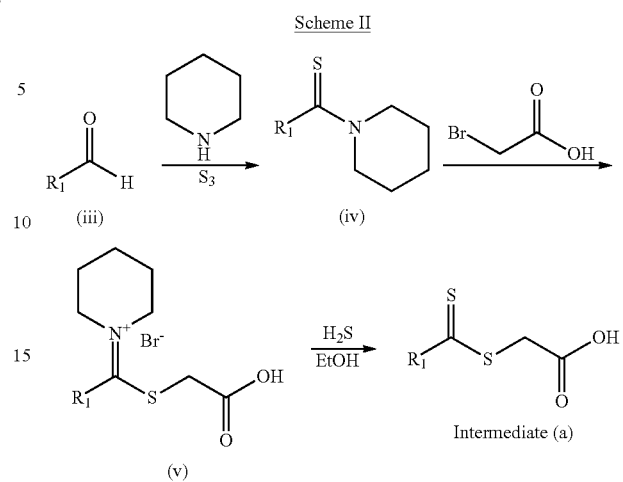

Intermediate (a) can be converted to a thiohydrazide (intermediate (c)) by reacting it with a hydrazine derivative (vi) in the presence of a base as shown in Scheme III.

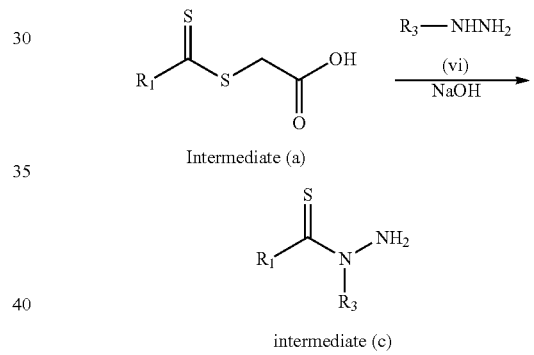

Intermediate (b) can be prepared by the method shown in Scheme IV. In this method, hydrazine derivative (iv) is protected using BOC anhydride in the presence of a base to form compound (vii). Compound (vii) is reacted with acid chloride (viii) in the presence of a base to form compound (ix). The BOC protecting group is removed from compound (ix) by treating it with a solution of trifluoroacetic acid in dichloromethane, followed by quenching with a base at about 0° C. to form intermediate (b).

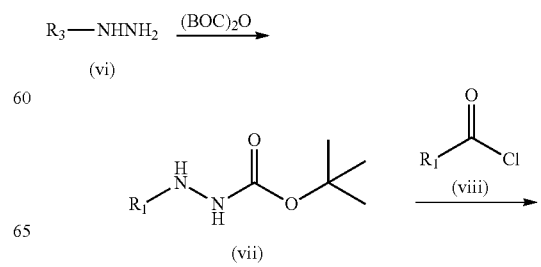

-continued

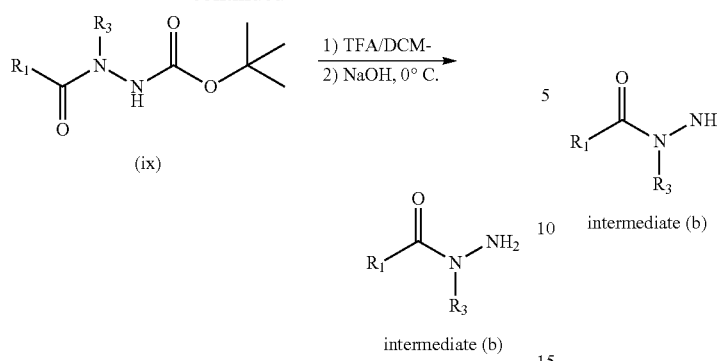

(ix)

intermediate (b)

Alternatively, intermediate (b) can be prepared by the method shown in Scheme V. In this method, hydrazide derivative (vi) is reacted with acid chloride (viii) in the presence of a base to form a mixture of regioisomers from which intermediate (b) can be separated by chromatography (see Scheme V, Method A). A carboxylic acid derivative (x) can be used instead of acid chloride (viii) if DCC or EDC is used to catalyze the reaction (see Scheme V, Method B).

Scheme V

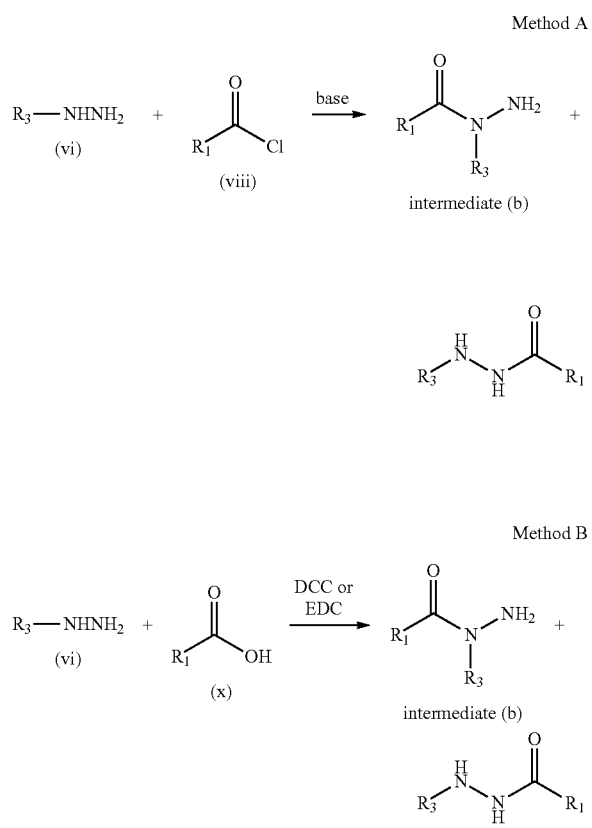

Intermediate (b) can be converted to a thiohydrazide (intermediate (c)) by treating it with Lawesson's reagent or $P_2S_5$ as shown in Scheme VI (see *J. of Organic Chem.* (1990), 55:2421-2427 and *J. of Organic Chem.* (1983), 48:214-222, the entire teachings of each of these references are incorporated by reference).

Scheme VI

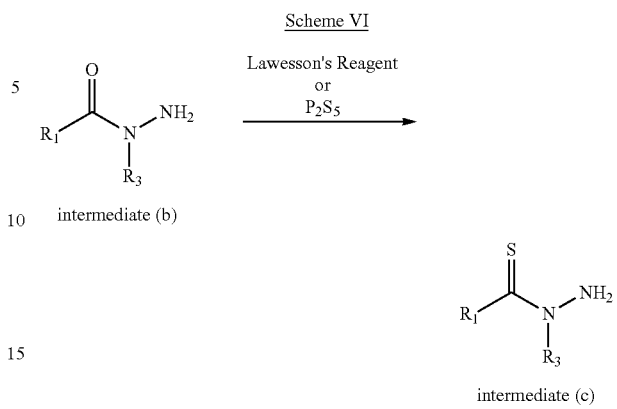

intermediate (c)

Compounds of the invention in which $R_1$ is the same as $R_2$ and $R_3$ is the same as $R_4$ can be prepared by reacting a diketone with 2 or more equivalents of intermediate (c) in the presence of a base such as $Na_2SO_4$, as shown in Scheme VII.

Scheme VII

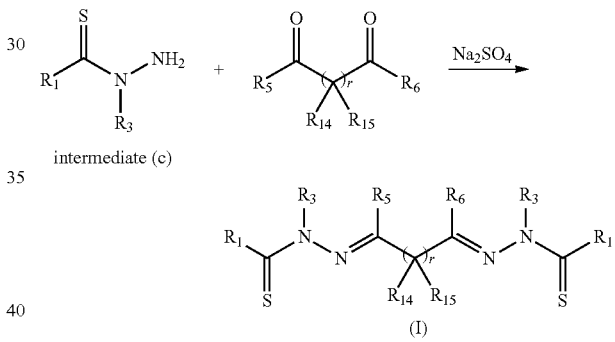

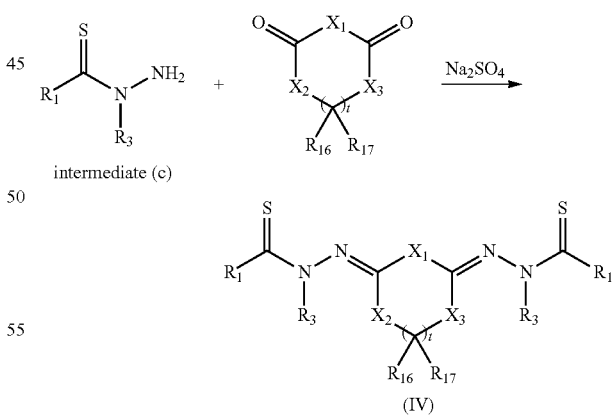

Compounds of the invention in which R, is different than $R_2$ and/or $R_3$ is different than $R_4$ can be prepared by reacting a diketone with 1 equivalent of intermediate (c) in the presence of a base such as $Na_2SO_4$ to form compound (xi). Compound (xi) or (xii) is then reacted with intermediate (c) having different $R_1$ and/or $R_3$ groups to form unsymmetrical compounds of the invention (see Scheme VIII).

Scheme VIII

Method A

[Chemical structures showing intermediate (c) reacting with diketone in presence of Na₂SO₄ to form (xi), then with thiohydrazide and Na₂SO₄ to form (I)]

Method B

[Chemical structures showing intermediate (c) reacting with diketone in presence of Na₂SO₄ to form (xii), then with thiohydrazide and Na₂SO₄ to form (IV)]

Compounds represented by formula (V) in which X is $CR_{22}R_{23}$ and Z is N can be prepared by reacting 2 equivalents or more of intermediate (c) in which $R_3$ is —H with dihalo-diketone (xiii) followed by treatment with a strong base such as NaH or potassium tert-butoxide to form compounds represented by formula Va (see Scheme IX). Compounds in which $R_{24}$ is different from $R_{25}$ can be prepare by analogous methods to those shown in Scheme VIII. ($X_4$ in Scheme IX is a halo).

Scheme IX

[Chemical structures showing (xiii) reacting with intermediate (c), 1) NaSO₄, 2) NaH or KOBu-t, to form (Va)]

Compounds represented by formula (V) in which X is O and Z is N can be prepared from a thiohydrazide represented by intermediate (d):

intermediate (d)

[Structure of intermediate (d)]

Intermediate (d) can be prepared by analogous methods to those used to prepare intermediate (c) starting from hydrazide derivative (xiv):

(xiv)

[Structure of (xiv)]

Di-carboxylic acid (xv) is reacted with 2 equivalents or more of intermediate (d) in the presence of DCC or EDC to form compound (xvi). The hydroxyl groups of compound (xvi) can be converted to a good leaving group such as a halo, O-mesyl; O-triflate, and the like by conventional methods such as treatment with NBS/PPh₃, mesyl chloride, triflic anhydride, or HI to form compound (xvii) wherein $X_5$ is a halo, O-mesyl, O-triflate. Compound (xvii) is treated with a strong base such as NaH or potassium tert-butoxide to form compounds represented by formula Vb (see Scheme X). Compounds in which $R_{24}$ is different from $R_{25}$ can be prepare by analogous methods to those shown in Scheme VIII. ($X_4$ in Scheme IX is a halo).

Scheme X

[Structure of (xv): di-carboxylic acid] +

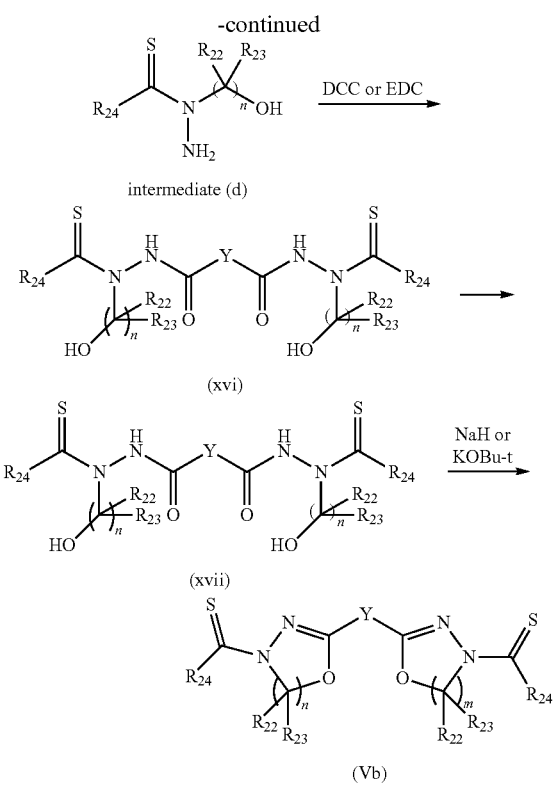

Compounds represented by formula (V) in which X is O and Z is CR can be prepared by the method shown in Scheme XI. In this method, the BOC protecting group is removed from compound (xviii) by treating it with trifluoroacetic acid to form compound (xix). Compound (xix) is reacted with di-acid chloride (xx) in the presence of a base to form compound (xxi), followed by treatment with a strong base such as NaH, LDA or potassium tert-butoxide to form compounds represented by formula (Vc).

Alternatively, compounds represented by formula (V) in which X is O and Z is CR can be prepared by the method shown in Scheme XII. In this method, about one equivalent of compound (xxii) is reacted with di-carboxylic acid (xv) in the presence of EDC to form compound (xxiii). About one equivalent of compound (xiv) is reacted with compound (xxiii) in the presence of EDC to form compound (xxv). The trimethyl silyl groups (TMS) are removed form compound (xxv) by treating it with an acid such as HCl and the compound is cyclized by treating it with p-tosyl chloride and dimethylaminopyridine (DMAP) to form compounds represented by formula (Vd) (see *Organic and Biomolecular Chemistry* (2004), 1315-1329 and *Tetrahedron Lett* (1988), 5561-5566, the entire teachings of each of these references is incorporated herein by reference.

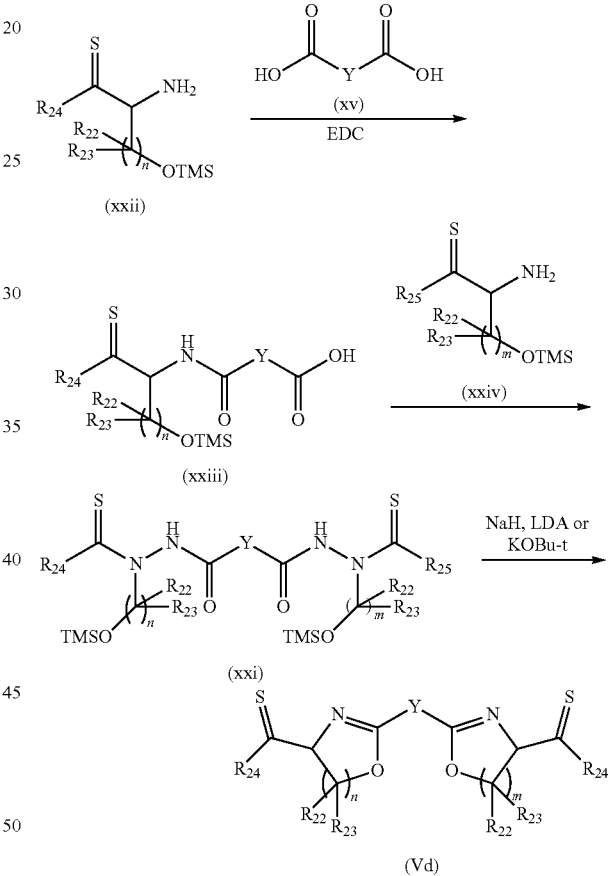

The present invention is illustrated by the following examples, which are not intended to be limiting in any way.

EXEMPLIFICATION

Example 1

Compounds of the Invention Enhance the Anti-Cancer Activity of Anti-Cancer Agents In Vivo A. General Procedure of In Vivo Anti-Tumor Study The in vivo anti-cancer enhancing effect of novel compounds are assessed in tumor bearing mice using the tumor growth inhibition assay. Tumor cells are implanted by injection of a tumor cell suspension subcutaneously in the flank of a mouse. Treatment of the tumor with a compound of the invention and another anti-cancer agent (e.g., paclitaxel, which will be used hereinafter by way of example) is begun after the tumor had been established (volume was about 100 mm$^3$). The animals are then started on a multiple injection schedule where the compound and paclitaxel are given by IV route of administration. Tumors are measured two times a week. During the course of this assay, animals are monitored daily for signs of toxicity including body weight loss.

B. Procedure

A supplemented media is prepared from 50% DMEM/Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate and 1% MEM Non-Essential Amino Acids. FBS is obtained from Sigma Chemical Co. and other ingredients are obtained from Invitrogen Life Technologies, USA). The supplemental Media is warmed to 37° C. and 50 mL of media is added to a 175 cm$^2$ tissue culture flask.

The cells used in the assay are MDA-435 Human Breast Carcinoma from the American Type Culture Collection. 1 vial of MDA-435 cells from the liquid nitrogen frozen cell stock is removed. The frozen vial of cells is immediately placed into a 37° C.: water bath and gently swirled until thawed. The freeze-vial is wiped with 70% ethanol and cells are immediately pipetted into the 175 cm$^2$ tissue culture flask containing supplemented media. The cells are incubated overnight and the media is removed and replaced with fresh supplemented media the next day. The flask is incubated until flask became about 90% confluent. This generally takes anywhere from 5-7 days.

The flask is washed with 10 ml of sterile room temperature phosphate buffered saline (PBS). The cells are trypsinized by adding 5 ml of warmed Trypsin-EDTA (Invitrogen) to the flask of cells. The cells are then incubated for 2-3 minutes at 37° C. until cells begin to detach from the surface of the flask. An equal volume of supplemented media (5 ml) is added to the flask. All the cells are collected into 50 ml tube, and centrifuged at 1000 RPM for 5 minutes at 20° C. The supernatant is aspirated and the cell pellet is resuspended in 10 ml of supplemented media and the cells are counted. 1-3 million cells/flask are seeded into 5-7 tissue culture flasks (175 cm$^2$). Each flask should contain 50 ml of supplemented media. The flasks are incubated until about 90% confluent. The passaging of the cells is repeated until enough cells have been grown for tumor implantation.

The above procedure for trypsinizing and centrifuging the cells are followed. The supernatant is aspirated and the cell pellet is resuspended in 10 ml of sterile PBS and the cells are counted. The cells are centrifuged and then resuspended with appropriate volume of sterile PBS for injection of correct number of cells needed for tumor implantation. In the case of MDA-435, 100 million cells are suspended with 2.0 ml of sterile PBS to a final concentration of 50 million cells/ml in order to inject 5 million cells in 0.1 ml/mouse.

Mice (CD-1 nu/nu) are obtained from Charles River Laboratories: nomenclature: Crl:CD-1-nuBR, Age: 6-8 weeks. The mice are allowed to acclimate for 1 week prior to their being used in an experimental procedure.

Implantation of the MDA-435 tumor cell suspension is generally into the corpus adiposum of the female CD-1 nu/nu mouse. This fat body is located in the ventral abdominal viscera of the mouse. Tumor cells are implanted subsutaneously into the fat body located in the right quadrant of the abdomen at the juncture of the os coxae (pelvic bone) and the os femoris (femur). 5 million MDA-435 cells in 0.1 ml of sterile PBS are injected using 27 G (½ inch) needle. MDA-435 tumors are typically developed 2-3 weeks after implantation.

Compound stock solutions are prepared by dissolving the compound in cell-culture-grade DMSO (dimethyl sulfoxide) at the desired concentration. This stock solution in DMSO is sonicated in an ultrasonic water bath until all the powder dissolved.

The Formulation Solvent is prepared as follows: 20% of Cremophore RH40 (Polyoxyl 40 Hydrogenated Castor Oil obtained from BASF corp.) in water is prepared by first heating 100% Cremophore RH40 in a water bath at 50-60° C. until it liquefied and became clear. 10 ml of the 100% Cremophore RH40 is aliquoted into a conical centrifuge tube containing 40 ml of sterile water (1:5 dilution of Cremophore RH40). The 20% Cremophore RH40 solution is reheated until it became clear again, and mixed by inverting the tube several times. This 20% Cremophore RH40 solution is stored at room temperature, and was kept for up to 3 months.

Preparation of Dosing Solution for Compound Administration: The compound stock solution is diluted 1:10 with 20% Cremophore RH40: 1) 2.0 ml of 10 mg/ml dosing solution of a compound of the invention is prepared by diluting 100 mg/ml Compound Stock solution with 1.8 ml of 20% Cremophore RH40 water solution; and 2) a dosing solution comprising 2.0 ml of 1 mg/ml of Paclitaxel (obtained from Sigma Chemical Co.) and 5 mg/ml of Compound (1) is obtained by mixing 0.1 ml of a compound of the invention DMSO stock solution (50 mg/ml) and 0.1 ml of Paclitaxel DMSO stock solution (10 mg/ml) and diluting with 1.8 ml of 20% Cremophore RH40 water solution. The final formulation for the dosing solution was 10% DMSO, 18% Cremophore RH40 and 72% water.

The Dosing Solution (Dosing Volume: 0.01 ml/gram=10 ml/kg) is injected intravenously into the mice bearing MDA-435 human breast tumor. The table below shows a typical dosing protocol

| Group | Compounds Dosed |
|---|---|
| 1 | Vehicle only |
| 2 | Paclitaxel (5 mg/kg) |
| 3 | Compound of the invention (50 mg/kg) |
| 4 | Paclitaxel (5 mg/kg) and Compound of the invention (25 mg/kg) |
| 5 | Paclitaxel (5 mg/kg) and Compound of the invention (50 mg/kg) |

Results

The compounds of the invention are expected to significantly enhanced anti-tumor activity of Paclitaxel without increasing toxicity.

Examples 2-6

Heat shock proteins (Hsp) are induced under a variety of stress conditions and bind to other proteins to prevent their denaturation. Hsps can protect the cell from apoptotic death. Agents that induce the production of Hsp70 can have protective activity against a wide-range of insults, and may have particular utility in neurological disorders. The neuroprotectant activity of Hsp70 inducing compounds of the invention can be assessed in a variety of animal neurological disease models. Specifically, animal models of stroke, amyotrophic lateral sclerosis, Huntington's disease, Parkinson's disease, and Alzheimer's disease are appropriate settings for testing efficacy. Some example animal models are provided below.

Example 2

Cerebral Ischemia (Stroke)

The benefit of the disclosed treatment with Hsp70 inducing compounds of the invention can be assessed in rodent models of stroke. For example the stroke model described in Longa, et al. (Longa, E. Z., Weinstein, P. R., Carlson, S., and Cummins, R. (1989) Reversible middle cerebral artery occlusion without craniectomy in rats. *Stroke* 20:84-91) can be utilized.

Rats are anesthetized with ketamine, and then infarction is induced by extracranial vascular occlusion. A 4-0 nylon intraluminal suture is placed into the cervical internal carotid artery and is advanced intracranially to block blood flow into the middle cerebral artery. Collateral blood flow is reduced by interrupting all branches of the external carotid artery and all extracranial branches of the internal carotid artery. A compounds of the invention can be dosed just prior to or just after induction of the infarction. The dose may be, for example, 10 to 100 mg/kg body weight administered once per week, three times per week, or daily by any conventional mode of administration, e.g., orally or intravenously. Neurologic deficit, mortality, gross pathology (infarction size), and histochemical staining can be analyzed to assess efficacy of the compounds. Since this is a very acute model, and death is often observed by three days after infarction, the modeling may consist of only a single administration of drug.

Example 3

Familial Amyotrophic Lateral Sclerosis (ALS)

The efficacy of compounds of the invention in the treatment of ALS can be modeled using the SOD1 transgenic mouse model (Gurney, M. E., Pu, H., Chiu, A. Y., Dal Canto, M. C., Polchow, C. Y., Alexander, D. D., Caliendo, J., Hentati, A., Kwon, Y. W., and Deng, H. X. (1994) Motor neuron degeneration in mice that express a human CuZn superoxide dismutase mutation. *Science* 264:1772-1775). Mutations of human CuZn superoxide dismutase (SOD) are found in patients with familial ALS. Expression of the human SOD gene containing a substitution of glycine-to-alanine at amino acid 93 leads to motor neuron disease in transgenic mice. As a result of motor neuron loss from the spinal cord, the mice became paralyzed and die by 5 to 6 months of age.

To test the efficacy of the Hsp70 inducing compounds of the invention, transgenic mice having the SOD1 mutation (SOD1$^{G93A}$) are treated with the compounds, and the effect on disease is monitored. The symptoms are clinically apparent in these animals at 2.5 to 3 months of age. Compounds can be dosed starting at this time. The dose may be, for example, 10 to 100 mg/kg body weight administered once per week or three times per week by the oral or intravenous route. Endpoints include functional impairment of motor function as well as histological changes. The latter endpoints include histopathology of brain and spinal cord assessing degeneration of motor neurons and the appearance of neurofilament-rich inclusions in spinal motor neurons. If long-term administration is performed, the impact on mouse survival can be assessed.

Example 4

Huntington's Disease (HD)

A transgenic mouse model of HD exists, allowing the testing of Hsp70 inducing compounds of the invention for efficacy in this disease setting (Mangiarini, L., Sathasivam, K., Seller, M., Cozens, B., Harper, A., Hetherington, C., Lawton, M., Trottier, Y., Lehrach, H., Davies, S. W., and Bates, G. P. (1996) Exon 1 of the HD gene with an expanded CAG repeat is sufficient to cause a progressive neurological phenotype in transgenic mice. *Cell* 87:493-506; Carter, R. J., Lione, L. A., Humby, T., Mangiarini, L., Mahal, A., Bates, G. P., Dunnett, S. B., and Morton, A. J. (1999) Characterization of progressive motor deficits in mice transgenic for the human Huntington's disease mutation. *J. Neuroscience* 19:3248-3257). HD is caused by a CAG/polyglutamine repeat expansion. These transgenic mice ($R_{6/2}$ transgenics) have the 5' end of the human HD gene with (CAG)115-(CAG)150 repeat expansions. The mice exhibit progressive neurological pathologies similar to HD, including abnormal and involuntary movements, tremors, and epileptic seizures.

These transgenic mice show overt behavioral changes at approximately 8 weeks of age. As early as 5 to 6 weeks of age, they display more subtle deficiencies in motor skills. Hsp70 inducing compounds of the invention can be administered by intravenous or oral administration at doses of 10-100 mg per kg of body weight starting at various times (for example, at 5 to 6 weeks of age). Compounds can be given on multiple different dosing schedules (e.g., once per week versus three times per week). Performance on one or more rodent motor tests such as, swimming tank, beam walking, rotarod apparatus, and footprint test (see Carter, et al., 1999) can be performed to assess the activity of the compounds in preventing loss of neurological function in HD mice.

Example 5

Parkinson's Disease (PD)

There are two widely employed models of PD in which disease is induced by chemical treatment. These are the 6-OHDA (Zigmond, M. J. and Stricker, E. M. (1984) Parkinson's disease: studies with an animal model. *Life Sci.* 35:5-18; Sauer, H. and Oertel, W. H. (1994) Progressive degeneration of nigrostriatal dopamine neurons following intrastriatal terminal lesions with 6-hydroxydopamine: a combined retrograde tracing and immunocytochemical study in the rat. *Neuroscience* 59:401-415) and the MPTP (Langston, J. W., Forno, L. S., Rebert, C. S., and Irwin, I. (1984) Selective nigral toxicity after systemic administration of 1-methyl-4-phenyl-1,2,5,6-tetrahydropyrine (MPTP) in the squirrel monkey. *Brain Res.* 292:390-4) models. An example of a test of Hsp70 inducing compounds of the invention using the 6-OHDA is described.

Young adult male rats are injected with Fluoro-Gold (FG) by stereotactic injection into the striatum in the brain in order to facilitate visualization of the neurons in the substantia nigra, the site of PD. Under anesthesia, 0.2 µl of a 4% solution of FG is administered by stereotactic injection (1 mm anterior from bregma, 3 mm lateral, and 4.5 mm ventral from dura into both striata). One week after FG injection, the rats receive a stereotactic injection of 6-OHDA (20 µg dissolved in 4 µl saline; Sigma) into the striatum on one side of the brain, at the same coordinates as the FG injection. Hsp70 inducing compounds of the invention can be administered by intravenous or oral administration at doses of 10-100 mg per kg of body weight. The compounds can be given at the time of 6-OHDA injection or some time (2-4 weeks, for example) subsequent to 6-OHDA treatment. Rats are sacrificed 8 and 16 weeks after 6-OHDA injection: The endpoints of this model are 1) behavioral changes as monitored in-life at various times by assessment of turning (rotational) behavior using classical neurological read-out, and 2) the brain is removed after sacrifice, thin sections are made using a cryostat, and immunohistochemistry is performed as described in Zigmond and Stricker (1984). Efficacy of the Hsp70 inducing compounds of the invention is demonstrated by a decrease in rotational behavior as well as a reduction in the loss of nigral dopaminergic neurons.

Example 6

Alzheimer's Disease (AD)

There are several transgenic mouse models of AD. One such model that is widely used to test the efficacy of drugs in AD was described by Holcomb, et al. (Holcomb, L., Gordon, M. N., McGowan, E., Yu, X., Benkovic, S., Jantzen, P., Wright, K., Saad, I., Mueller, R., Morgan, D., Sanders, S., Zehr, C., O'Campo, K., Hardy, J., Prada, C. M., Eckman, C., Younkin, S., Hsiao, K., and Duff, K. (1998) Accelerated Alzheimer-type phenotype in transgenic mice carrying both mutant amyloid precursor protein and presenilin 1 transgenes. Nature Medicine 4:97-100). This model contains two different genes associated with AD. One is a mutation in the amyloid precursor protein (APP). The mutant APP (K670N, M671L) transgenic line, Tg2576, has elevated amyloid beta-protein levels at an early age, and, later, develops extracellular AD-type A beta deposits in the brain. The other gene is a mutated presenilin-1 (PS1) gene. The doubly transgenic progeny from a cross between Tg2576 and the PS1 mutant PS1M146L transgenic line develop large numbers of fibrillar A beta deposits in cerebral cortex and hippocampus far earlier than their singly transgenic Tg2576 mice.

Hsp70 inducing compounds of the invention can be dosed in mice at various times. The age of mice at the start of drug dosing may be varied. For example, a treatment starting time may be at 3 months of age, a time at which the brain deposits are first detectable. The dose may be, for example, 10 to 100 mg/kg body weight administered once per week or three times per week by the oral or intravenous route. The effect of drug treatment can be assessed by measuring AD-type deposits in the brain as well as by assessing function of the mice in a maze test.

Example 7

Measurement of Heat Shock Protein 70 (Hsp70)

Plasma Hsp70 can be measured by a sandwich ELISA kit (Stressgen Bioreagents Victoria, British Columbia, CANADA) according to a modified protocol in house. In brief, Hsp70 in plasma specimens and serial concentrations of Hsp70 standard are captured onto 96-well plate on which anti-Hsp70 antibody was coated. Then captured Hsp70 is detected with a biotinylated anti-Hsp70 antibody followed by incubation with europium-conjugated streptavidin. After each incubation unbound materials are removed by washing. Finally; antibody-Hsp70 complex was measured by time resolved fluorometry of europium. Concentration of Hsp70 is calculated from a standard curve.

Example 8

Measurement of Natural Killer Cell Cytotoxic Activity

The following procedure can be employed to assay NK cell activity in a subject. The procedure is adapted from Kantakamalakul W, Jaroenpool J, Pattanapanyasat K. A novel enhanced green fluorescent protein (EGFP)-K562 flow cytometric method for measuring natural killer (NK) cell cytotoxic activity. J Immunol Methods. 2003 Jan. 15; 272:189-197, the entire teachings of which are incorporated herein by reference.

Materials and methods: Human erythroleukaemic cell line, K562, is obtained from American Type Culture Collection (CCL-243, American Type Culture Collection, Manassas, Va.), and cultured in RPMI-1640 medium (Cat#11875-093Gibco Invitrogen Corp, Carlsbad, Calif.) supplemented with 10% heat inactivated fetal calf serum (Gibco), 2 mM L-glutamin, 100 µg/ml streptomycin and 100 IU/ml penicillin at 37° C. with 5% $CO_2$. K562 cells are transduced with retroviral vector which encode green fluorescent protein (eGFP). Stable cell line is selected with antibiotic, G418. About 99.6% G418 resistant cells are eGFP positive after section.

The subject's peripheral blood mononuclear cells (PBMCs) are prepared by clinical study sites and received in BD Vacutainer Cell Preparation Tube with sodium heparin (Product Number: 362753, Becton Dickinson, Franklin Lakes, N.J.).

Two-fold serial dilution of 800 µl effector cells (patient's PBMC) starting at concentration of $1 \times 10^6$ cells/mL are put into four individual polystyrene 12×75-mm tubes. Log phase growing target cells (K562/eGFP) are adjusted with growth medium (RPMI-1640) to a concentration of $1 \times 10^5$ cells/mL and 100 µL targets then added into the tubes to provide effector/target (E/T) ratios of 80:1, 40:1, 20:1, 10:1. Effector cells alone and target cells alone are used as controls. All tubes are incubated at 37° C. with 5% $CO_2$ for about 3.5 hr. Ten microliters of propidium iodide (PI) at a concentration of 1 mg/mL is added to each tube including effector and target control tubes and then incubated at room temperature for 15 min.

Cytotoxic activity is analyzed with a FACSCalibur flow cytometer (Becton Dickinson). Linear amplification of the forward and side scatter (FSC/SSC) signals, as well as logarithmic amplification of eGFP and PI emission in green and red fluorescence is obtained. Ten thousand events per sample tube with no gating for acquisition are collected for analysis. Data analysis for two-parameter dot plots for eGFP versus PI is performed using CELLQuest (Becton Dickinson Biosciences) software to enumerate live and dead target cells. Debris and dead cells are excluded by setting a threshold of forward light scatter.

Example 9

Inhibition of HUVEC Cell Migration

To examine if the compounds of the invention affect endothelial cell function, an in vitro human umbilical vein endothelial cell (HULVEC) migration assay is performed in the presence of a compound of the invention. HUVEC cells (passage number 4) are cultured on 12-well plates and time-lapse imaging is performed with the live cell imaging system on an inverted microscope supplied with 6-7% $CO_2$. The temperature is kept at 37° C. Images are taken every 30 minutes using the 2× objective for up to 106 hr or every 60 seconds using the 20× objective for 30 min. Confluent HUVEC cultures are scraped similarly to make a blank area, followed by culturing in HUVEC medium for 15 hr without treatment. The migration areas, which are imaged as time-lapse sequences for each well, are used as a basis to standardize/correct migration rates. Then, migration of cells under different treatments is imaged at the same time to generate time-lapse image sequences for each well. Time-lapse movies are further analyzed by measuring areas that are covered by migrating cells. During experiments, HUVEC cells are activated by the presence of VEGF and basic FGF. Compounds of the invention (e.g. 100 nM and 1 µM) are expected to completely block migration of HUVEC cells to the blank area, indicating that compounds of the invention possesses potent inhibitory effect on the migration of activated HUVEC cell in vitro induced by VEGF and basic FGF.

It is also possible to track HUVEC behavior during above treatments. It is expected that HUVEC cells will begin to shrink after 24 hr treatment with compounds of the invention.

Example 10

Enhanced VE-Cadherin Junctions of HUVEC Cells

An immunofluoscence study is performed by using anti-VE-cadherin antibodies to examine VE-cadherin junctions between HUVEC cells. HUVEC cells are treated with DMSO or a compound of the invention (e.g. 10, 100 and 1000 nM) for 24 hrs and fixed for immunostaining. DMSO concentration is 1:100 for all treatments. To boost the immunofluorescence signal, cells are stained with a mixture of 2 polyclonal anti-human VE-cadherin Abs followed by staining with a mixture of fluorescent secondary antibodies. It is expected that with compounds of the invention, VE-cadherin staining will be extremely strong in cell-cell junction regions, but not the non-contacted regions compared to that in DMSO treated cultures. Compounds of the invention are expected to enhance the assembly of cell-cell junctions of activated human endothelial cells, likely through induction of the accumulation of VE-cadherin molecules at the junctions. This effect could result in limited motility of the cells and reducing permeability of the endothelium, thus contributing to the cell migration inhibition and the potential anti-angiogenesis effect of compounds of the invention.

Example 11

Syntheses of Compounds 16-22 of the Invention

Compounds 16-22 were prepared as described in Scheme A below:

(Scheme A)

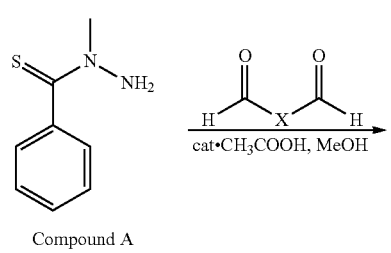

Compound A

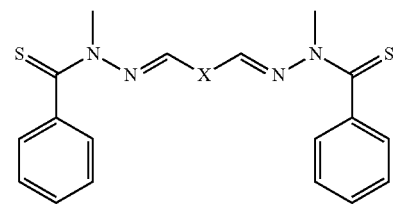

To a solution of Compound A (335 mg, 2.0 mmol) and dialdehyde or ketone (1.0 mmol) in methanol (7 ml) acetic acid (2 drops) was added. The reaction mixture was heated under reflux for 2-15 hr. Completion was judged by TLC. Upon cooling to room temperature, a precipitating has been formed, and the solid was collected by filtration, washed with little amount of methanol and Et$_2$O.

Compound 16: (N',N"E,N',N"E)-N',N"-(pyridine-2,6-diylbis(methan-1-yl-1-ylidene))bis(N-methylbenzothiohydrazide)

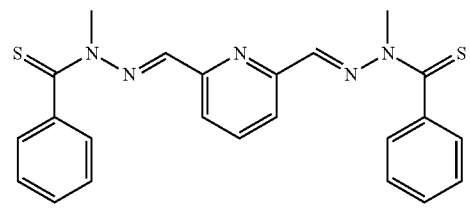 [SMILES: CN(/N=C/c1cccc(/C=N/N(C)C(=S)c2ccccc2)n1)C(=S)c1ccccc1]

ESMS cld for $C_{23}H_{21}S_2$: 431.12. Found: 432.2 (M+H)$^+$.

Compound 17: (N',N"E,N',N"E)-N',N"-(1,3-phenylenebis(methan-1-yl-1-ylidene))bis(N-methylbenzothiohydrazide)

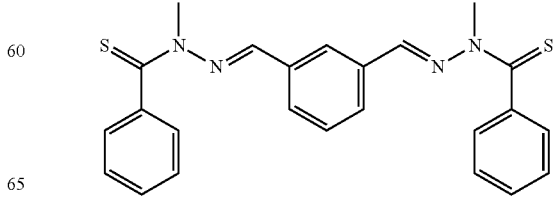

ESMS clcd for $C_{24}H_{22}N_4S_2$: 430.13. Found: 431.2 $(M+H)^+$.

Compound 18: (N',N"E,N',N"E)-N',N"-(1,2-phenylenebis(methan-1-yl-1-ylidene))bis(N-methylbenzothiohydrazide)

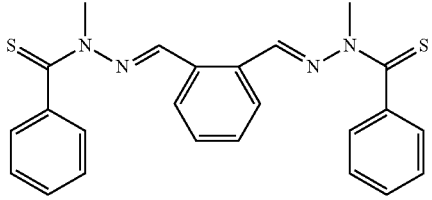 [SMILES: CN(/N=C/c1ccccc1/C=N/N(C)C(=S)c1ccccc1)C(=S)c1ccccc1]

ESMS clcd for $C_{24}H_{22}N_4S_2$: 430.13. Found: 431.2 $(M+H)^+$.

Compound 19: (N',N"E,N',N"E)-N',N"-(furan-2,5-diylbis(methan-1-yl-1-ylidene))bis(N-methylbenzothiohydrazide)

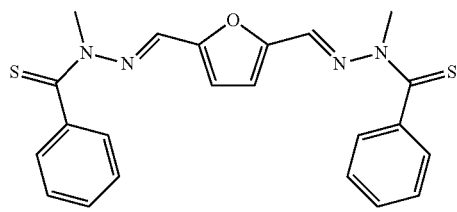 [SMILES: CN(/N=C/c1ccc(/C=N/N(C)C(=S)c2ccccc2)o1)C(=S)c1ccccc1]

ESMS clcd for $C_{22}H_{20}N_4O_2S_2$: 420.11. Found: 421.2 $(M+H)^+$.

Compound 20: (N',N"E,N',N"E)-N',N"-(thiophene-2,5-diylbis(methan-1-yl-1-ylidene))bis(N-methylbenzothiohydrazide)

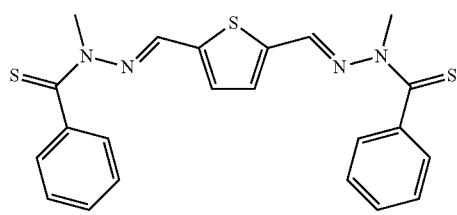

ESMS clcd for $C_{22}H_{20}N_4S_3$: 436.09. Found: 437.2 $(M+H)^+$.

Compound 21: (N',N"E,N',N"E)-N',N"-(cycloheptane-1,3-diylidene)bis(N-methylbenzothiohydrazide)

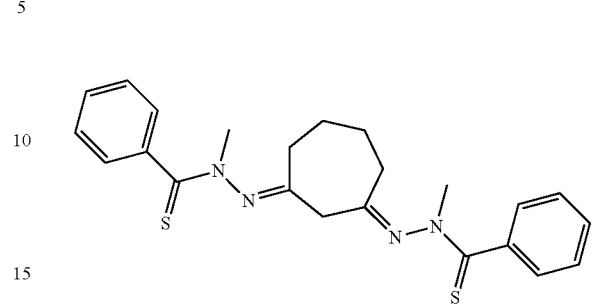

ESMS clcd for $C_{23}H_{26}N_4S_2$: 422.16. Found: 423.3 $(M+H)^+$.

Compound 22: (N',N"E,N',N"E)-N',N"-(cyclohexane-1,3-diylidene)bis(N-methylbenzothiohydrazide)

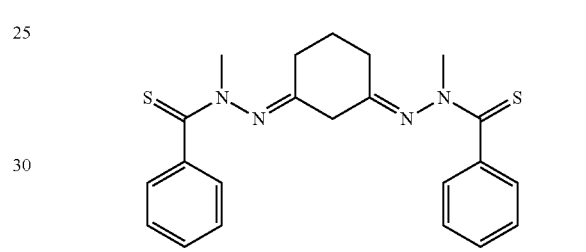

ESMS clcd for $C_{22}H_{24}N_4S_2$: 408.14. Found: 409.2 $(M+H)^+$.

Example 12

Hsp70 Induction by Tested Compounds

The ability of the compounds of the invention to induce Hsp70 RNA induction by quantitative PCR analysis was examined. Ramos B cells were treated with 500 nM each compound for 6 hours and the RNA was isolated from the cells. Quantitative PCR was performed as described below:

Details for Quantitative PCR are as follows:

500 ng of RNA from each sample was used for cDNA synthesis using iScript cDNA Synthesis Kit (Biorad, Cat#170-8891). 1 ul of cDNA mixture was used with the iQ SYBR Green Supermix (Biorad, Cat#170-8882) to perform quantitative PCR in an iCycler machine (Biorad) using standard protocols. QPCR for each sample/time point was performed in duplicate. The following primers for inducible human Hsp70 and gapdh were used:

```
Hsp70-F3   5'-AAG-GAC-ATC-AGC-CAG-AAC-AAG-CG-3'
Hsp70-R3   5'-AAG-AAG-TCC-TGC-AGC-AGC-TTC-TGC-3'
Gapdh-F2   5'-AAG-GTC-GGA-GTC-AAC-GGA-TTT-GGT-3'
Gapdh-R2   5'-CAT-GGT-TCA-CAC-CCA-TGA-CGA-ACA-3'
```

Ct values were obtained from the iCycler program and used in an equation ($2^{-\Delta\Delta C}T$) for determining the amount of target relative to gapdh expression. This compares the relative expression of Hsp70 to the corresponding levels of gapdh in each sample. Duplicate wells were averaged. The amount of N-Malonyl-bis(N'-methyl-N' thiobenzoylhydrazide) (Compound X) induction of Hsp70 was set to 100% and the percent of induction of Hsp70 by the compounds of the invention was determined relative to 100%.

The ability of the compounds of the invention to induce Hsp70 RNA induction by quantitative PCR analysis was listed in the table below.

| Compound No. | % induction relative to Compound X | fold induction over DMSO |
|---|---|---|
| 22 | 0.06 | 0.16 |
| 16 | 0.18 | 0.48 |
| 17 | 0.20 | 0.54 |

The relevant teachings of all publications cited herein that have not explicitly been incorporated herein by reference, are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating an Hsp70 responsive disorder, comprising administering to a subject in need thereof an effective amount of a compound represented by the following structural formula:

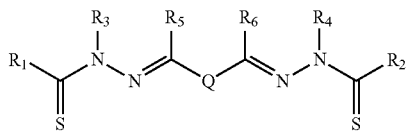

or a tautomer, or pharmaceutically acceptable salt thereof, wherein:

Q is —$(CR_{14}R_{15})_r$—, an optionally substituted $(C_6)$aryl group or an optionally substituted heteroaryl group selected from furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl;

$R_1$ and $R_2$ are each, independently, —H, a halo, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl, wherein the optionally substituted heteroaryl is selected from pyridyl, 1-oxopyridyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolihyl, purinyl, pyrrolo[2,3]pyrimidinyl, pyrazolo[3,4]pyrimidinyl, imidazo[1,2-a]pyridyl, and benzothienyl;

$R_3$ and $R_4$ are each, independently, —H, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl, provided that $R_3$ and $R_4$ are not both —H;

$R_5$ and $R_6$ are each, independently, —H, —$NR_{12}R_{13}$, —$OR_9$, —$SR_9$, a halo, CN, a haloalkyl, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_9$, for each occurrence, is independently, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

$R_{12}$ and $R_{13}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{12}$ and $R_{13}$, taken together with the nitrogen to which they are attached, form an optionally substituted heterocyclyl or an optionally substituted heteroaryl;

$R_{14}$ and $R_{15}$, for each occurrence, are independently, —H a lower alkyl optionally substituted with one or more substituents selected from the group consisting of phenyl, benzyl, halo, cyano, nitro, amino, mono(lower alkyl)amino, di(lower alkyl)amino, lower alkoxy, lower haloalkoxy and —OH; phenyl optionally substituted with one or more substituents selected from the group consisting of lower alkyl, halo, cyano, nitro, amino, mono(lower alkyl)amino, di(lower alkyl)amino, lower alkoxy, lower haloalkoxy and —OH; benzyl optionally substituted with one or more substituents selected from the group consisting of lower alkyl, halo, cyano, nitro, amino, mono(lower alkyl)amino, di(lower alkyl)amino, lower alkoxy, lower haloalkoxy and —OH; lower alkoxy; lower haloalkyl; (lower alkoxy)carbonyl; lower alkylcarbonyl; lower alkylcarboxy; cyano; nitro; lower haloalkoxy; amino; mono(lower alkyl)amino; di(lower alkyl)amino; and —OH; or $R_{14}$ and $R_{15}$, taken together with the carbon to which they are attached, form C(O), C(S), an optionally substituted cycloalkyl, an optionally substituted cycloalkenyl, or an optionally substituted heterocyclyl;

r is an integer from 1 to 6, or a salt thereof.

2. The method of claim 1, wherein the Hsp70 responsive disorder is Alzheimer's disease, Huntington's disease, Parkinson's disease, spongiform encephalopathies, spinal/bulbar muscular atrophy, familial amyotrophic lateral sclerosis, atherosclerosis, cerebral trauma or spinal trauma.

3. The method of claim 1, wherein the Hsp70 responsive disorder is nerve damage caused by chemotherapy.

4. The method of claim 1, wherein the compound is represented by following structural formula:

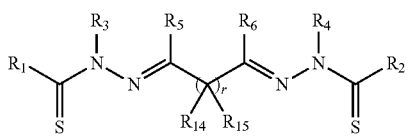

or a tautomer, or pharmaceutically acceptable salt thereof, wherein r is 1 or 2, and $R_{14}$ and $R_{15}$, for each occurrence, are independently, —H, a lower alkyl, or a benzyl.

5. The method of claim 1, wherein the compound is represented by the following structural formula:

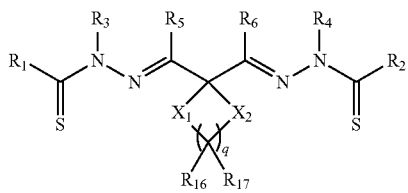

or a tautomer, or pharmaceutically acceptable salt thereof, wherein:

$X_1$ and $X_2$ are each, independently, CRR, O, S, $S(O)_p$, or NR;

each R of CRR is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, a haloalkyl, $—C(O)NR_{33}R_{29}$, $—C(S)NR_{33}R_{29}$, $—C(NR_{32})NR_{33}R_{29}$, $—NR_{30}C(O)R_{31}$, $—NR_{30}C(S)R_{31}$, $—NR_{30}C(NR_{32})R_{31}$, halo, $—OR_{30}$, cyano, nitro, haloalkoxy, $—C(O)R_{30}$, $—C(S)R_{30}$, $—C(NR_{32})R_{30}$, $—NR_{33}R_{29}$, $—C(O)OR_{30}$, $—C(S)OR_{30}$, $—C(NR_{32})OR_{30}$, $—OC(O)R_{30}$, $—OC(S)R_{30}$, $—OC(NR_{32})R_{30}$, $—NR_{30}C(O)NR_{33}R_{29}$, $—NR_{30}C(S)NR_{33}R_{29}$, $—NR_{30}C(NR_{32})NR_{33}R_{29}$, $—OC(O)NR_{33}R_{29}$, $—OC(S)NR_{33}R_{29}$, $—OC(NR_{32})NR_{33}R_{29}$, $—NR_{30}C(O)OR_{31}$, $—NR_{30}C(S)OR_{31}$, $—NR_{30}C(NR_{32})OR_{31}$, $—S(O)_hR_{30}$, $—OS(O)_pR_{30}$, $—NR_{30}S(O)_pR_{30}$, $—S(O)_pNR_{33}R_{29}$, $—OS(O)_pNR_{33}R_{29}$, or $—NR_{30}S(O)_pNR_{33}R_{29}$, wherein:

$R_{29}$ and $R_{33}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{33}$ and $R_{29}$ taken together with the nitrogen to which they are attached form an optionally substituted heterocyclyl or optionally substituted heteroaryl;

$R_{30}$ and $R_{31}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; and $R_{32}$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, $—C(O)R_{30}$, $—C(O)NR_{33}R_{29}$, $—S(O)_pR_{30}$, or $—S(O)_pNR_{33}R_{29}$;

p is 1 or 2; h is 0, 1 or 2;

each R of NR is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, an alkoxy and a haloalkoxy;

$R_{16}$ and $R_{17}$, for each occurrence, are independently, —H or lower alkyl optionally substituted with one or more substituents selected from the group consisting of phenyl, benzyl, halo, cyano, nitro, amino, mono (lower alkyl)amino, di(lower alkyl)amino, lower alkoxy, lower haloalkoxy and —OH; phenyl optionally substituted with one or more substituents selected from the group consisting of lower alkyl, halo, cyano, nitro, amino, mono(lower alkyl)amino, di(lower alkyl)amino, lower alkoxy, lower haloalkoxy and —OH; benzyl optionally substituted with one or more substituents selected from the group consisting of lower alkyl, halo, cyano, nitro, amino, mono(lower alkyl)amino, di(lower alkyl)amino, lower alkoxy, lower haloalkoxy and —OH; lower alkoxy; lower haloalkyl; (lower alkoxy)carbonyl; lower alkylcarbonyl; lower alkylcarboxy; cyano; nitro; lower haloalkoxy; amino; mono(lower alkyl)amino; di(lower alkyl)amino; and —OH q is 2 or 3; and p is 1or 2.

6. The method of claim 5, wherein:

$X_1$ and $X_2$ are both CRR or both O; and

R, for each occurrence, is independently, —H or a lower alkyl.

7. The method of claim 1, wherein Q is an optionally substituted 5-14 membered heteroaryl group selected from furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl.

8. The method of claim 7, wherein the heteroaryl group represented by Q is selected from the group consisting of:

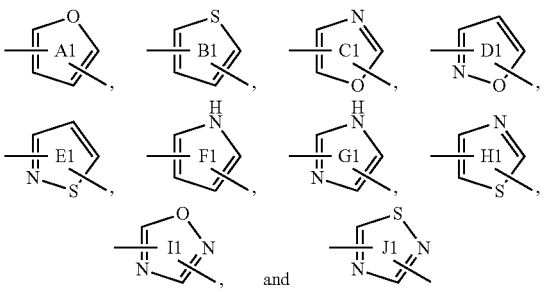

wherein each of rings A1-J1 independently is optionally substituted.

9. The method of claim 1 wherein $R_5$ and $R_6$ are, independently, —H, a lower alkyl, a lower alkoxy, or a lower sulfanyl.

10. The method of claim 9, wherein:
$R_1$ and $R_2$ independently are an optionally substituted aryl or an optionally substituted heteroaryl; and
$R_3$ and $R_4$ are each an optionally substituted alkyl, an optionally substituted alkenyl, an optionally substituted alkynyl, an optionally substituted cycloalkyl, an optionally substituted cycloalkenyl, and optionally substituted heterocyclyl.

11. The method of claim 10, wherein $R_1$ and $R_2$ are each a substituted or unsubstituted phenyl group; and $R_3$ and $R_4$ are each methyl or ethyl.

12. The method of claim 9, wherein $R_1$ and $R_2$ are both an optionally substituted alkyl, an optionally substituted alkenyl, an optionally substituted alkynyl, an optionally substituted cycloalkyl, an optionally substituted cycloalkenyl, an optionally substituted heterocyclyl.

13. The method of claim 12, wherein $R_1$ and $R_2$ are both a C3-C8 cycloalkyl group optionally substituted with at least one alkyl group; $R_3$ and $R_4$ are both an alkyl group.

14. The method of claim 13, wherein $R_1$ and $R_2$ are both cyclopropyl or
1-methylcyclopropyl.

15. The method of claim 1, wherein:
$R_1$ and $R_2$ are both phenyl, and $R_3$ and $R_4$ are both methyl;
$R_1$ and $R_2$ are both phenyl, and $R_3$ and $R_4$ are both ethyl;
$R_1$ and $R_2$ are both 4-cyanophenyl, and $R_3$ and $R_4$ are both methyl;
$R_1$ and $R_2$ are both 4-methoxyphenyl, and $R_3$ and $R_4$ are both methyl;
$R_1$ and $R_2$ are both 2,5-dimethoxyphenyl, and $R_3$ and $R_4$ are both methyl;
$R_1$ and $R_2$ are both 3-cyanophenyl, and $R_3$ and $R_4$ are both methyl;
$R_1$ and $R_2$ are both 3-fluorophenyl, and $R_3$ and $R_4$ are both methyl;
$R_1$ and $R_2$ are both 4-chlorophenyl, and $R_3$ and $R_4$ are both methyl;
$R_1$ and $R_2$ are both 2-methoxyphenyl, and $R_3$ and $R_4$ are both methyl;
$R_1$ and $R_2$ are both 3-methoxyphenyl, and $R_3$ and $R_4$ are both methyl;
$R_1$ and $R_2$ are both 2,3-dimethoxyphenyl, and $R_3$ and $R_4$ are both methyl;
$R_1$ and $R_2$ are both 2,5-difluorophenyl, and $R_3$ and $R_4$ are both methyl;
$R_1$ and $R_2$ are both 2,5-dichlorophenyl, and $R_3$ and $R_4$ are both methyl;
$R_1$ and $R_2$ are both 2,5-dimethylphenyl, and $R_3$ and $R_4$ are both methyl;
$R_1$ and $R_2$ are both cyclopropyl, and $R_3$ and $R_4$ are both methyl;
$R_1$ and $R_2$ are both cyclopropyl, and $R_3$ and $R_4$ are both ethyl;
$R_1$ and $R_2$ are both 1-methylcyclopropyl, and $R_3$ and $R_4$ are both methyl;
$R_1$ and $R_2$ are both 1-methylcyclopropyl, and $R_3$ and $R_4$ are both ethyl;
$R_1$ and $R_2$ are both 1-methylcyclopropyl, and $R_3$ is methyl, and $R_4$ is ethyl;
$R_1$ and $R_2$ are both 2-methylcyclopropyl, and $R_3$ and $R_4$ are both methyl;
$R_1$ and $R_2$ are both 2-phenylcyclopropyl, and $R_3$ and $R_4$ are both methyl;
$R_1$ and $R_2$ are both 1-phenylcyclopropyl, and $R_3$ and $R_4$ are both methyl;
$R_1$ and $R_2$ are both cyclobutyl, and $R_3$ and $R_4$ are both methyl;
$R_1$ and $R_2$ are both cyclopentyl, and $R_3$ and $R_4$ are both methyl;
$R_1$ and $R_2$ are both cyclohexyl, and $R_3$ and $R_4$ are both methyl;
$R_1$ and $R_2$ are both cyclohexyl, and $R_3$ and $R_4$ are both phenyl;
$R_1$ and $R_2$ are both methyl, and $R_3$ and $R_4$ are both methyl;
$R_1$ and $R_2$ are both methyl, and $R_3$ and $R_4$ are both t-butyl;
$R_1$ and $R_2$ are both methyl, and $R_3$ and $R_4$ are both phenyl;
$R_1$ and $R_2$ are both t-butyl, and $R_3$ and $R_4$ are both methyl;
$R_1$ and $R_2$ are ethyl, and $R_3$ and $R_4$ are both methyl; or $R_1$ and $R_2$ are both n-propyl, and $R_3$ and $R_4$ are both methyl.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
aaggacatca gccagaacaa gcg                                          23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
aagaagtcct gcagcagctt ctgc                                         24

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
aaggtcggag tcaacggatt tggt                                         24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
catggttcac acccatgacg aaca                                         24